US006022951A

United States Patent [19]
Sano et al.

[11] Patent Number: 6,022,951
[45] Date of Patent: Feb. 8, 2000

[54] STREPTAVIDIN MUTANTS

[76] Inventors: Takeshi Sano, 1 Longfellow Pl. #2715, Boston, Mass. 02114; Charles R. Cantor, 11 Bay State Rd. #6, Boston, Mass. 02215; Sandor Vajda, 8 Hillcrest Rd., Medfield, Mass. 02050; Gabriel O. Reznik, 270 Babcock St., #7F, Boston, Mass. 02215; Cassandra L. Smith, 11 Bay State Rd. #6, Boston, Mass. 02215; Mark W. Pandori, 9605 Genesee Ave., #E2, San Diego, Calif. 92121

[21] Appl. No.: 08/628,540

[22] Filed: Apr. 10, 1996

Related U.S. Application Data

[63] Continuation-in-part of application No. 08/420,010, Apr. 11, 1995, abandoned
[60] Provisional application No. 60/003,687, Sep. 18, 1995.

[51] Int. Cl.$^7$ .................................................. C07K 14/36
[52] U.S. Cl. .......................... 530/350; 530/402; 530/810; 530/808
[58] Field of Search .................................... 530/350, 402, 530/810, 808

[56] References Cited

U.S. PATENT DOCUMENTS

| | | | |
|---|---|---|---|
| 4,839,293 | 6/1989 | Cantor et al. | 435/357 |
| 5,328,985 | 7/1994 | Sano et al. | 530/350 |
| 5,672,691 | 9/1997 | Kopetzki et al. | 530/413 |

FOREIGN PATENT DOCUMENTS

| | | |
|---|---|---|
| 4135543 | 4/1993 | Germany. |
| WO8903422 | 4/1989 | WIPO. |

OTHER PUBLICATIONS

Sano et al. "A streptavidin mutant containing a cysteine stretch that facilitates production of a variety of specific streptavidin conjugates." Bio/technology 11: 201–206, Feb. 11, 1993.

Pahler, et al, "Characterization and Crystallization of Core Streptavidin.",*J. Biol. Chem,* Oct. 15, 1987, vol. 262 No. 29, pp. 13933–13937.

"Abstract", Argarana, et al., "Molecular Cloning and Nucleotide Sequence of the Streptavidin Gene", *Nucleic Acids Res.,* Feb. 25, 1986; vol. 14, No. 4, pp. 1871–1882.

Sano et al., "A streptavidin—metallothionein chimera that allows specific labeling of biological materials with many different heavy metal ions", *Proc. Natl. Acad. Sci., USA,* Mar. 1992, vol. 891, pp. 1534–1538.

Wilchek, et al., "Avidin—Biotin Technology", *Methods in Enzymology,* 1990, Academic Press, Inc., vol. 184, pp. 5–13.

Savage, et al., "Components of Avidin—Biotin Technology",*Avidin–Biotin Chemistry: A Handbook,* Pierce Chemical Company, 1992.

Sano et al., "Expression of a cloned streptavidin gene in Escherichia coli", *Proc. Natl. Acad. Sci., USA,* Jan. 1990, vol. 87, pp. 142–146.

Sano et al.,"Expression Vectors for Streptavidin—Containing Chimeric Proteins", *Biochemical and Biophysical Research Communications,* Apr. 30, 1991, vol. 176, No. 2, pp. 571–577.

Chilkoti, et al., "Site–directed mutagenesis studies of the high–affinity streptavidin—biotin complex: Contributions of tryptophan residues 79, 108, and 120", *Proc. Natl. Acad. Sci., USA,* Feb. 1995, vol. 92, pp. 1754–1758.

Wilchek, et al., "Introduction to Avidin–Biotin Technology", *Methods in Enzymology,* Avidin–Biotin Technology, vol. 184, pp. 5–13.

Zoller, et al., "Oligonucleotide–Directed Mutagenesis of DNA Fragments Cloned into M13 Vectors", *Methods in Enzymology,* (1983) Recombinant DNA Part B, vol. 100, pp. 468–501.

Phillips, et al., "Isolation of Specific Lymphocyte Receptors by High–Performance Immunoaffinity Chromatography", *Journal of Chromatography,* (1988) vol. 444, pp. 13–20.

Alon et al., "Cell–adhesive properties of streptavidin are mediated by the exposure of an RGD–like RYD site" *Eur. J. Cell Biol.,* Apr. 24, 1992, vol. 58(2), pp. 271–279.

Sano, et al., "Intersubunit contacts made by tryptophan 120 with biotin are essential for both string biotin binding and biotin–induced tighter subunit association of streptavidin,", *Proc. Natl. Acad. of Science, U.S.A.,* Apr. 1995, vol. 92, pp. 3180–3184.

Sano, et al., "Recombinant Core Streptavidins" *J. Biol. Chem.* Jul. 26, 1995, vol. 270, No. 47, Issue of Nov. 24, 1995, pp. 28204–28209.

Mathews, et al., "Introduction to Proteins: The Primary Level of Protein Structure", Oregon State University *Biochemistry,* Chapter 5, pp. 137–141, Redwood City CA: The Benjamin/Cummings Publishing Co. (1990).

Gitlin, et al., "Studies on the biotin–binding site of streptavidin", *Biochem. J.* (1988), vol. 256, pp. 279–282.

Chetverin, et al. "Oligonucleotide Arrays: New Concepts and Possibilities", *Bio/Technology* vol. 12, Nov. 1994, pp. 1093–1099.

*Primary Examiner*—Robert A. Wax
*Assistant Examiner*—Gabriele E. Bugaisky

[57] ABSTRACT

The present invention relates to streptavidin proteins and peptides having a altered physical properties such as an increased stability or increased or decreased affinity for binding biotin. The invention also relates to methods for the detection, identification, separation and isolation of targets using streptavidin proteins or peptides. Streptavidin with increased or reduced affinity allows for the use of the streptavidin-biotin coupling systems for detection and isolation systems wherein it is necessary to remove of one or the other of the binding partners. Such systems are useful for the purification of functional proteins and viable cells. The invention also relates to nucleic acids which encode these streptavidin proteins and peptides and to recombinant cells such as bacteria, yeast and mammalian cells which contain these nucleic acids.

31 Claims, 28 Drawing Sheets

MATURE, FULL-LENGTH STREPTAVIDIN (159 RESIDUES, 16.5 kDa)

1 — DPSKD SKAQV SAAEA GITGT — 21 ... 130 — TKVKP SAASI DAAKK AGVNN GNPLD AVQQ — 159

NATURAL CORE STREPTAVIDIN (127 RESIDUES, 13.3 kDa)

13 — AEA GITGT — 21 ... 130 — TKVKP SAAS — 139

STV-25 (126 RESIDUES, 13.2 kDa)

14 — M EA GITGT — 21 ... 130 — TKVKP SAA — 138

STV-13 (119 RESIDUES, 12.6 kDa)

16 — M GITGT — 21 ... 130 — TKV — 133

FIG. 6

STREPTAVIDIN MUTANTS

REFERENCE TO RELATED APPLICATIONS

This patent application is a continuation of U.S. patent application Ser. No. 08/420,010, filed Apr. 11, 1995, now abandoned ; and provisional application, Ser. No. 60/003,687, filed Sep. 18, 1995.

RIGHTS IN THE INVENTION

This invention was made with United States Government support under grant number DE-FG02-93ER61656, awarded by the United States Department of Energy, and grant number CA39782, awarded by the National Cancer Institute, and the United States Government has certain rights in the invention.

BACKGROUND

1. Field of the Invention

This invention relates to recombinant streptavidin proteins that bind biotin, to recombinant streptavidin proteins having an altered affinity for binding biotin and to methods utilizing recombinant streptavidin proteins for the detection and isolation of targets. The invention also relates to nucleic acids encoding recombinant streptavidin proteins and to recombinant cells which contain and express proteins encoded by these nucleic acids.

2. Description of the Background

Streptavidin, and its functional homolog avidin have been extensively used in biological and medical science due in large part to their ability to specifically bind biotin. Binding has a very high affinity of about $10^{15}$ $M^{-1}$, and is one of the strongest known non-covalent interactions (N. M. Green, Methods Enzymol. 184:5–13,1990). This extraordinary affinity, coupled with the ability of biotin and its derivatives to be incorporated easily into various biological materials, endows streptavidin-biotin systems with great versatility.

Although avidin and streptavidin have almost the same high affinity for biotin, they are different in many other respects. The two proteins have different molecular weights, electrophoretic mobilities and overall amino acid composition. Avidin is a glycoprotein found in egg whites and the tissues of birds, reptiles and amphibia. Like streptavidin, avidin has almost the same high affinity for biotin and exists as a tetramer with a molecular weight of between about 67,000 to about 68,000 daltons. Avidin also has a high isoelectric point of between about 10 to about 10.5 and contains carbohydrates which cause it to bind non-specifically to biological materials including cell nuclei, nucleic acids and lectins. These non-specific interactions make avidin less suitable than streptavidin for many applications.

Biotin, also known as vitamin H or cis-hexahydro-2-oxo-1H-thieno-(3,4)-imidazole-4-pentanoic acid, is an essential vitamin found in every living cell including bacteria and yeast. In mammals, the tissues having the highest amounts of biotin are the liver, kidney and pancreas. Biotin levels also tend to be raised in tumors and tumor cells. In addition to cells, biotin can be isolated from secretions such as milk which has a fairly high biotin content. Biotin has a molecular weight of about 244 daltons, much lower than its binding partners avidin and streptavidin. Biotin is also an enzyme cofactor of pyruvate carboxylase, trans-carboxylase, acetyl-CoA-carboxylase and beta-methylcrotonyl-CoA carboxylase which together carboxylate a wide variety of substrates.

Only the intact bicyclic ring of biotin is required for the strong binding to streptavidin. The carboxyl group of biotin's pentanoic acid side chain has little to contribute to this interaction. Consequently, biotin derivatives, reactive to a variety of functional groups, can be prepared by modifying the pentanoic acid carboxyl group without significantly altering the target's physical characteristics or biological activity. This allows biotin to be conjugated to a number of target molecules.

Streptavidin is produced by the bacteria, *Streptomyces avidini*, and exists as a tetrameric protein having four identical subunits. The full length streptavidin monomer is 159 amino acids in length, some 30 residues longer than avidin. It contains no carbohydrate and has an acidic iso-electric point of about 5.0 which accounts, in part, for the low non-specific binding level. Each subunit of streptavidin is initially synthesized as a precursor of 18,000 daltons which forms a tetramer of about 75,000 daltons. Secretion and post-secretory processing results in mature subunits having an apparent size of 14,000 daltons. Processing occurs at both the amino and carboxyl termini to produce a core protein of about 13,500 daltons, having about 125 to 127 amino acids. This core streptavidin forms tetramers and binds to biotin as efficiently as natural streptavidin. The amino acid sequence of the mature 160 amino acid protein is as follows:

```
1
XPSKDSKAQVSAAEAGITGTWYNQLGSTFIVTAGADGALT      (SEQ ID NO 1)
41
GTYESAVGNAESRYVLTGRYDSAPATDGSGTALGWTVAWK
81
NNYRNAHSATTWSGQYVGGAEARINTQWLLTSGTTEANAW
121
KSTLVGHDTFTKVKPSAASIDAAKKAGVNNGNPLDAVQQ-159
```

A natural streptavidin tetramer is formed by interdigitating a pair of streptavidin dimers with their dyad axes coincident (W. A. Hendrickson et al., Proc. Natl. Acad. Sci. USA 86:2190–94,1989). A tetramer is stabilized by numerous van der Waals forces, with subunits forming a symmetric dimer additionally connected by hydrogen bonds near the carboxyl terminus. This force distribution within a tetramer indicates that there are two classes of subunit interfaces. One interface is between subunits in a stable symmetric dimer and the other is between two stable dimers. When the dissociation of a tetramer occurs, it is likely that the interface between two stable dimers would be first disrupted because this has lower stability than that between two subunits in a stable dimer. If such dissociation occurred, the resulting dimeric molecules should have much reduced affinity for biotin because of the lack of contacts made by Trp-120 of an adjacent subunit to biotin through the dimer—dimer interface (A. Chilkoti et al., Proc. Natl. Acad. Sci. USA 92:1754–58,1995; T. Sano et al., Proc. Natl. Acad. Sci. USA 92:3180–84,1995). This might explain why the dissociation of biotin from streptavidin can be observed even under relatively mild conditions, despite the very high biotin-binding affinity of streptavidin.

The mature streptavidin tetramer binds one molecule of biotin per subunit and the complex, once formed, is unaffected by most extremes of Ph, organic solvents and denaturing conditions. Separation of streptavidin from biotin requires harsh conditions, such as 8 M guanidine, pH 1.5, or autoclaving at 121° C. for 10 minutes.

The advantages of streptavidin-biotin binding systems are numerous. The exceptionally high affinity and stability of the complex ensures complete reaction. Biotin's small size allows it to be conjugated to most molecules with no loss in molecular activity. Multiplicity of biotinylation sites combined with the tetrameric structure of streptavidin allows for amplification of the desired signal. The system is extremely versatile, as demonstrated by the large number of functional targets, binders and probes. The system is amenable to multiple labelling techniques, a wide variety of biotinylated agents and streptavidin-containing probes are commercially available.

Streptavidin-biotin complexes are used in a number of diagnostic and purification technologies. In general, a target molecule to be purified or detected is bound either directly to biotin or to a biotinylated intermediate. The binder may be almost any molecule or macromolecule that will complex with or conjugate to a target molecule. For example, if a particular antigen is the target, its binder would be an antibody. The biotinylated target is bound to streptavidin which may be bound to a probe for ease of detection. This basic technique is utilized in chromatography, cytochemistry, histochemistry, pathological probing, immunoassays, bioaffmity sensors and cross-linking agents, as well as more specific techniques such as targeting, drug delivery, flow cytometry and cytological probing.

The origins of the unusually high binding affinity seen in streptavidin-biotin complexes has not been fully elucidated. X-ray crystallographic studies have shown that streptavidin's carboxyl and amino termini lie on the molecule's surface (P. C. Weber et al., J. Am. Chem. Soc. 114:3197–200, 1992). These termini have been modified by cleavage or conjugation with a minimal effect on biotin binding affinity.

The streptavidin-biotin complex does not involve any covalent bonds, but does contain many hydrogen bonds, hydrophobic interactions and van der Waal interactions. These interactions are largely mediated by the aromatic side chains of tryptophan. Two tryptophan-lysine pairs are conserved between streptavidin and avidin. These pairs are found at positions 79–80 and 120–121 in streptavidin. Additional tryptophan residues in streptavidin are found at positions 92, 108 and 120.

Although participation of tryptophan residues in biotin-binding has been indicated, a quantitative understanding of Trp-120's contribution to biotin-binding has not been reported. Streptavidin's six tryptophan residues per subunit make conventional chemical modifications of any one specific tryptophan residue difficult a situation exacerbated by the tetrameric nature of streptavidin. The Trp-120 of one particular streptavidin subunit makes contact with the biotin bound to an adjacent subunit (A. Pähler et al.,J. Biol. Chem. 262:13,933–37,1987). This residue contacts the alkyl moiety of biotin's pentanoyl group in an apparent hydrophobic interaction. Streptavidin's subunit association is made tighter upon biotin-binding (*Advances in Biomagnetic Separation*, T. Sano et al., Eaton Publishing, Natick, Mass., 1994). Because the contact made by Trp-120 to the biotin of an adjacent subunit occurs through the dimer—dimer interface, this residue possibly plays a key role in the biotin-induced tighter association of streptavidin. However, because streptavidin's Trp-120 residue is adjacent to a lysine, both of which are conserved in avidin, lysine may also have a role in binding. Lysine is known to play a critical role in avidin-biotin complex formation. For example, when an avidin lysine at positions 45, 94 or 111 is bound to a dinitrophenyl group, activity is abolished (*Avidin-Biotin Chemistry: A Handbook*, M. D. Savage et al., editors, page 7, 1992).

Trp-120 may play a role in maintaining local structures of streptavidin, particularly around the biotin-binding sites and the dimer—dimer interface. Strong hydrophobicity is observed around Trp-120 and three other tryptophan residues (Trp-79, 92 and 108) that make contact with biotin (P. C. Weber et al., Sci. 243:85–88,1989; C. E. Argara ña et al., Nuc. Acids Res. 14:1871–82, 1986). In addition, hydrophobic interactions are the major force for the stable association of the two symmetric streptavidin dimers. Changes in local environment caused by the mutation of Trp-120 could prevent the molecule from folding correctly, resulting in diminished biotin-binding ability. In fact, the conversion of some amino acid residues located around the dimer—dimer interface to hydrophilic amino acids causes the formation of insoluble aggregates, probably due to random inter-molecular interactions.

Streptavidin's herculean affinity for biotin is unfortunately its major drawback. The streptavidin-biotin binding system is essentially irreversible. The streptavidin-biotin bond is not affected by pH values between 2 to 13, nor by guanidine-HCl concentrations up to 8 M (neutral pH). The half-life for spontaneous dissociation of the streptavidin-biotin bond is about 2.5 years. The extremely strong binding of biotin to streptavidin means that biotinylated proteins can only be recovered from streptavidin supports under denaturing conditions. This sort of system is inappropriate for many procedures such as, one of its principal uses, the purification of delicate proteins. Streptavidin-biotin cannot be used in sequential assays to detect specific types of biomolecules, macromolecular complexes, viruses or cells present in a single sample. The high affinity necessitates the use of harsh chemical reagents, complex procedures, and careful monitoring of the reactions. This also limits both yields and the ability to fully automate such reactions.

A number of methods have been developed in an attempt to create a releasible streptavidin-biotin or avidin-biotin conjugate. These methods include partly monomeric avidin beads, N-hydroxysuccinimide-iminobiotin and biotin or streptavidin cleavage.

Monomeric avidin beads are formed by denaturing tetrameric avidin and coupling the denatured protein to chromatography beads. Thus, the so-called monomeric avidin is really a mixture of monomeric, dimeric and tetrameric proteins that have a binding affinity distributed between the wild type affinity of $10^{15}$ $M^{-1}$ and the reduced affinity of $10^8$ $M^{-1}$. Thus, monomeric avidin beads produce low yields because some of the biotinylated products are irreversibly bound. Furthermore, the density and capacity of monomeric avidin beads is low.

N-hydroxysuccinimide-iminobiotin (NHS-iminobiotin) is a guanido analog of NHS-biotin with a pH sensitive binding affinity for streptavidin. The complete dissociation of NHS-iminobiotin from streptavidin occurs at low pH without the need for strong denaturants. The drawback to the NHS-iminobiotin system is that binding requires a pH of 9.5 or greater, while release requires a pH of less than 4. Thus, the use of NHS-iminobiotin is limited to those few molecules which are stable over a wide pH range.

One method used to dissociate the streptavidin-biotin bond involves proteinase K digestion of streptavidin (M. Wilchek et al., Anal. Biochem. 171:1–32, 1988). However, significant amounts of the streptavidin molecules remain attached even after proteinase K treatment. Proteinase K is useful only when the biotinylated product does not comprise proteins. Furthermore, this system precludes sequential assays or transfers of target.

Another method of release involves biotin cleavage of the binding partners, for example, of a cleavable biotin such as immunopure NHS-SS-biotin which is commercially available (Pierce Chemical Co.; Rockford, Ill.). NHS-SS-biotin consists of a biotin molecule linked through a disulfide bond and an N-hydroxysuccinimide ester group that reacts selectively with primary amines. Using this group, NHS-SS-biotin is linked to a target molecule and the biotin portion removed by thiol cleavage. This complex approach is slow and of limited use since thiols normally disrupt native protein disulfide bonds. Furthermore, cleavage leaves a reactive sulfhydryl group that tends to react with other components of the mixture. Also, thiol-contaning nucleic acids will no longer hybridize, severely limiting their usefulness.

SUMMARY OF THE INVENTION

The invention overcomes the problems and disadvantages associated with current strategies and designs and provides streptavidin proteins and peptides with increased stability and reduced or enhanced affinity for biotin, and methods for utilizing these streptavidin in detection, identification, isolation and purification techniques.

One embodiment of the invention is directed to streptavidin proteins and peptides with increased stability in solution and an altered affinity for biotin. Stable streptavidin proteins bind to at least about 0.8 molecules of biotin per subunit in 6 M guanidine hydrochloride at pH 7.4. Proteins may be comprised of two or four chains of streptavidin peptides comprised of at least about the amino acid sequence of streptavidin from about positions 13 to 139, 14 to 138 or 16 to 133. These protein are soluble in up to 80% ethanol and most concentrations of ammonium sulfate.

Another embodiment of the invention is directed to streptavidin proteins comprised of at least most of the sequences of streptavidin from about position 21 to 130. These proteins may also contain a substitution of lysine, aspartic acid or cysteine for histidine at position 127, a deletion of positions 113 to 120, or the addition of one or more cysteines to the amino or carboxyl terminus of the protein. Proteins form dimers and tetramers which may combine into homotetramers or heterotetramers. Streptavidin proteins may also be crosslinked forming more stable tetramers which may have a reduced or increased affinity for biotin.

Another embodiment of the invention is directed to streptavidin protein which comprise an amino acid sequence of streptavidin wherein the proteins have an increased biotin-binding affinity. Proteins comprise at least most of the amino acid sequence of streptavidin from positions 21 to 130 with a cysteine, lysine or aspartic acid at position 127. Biotin binding of the recombinant proteins is greater than about $10^{12}$ $M^{-1}$. Recombinant proteins may be coupled to solid supports or free in aqueous solutions.

Another embodiment of the invention is directed to streptavidin protein which comprise an amino acid sequence of streptavidin wherein the proteins have a reduced biotin-binding affinity. Proteins comprise at least most of the amino acid sequence of streptavidin from positions 21 to 130 with a phenylalanine at position 120 or a deletion of the amino acid sequence from positions 113 to 120. Biotin binding of the recombinant proteins is less than about $10^{12}$ $M^{-1}$. Recombinant proteins may be coupled to solid supports or free in aqueous solutions.

Another embodiment of the invention is directed to nucleic acids which encode streptavidin proteins of the invention. Recombinant nucleic acids may be encoded within plasmids and replicated, chemically synthesized, or transformed into eukaryotic cells.

Another embodiment of the invention is directed to cells which comprise nucleic acids that encode streptavidin proteins of the invention. Cells may be prokaryotic or eukaryotic and may constitutively or inducible express recombinant streptavidin protein.

Another embodiment of the invention is directed to methods for detecting or puriiying a target from a heterogenous mixture which contains the target. The target to be purified is biotinylated with biotin or derivative of biotin and contacted to a support to which is attached a streptavidin protein of the invention. The components of the heterogenous mixture can be removed and the target isolated. Alternatively, target may be coupled with streptavidin and the support coupled with biotin. The target can be purified after contact with the support.

Another embodiment of the invention is directed to methods for targeting a pharmaceutical agent to a cell wherein the agent is coupled to a streptavidin of the invention and the cell contains biotin. Such methods can be used to treat or prevent disorders such as infections and neoplasms.

Another embodiment of the invention is directed to kits which contain a streptavidin protein of the invention and, optionally, additional reagents for the detection or isolation of target substances.

Other embodiments and advantages of the invention are set forth, in part, in the description which follows and, in part, will be obvious from this description and may be learned from the practice of the invention.

DESCRIPTION OF THE DRAWINGS

FIG. 6 Schematic illustration of the structures of four streptavidin constructs.

DESCRIPTION OF THE INVENTION

Figure 1:
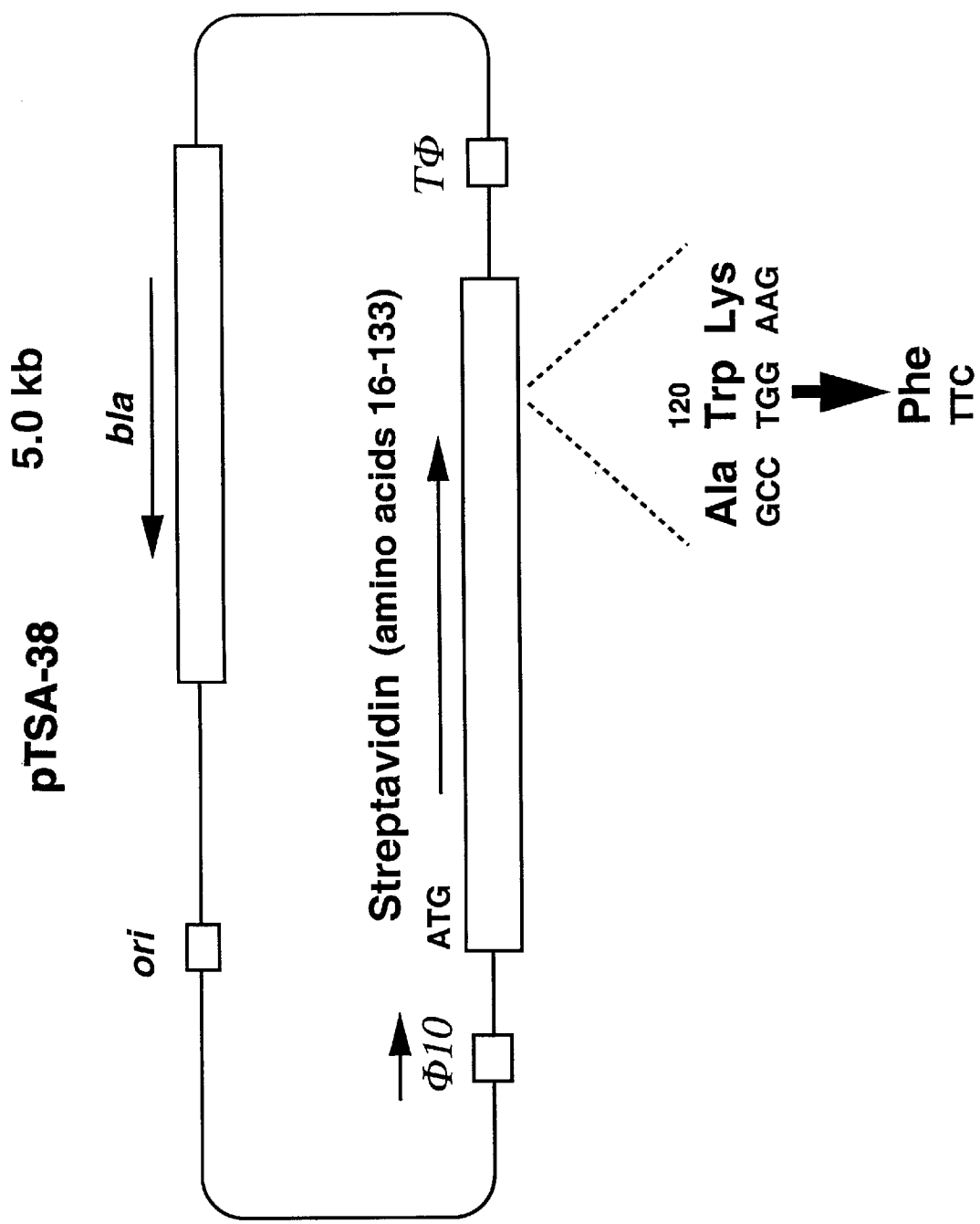
FIG. 1 Schematic of expression vector for a streptavidin mutant with a reduced binding affinity.

As embodied and broadly described herein, the present invention is directed to streptavidin proteins and peptides, to nucleic acid sequences which encode these streptavidins, to recombinant cells which contain these sequences, to methods for detecting and isolating small molecules, macromolecules and cells with streptavidin and to kits which contain streptavidin proteins and peptides.

The streptavidin-biotin binding system is an established fixture in biology due, at least in part, to the ability of streptavidin to non-covalently interact with biotin. This association is highly specific and quite strong with a binding constant of greater than 1015 M-l. However, it is precisely this extremely tight binding which limits the usefulness of conventional streptavidin-biotin systems. Although molecules and cells can be isolated from complex mixtures, removal of one or the other of the binding partners is nearly impossible. Dissociation can only be accomplished under very harsh conditions such as 6–8 M guanidine-HCl, pH 1.5. Not surprisingly, such conditions also denature, and thereby inactivate or destroy most target biological substances.

It has been discovered that streptavidin protein can be mutated in various ways to achieve a product that possesses altered physical parameters such as altered physical stability or an increased or decreased affinity for biotin. One such type of streptavidin protein contains a stabilized tetrameric protein. Stabilized streptavidin proteins have increased stability compared to normal, wild-type streptavidin while possessing a complete or even enhanced wild-type biotin-binding ability. These streptavidin proteins expand the well-known utility of streptavidin in detection, identification, separation and isolation technologies, and also allow for the use of streptavidin proteins in medical and other pharmaceutical procedures.

One embodiment of the invention is directed to streptavidin proteins having a greater stability than normal, wild-type streptavidin. Most substitutions, deletions or additions of amino acids in the 159 amino acid sequence of streptavidin are unstable. The resulting streptavidin protein is improperly folded or simply unable to fold forming aggregates that precipitate out of solution. Often, the protein is also unable to efficiently bind biotin. Surprisingly, a few mutations were discovered that are more stable than natural streptavidin. Increased stability indicates that the protein retains biotin under harsher conditions (e.g. increased temperatures and/or concentrations of denaturing agents), than wild-type streptavidin. Many of these stable streptavidin proteins are also substantially soluble in aqueous and other solutions. Substantial solubility indicates that the protein is nearly or as soluble as wild-type streptavidin in solutions such as, for example, ammonium sulfate at most concentrations and in up to 80% ethanol.

Many stable streptavidin proteins also remain associated with biotin under conditions which would cause dissociation of biotin from wild-type streptavidin. For example, core streptavidin peptides of the invention form macromolecules of protein that have a higher affinity for biotin than natural streptavidin or even natural core streptavidin (containing the amino acid sequence of streptavidin from positions 13 to 139). Natural core binds to about 0.94 to about 0.96 molecules of biotin per subunit of streptavidin and pH 7.4 At 6 M guanidine hydrochloride, pH 7.4, full-length and natural core streptavidin show about a 20% reduction in biotin binding (about 0.768 molecules biotin per subunit). At 4 M guanidine hydrochloride, pH 1.5, these same proteins show about a 15% reduction in biotin-binding affinity (about 0.826 molecules biotin per subunit). In contrast, Stv-13, a core streptavidin peptide (containing the amino acid sequence from 16 to 133) that forms tetrameric protein, shows no significant reduction in biotin-binding. This stability may be due to the absence of two charged residues from the core (Glu 14 and Lys 134) as well as two polar residues (Ser 136 and Ser 139). Furthermore, at 6 M guanidine hydrochloride, pH 1.5, natural core retains only about 20% of its normal biotin-binding capability whereas Stv-13 retains over about 80%. Preferably, stable streptavidin proteins bind to at least about 0.80 molecules of biotin per subunit at 6 M guanidine, pH 7.4, and more preferably at least about 0.9 molecules of biotin per subunit at 6 M guanidine, pH 7.4. It is also preferable that stable proteins bind to 0.8 molecules of biotin per subunit at 6 M guanidine, pH 7.4, and 0.7 molecules of biotin per subunit at 6 M guanidine, pH 7.4. This enhanced binding to biotin may be due to the lack of steric hinderance caused by the presence of the amino and/or carboxyl terminal sequences. Neither of these sequences appear to be necessary for binding, but in fact may have in some way interfered with biotin binding.

Streptavidin proteins of the invention may have an increased solubility in aqueous solutions. A streptavidin peptide comprising at least most of the amino acid sequence of streptavidin from about positions 21 to 130 with a deletion of the sequence from about positions 113 to 120 is both more stable and more soluble in aqueous solutions as compared to wild-type streptavidin. Streptavidin proteins containing the deletion of residues 113 to 120 also can form streptavidin dimers in solution. These dimers can form both homotetramers with other similar dimers, other heterotetramers with other streptavidin protein chains. Hybrid proteins have increased stability and an altered affinity for biotin.

Another streptavidin protein of the invention contains one or more cysteine residues attached to a terminus of the protein. The cysteine stretch preferably comprises 2, 3, 4, 5 or more, and more preferably 5 cysteine residues. The resulting protein chain can form dimers, trimers and tetramers in solution, or multimers with other streptavidin chains (hybrids). These proteins also have a reduced affinity for biotin. Streptavidin proteins with cysteine tails can be conjugated to other thiol groups, such as on a thiolated surface, to facilitate binding to the surface.

Another embodiment of the invention is directed to streptavidin proteins comprising at least most of the amino acid sequence of streptavidin from positions 21 to 130 wherein position 127 has been substituted with a lysine or an aspartic acid. Streptavidin proteins may consist of two or four subunits, or peptide chains, that form one or two domains, respectively. Chains may be full-length streptavidin or core streptavidin peptides consisting essentially of at least most of the amino acid sequence of streptavidin from position 13 to 139, 14 to 138 or 16 to 133. These dimeric and tetrameric proteins are very stable and may have an increased or stronger affinity for biotin than natural streptavidin.

For example, hybrid tetrameric streptavidin proteins containing four core streptavidin peptides, two with aspartic acid and two with lysine at position 127, retain biotin more strongly than natural biotin under harsh conditions. Experiments show that at increased temperatures, both wild-type and natural core streptavidin loose biotin binding ability more quickly with increased temperatures. These streptavidin protein retains greater than about 90% of bound biotin at 60° C., preferably greater than about 80% of bound biotin at 60° C., and more preferably greater than about 50% of bound biotin at 80° C. Streptavidin protein with increased affinity for biotin may have a binding affinity of greater than about $10^{12}$ $M^{-1}$ or about $10^{14}$ $M^{-1}$, preferably greater than about $10^{15}$ $M^{-1}$, and more preferably greater than about $10^{16}$ $M^{-1}$.

Another embodiment of the invention is a streptavidin peptide wherein the histidine at position 127 is replaced with a cysteine. Streptavidin protein comprising these peptide chains can form reversible and irreversibly cross-lined tetramers in solution. Cysteine resides can be covalently linked by treating the streptavidin protein with an oxidizing agent, such as hydrogen peroxide, or by removing reducing agents such as 2-mercaptoethanol or DTT. A very high percentage of sulfhydryl bonds are cross-linked (greater than about 90%) forming a stable tetramer. Disulfide bonds can also be reduced by adding reducing agents making the process fully reversible in both directions. Alternatively, sulfhydryl bonds can be irreversible cross-linked by treating the protein with a cross-linking agent such as 1,3-dibromoacetone. The resulting cross-linked streptavidin tetramer is more stable than wild-type streptavidin with an increased affinity for biotin.

Another embodiment of the invention is directed to streptavidin proteins which are subjected to a cross-linking agent. Cross-linking can occur within and between subunits and domains. Surprisingly, it has been determined that domain stability directly correlates with biotin binding. Streptavidin proteins with increased domain—domain stability also have an increased affinity for biotin. These stable tetrameric streptavidin proteins can be formed by treating streptavidin of the invention with a cross-linking agent such as 1,3-dibromoacetone, bissulfo(succinimidyl)suberate, dimethyladipimidate, disuccinimidyl glutarate, n-hydroxysuccinimidyl 2,3-dibromopropionate or 1-ethyl-3-[3-(dimethylamino)propyl]-carbodiimide. Preferably, the cross-linking agent is an amino-specific, homobifunctional cross-linker.

Streptavidin proteins which can cross-link include, for example, streptavidins containing a cysteine residue at position 127. These residues can be irreversibly cross-linked by treatment with, for example, 1,3-dibromoacetone. Other examples of streptavidins of the invention include heterotetramers such as proteins having chains with lysine and aspartic acid residues at position 127. The resulting streptavidin tetramer protein has increased stability and retains more biotin than wild-type streptavidin under harsh conditions such as increased temperature. This would be very useful in binding studies that require high temperature interactions.

Another embodiment of the invention is directed to a reduced-affinity streptavidin protein. This protein has a substantially lower binding constant for biotin than wild-type streptavidin and comprises an amino acid sequence of streptavidin containing one or more deletions, insertions, point mutations or combinations of these genetic alterations that alter, but maintain the biotin-binding site. The peptide sequence may be a full length streptavidin or an amino acid sequence substantially equivalent to streptavidin. A protein substantially equivalent to streptavidin includes a core streptavidin having the wild-type streptavidin amino acids from about positions 13 to 140, or a reduced-core streptavidin having the wild type streptavidin amino acids from about positions 16 to 133. Other amino acids of streptavidin may be changed without altering the defming characteristic of the reduced-affinity streptavidin.

The streptavidin amino acid sequence of the reduced-affinity protein of the invention may be continuous or fragmented such as, for example, when the protein contains point mutations. Preferably, the protein comprises an amino acid sequence which largely corresponds to the core region of wild-type streptavidin. In the reduced-affinity protein, this region also contains the substitutions or deletion that confer reduced affinity.

One type of reduced-affinity streptavidin protein comprises a core sequence of streptavidin protein wherein one or more of the residues between about position 79 to about position 120 has been substituted or deleted. Within this region are four tryptophans of position 79, 92, 108 and 120, and two tryptophan-lysine pairs (79–80 and 120–121). These sites are extremely hydrophobic and contribute to the biotin binding site. Substitution of, for example, one or more of the tryptophan or lysine residues (or pairs) with an amino acid which is still hydrophobic, but less hydrophobic than tryptophan or lysine, respectively, reduces the affinity of this protein for biotin without destroying the binding site altogether. Amino acids which may be substituted for tryptophan or lysine include methionine, proline, isoleucine, leucine, valine, alanine, glycine, lysine (for tryptophan), phenylalanine, and derivatives and modifications of these amino acids (e.g.beta-alanine, N-ethylglycine, 3-hydroxyproline, 4-hydroxyproline, alloisoleucine, N-methylglycine, N-methylisoleucine, N-methylvaline, norleucine or norvaline). Preferably, the reduced-affinity streptavidin protein comprises a phenylalanine, phenylalanine derivative (e.g.4-amino-phenylalanine) or a phenylalanine modification (e.g.methylation) at position 79, 92,108 or 120, and preferably at positions 79 and 120.

Reduced-affinity streptavidin protein of the invention has a affinity for biotin of substantially less than wild-type streptavidin or streptavidin core protein. The affinity of these proteins may be less than about $10^{12}$ $M^{-1}$, preferably less than about $10^{10}$ $M^{-1}$, more preferably less than about $10^9$ $M^{-1}$, and even more preferably about $10^8$ $M^{-1}$. The lower limit of affinity is slightly greater than non-specific binding which can occur at about $10^6$ $M^{-1}$ or about $10^7$ $M^1$.

Another embodiment of the invention is directed to streptavidin proteins whose attachment to biotin can be disrupted more easily than the wild-type streptavidin-biotin bond. The streptavidin-biotin bond involving streptavidin proteins of the invention may be disrupted through the addition of fairly low concentration of biotin or biotin derivatives (biotin analogs) or modifications. The concentration of biotin which can be used to disrupt the streptavidin-biotin bond using streptavidin proteins of the invention is between about 0.1 mM to about 10 mM or, preferably, between about 0.3 mM to about 2 mM. In addition, elution may be performed in a high pH (e.g. 100 mM triethylamine, pH 11.5; 100 mM phosphate, pH 12.5), in a low pH (e.g. 100 mM glycine pH 4; 100 mM glycine pH 2.5; 100 mM glycine pH 1.8), in high salt (e.g. 5 M LiCl, 10 mM phosphate, pH 7.2; 3.5 M $MgCl_2$, 10 mM phosphate pH 7.2), or in the presence of ionic detergents (e.g. 1% SDS; 1% DOC), dissociating agents (e.g.2 M urea; 8 M urea; 2 M guanidine HCl), chaotropic agents (e.g.3 M thiocyanate), organic solvents (e.g. 10% dioxane; 50% ethylene glycol, pH 11.5; 50% ethylene glycol, pH 8), protease (protease K) or water. This type of versatility is a great advantage when utilizing conventional streptavidin-biotin detection or isolation procedures. Proteins are not destroyed and cells remain viable even after biotin has been removed.

Another embodiment of the invention is directed to streptavidin proteins bound to a solid support, for example, to facilitate detection and isolation procedures. Typical solid supports include the surfaces of plastic, glass, ceramics, silicone or metal. These components may be found in detection kits, biological sample analysis devices and environmental sampling aids. Particularly useful types of such components include beads (magnetic beads; Dynal), tubes, chips, resins, gels, membranes (e.g. porous membranes), monolayers, plates, wells, films, sticks or combinations of the surfaces. Solid supports also include hydrogels which may be made of a variety of polymers such as acrylamide and hydroxyapatite, or biomolecules such as dextran, cellulose or agarose.

Binding of streptavidin to surfaces may be accomplished in several ways. A solid support may be derivatized with a moiety which can form a covalent bond with streptavidin, avidin or biotin. Alternatively many commercially available surfaces may be used to couple streptavidin, avidin or biotin. Example of such surfaces include agarose, cross linked agarose, acrylamide, agarose and acrylamide combinations, polyacrylic, cellulose, nitrocellulose membranes, nylon membranes, silicon and metal. These surfaces may be further modified to contain a carboxyl or other reactive group for crosslinking. Reagents suitable for crosslinking to solid surfaces include cyanogen bromide, carbonyldiimidazole, glutaraldehyde, hydroxysuccinimide and tosyl chloride.

One type of streptavidin which may be used to facilitate coupling to a solid support is composed of a core streptavidin containing a plurality of cysteines at the protein's amino or carboxyl terminus, and preferably the carboxyl terminus. The cysteines facilitate binding to, for example, a thiolated support.

Streptavidin proteins of the invention may also be coupled to a biological agent such as an antibody, an antigen, a hormone, a cytokine, a cell or a pharmaceutical agent (for in vivo use). Cells may be eukaryotic such as mammalian cells, prokaryotic such as bacterial cells, insect cells, parasitic cells, fungal cells or yeast cells. Coupling may be through electrostatic interaction or by covalent modification of one or both coupling partners. Covalent modifications are fairly stable when, for example, the coupled agent is subjected to the a biological environment such as occurs on administration to a host such as a mammal.

Another embodiment of the invention is directed to nucleic acids which encode a streptavidin protein or peptide of the invention. Such nucleic acids may further comprise transcription or translational control regions to regulate transcription, translation or secretion of the recombinant protein. Control sequences can also be introduced to provide inducible expression. This is very useful as streptavidin is somewhat harmful to most cells. Recombinant nucleic acids may be introduced into bacterial cells, for example, by transformation, or into mammalian cells, for example, by transfection. Recombinant cells can be used to produce large quantities of recombinant protein as needed or to provide a continuous source of recombinant streptavidin to a biological system. Recombinant cells which can support the expression of streptavidin proteins or peptides on the invention include eukaryotic cells such as mammalian and yeast cells and prokaryotic cells such as bacteria.

In conventional streptavidin-biotin systems, there are many methods for detecting or purifying a given target. For example, the target may be directly biotinylated and complexed with the reduced substrate affinity streptavidin. Alternatively a binder that complexes with the target may be the biotinylated component. There may, in fact, be more than one binder involved in a given system. The detectable probe may be bound to the streptavidin and the system may involve more than one detectable probe. Both the target and the support may be biotinylated, and the two are complexed together with the reduced substrate affinity streptavidin. Many permutations are made possible by the variety of targets, binders and probes.

Another embodiment of the invention is directed to a method for detecting or purifying a target from a heterogeneous mixture which contains target. The target is biotinylated using biotin or a biotin derivative or modification appropriate for the target. Targets may be nearly any substance such as biological or inorganic substances. Biological substances include proteins and protein precursors, nucleic acids (DNA, RNA, PNA, aptomers) and nucleic acid precursors (nucleosides and nucleotides), carbohydrates, lipids such as lipid vesicles, cells, biological samples and pharmaceuticals. Typical proteins which are detectable in conventional streptavidin/biotin systems, and useful herein, include cytokines, hormones, surface receptors, antigens, antibodies, enzymes, growth factors, recombinant proteins, toxins, and fragments and combinations thereof.

Subcellular components may also be purified by linking a ligand, with an affinity to the component, to a streptavidin of the invention. Proteins which can be purified include cell adhesion molecules, antibody antigens, receptors ligands and antibodies. Specific affmnity adsorbent moieties, such as wheat germ agglutinant, anti-idiotypic antibodies and dye ligands may be coupled to streptavidin to isolate glycosylated proteins such as SP1 transcription factor, dye binding proteins such as pyruvate kinase and liver alcohol dehydrogenase, and other antibodies. Using this method, cellular and subcellular organelles may be rapidly purified using specific antibodies.

The heterogenous mixture is contacted to the reduced-affinity streptavidin which may be fixed to a surface of a support of free in solution. Mixture is removed or the support removed from the mixture and the target purified. Alternatively, target may be coupled to streptavidin and biotin attached to the support. In either situation, the result is the same. However, using reduced-affinity streptavidin coupled to target, target may isolated free of any biotin.

Alternatively, when it is not as important to separate streptavidin or biotin from the purified target, a streptavidin with increased affinity for biotin may be used. This may be useful, for example, where the targeted substance is a contaminant. Increased affinity streptavidin is especially useful if the targeted substance is a trace contaminant. The contaminant may be removed by the increased affinity streptavidin and disposed of. The increased affinity will ensure a more complete recovery than wildtype streptavidin. Because wildtype streptavidin is unstable under the extremes conditions of pH, salt, detergent, and disrupting agents, it is necessary to neutrlize these agents before separation with streptavidin. Increased affinity streptavidin may reduce or eliminate the need for neutralization. This reduction or elimination will reduce processing time and complexity and contribute directly to cost reduction.

Using the methods disclosed herein, combination of detection and isolation procedures can also be utilized. For example, targets can be transferred from one support to another using a manual or automated apparatus. Sequential detection or purification techniques can also be used to purify targets to homogeneity. Such techniques were heretofore not possible when the streptavidin biotin bond could not be easily broken. In addition, nearly any conventional detection or isolation methodology can be performed with conventional streptavidin-biotin procedures.

Another embodiment of the invention is directed to a method for the detection of a disorder in a patient such as a human. Reduced-affinity streptavidin is naturally targeted to biotin. Biotinylation of a site within the body of the patient, such as, for example, using monoclonal or polyclonal antibodies coupled with biotin and specific for the site will target the coupled complex to that site. Reduced-affinity streptavidin may be coupled with a pharmaceutical which can be used to treat the disorder. Treatable disorders include neoplasms, genetic diseases and infections (e.g. viral, parasitic, bacterial, fungal).

Another embodiment of the invention is directed to a method for the isolation and culture of infectious agents from a patient. Body fluids, such as blood of a patient may be contacted with a support with antibodies specific for viral surface antigens. If the antibody was crosslinked to the solid support by a reduced-affinity streptavidin, bound infectious agents may be released without harm with a gentle elution technique. The isolated agents may be definitively identified by live culture. Infectious agents which can be isolated by this technique include slow viruses, malaria and infectious yeast.

Another embodiment of the invention is directed to a purification method for nucleic acids and nucleic acid-protein complexes. Nucleic acids can be immobilized to a column through a reduced affinity streptavidin complex. The immobilized nucleic acid may be single or double stranded and it may comprised cloned sequence or random sequence. The column may be used to enrich for nucleic acid-binding proteins. The proteins bound to nucleic acids may be released without the use of nuclease or protease. The product may be studied, without the disruption of the protein nucleic acid bond by native gel electrophoresis (a gel mobility shift assay). This is an especially powerful tool for studying proteins with relatively low affinity for nucleic acids such as transcription factors.

Another embodiment of the invention is directed to methods for using reduced affinity streptavidin to sort cells. Current methods of cell sorting requires a fluorescent activated cell sorter which involves considerable expense and the use of fluorescent dyes which are quite toxic to the cells. Beads and plates coated with antibodies specific for cell surface receptors may can be used to collect cells, but due to the high affinity, the recovery of live cells are generally not feasible. To enhance live release, a reduced affinity antibody may be used, but such antibodies also reduce yield. There are many condition where the recovery of live cells is desirable such as in the isolation of hemopoietic stem cells for bone marrow transplants, and the collection of platelet from whole blood for chemotherapy patients. In these situations the reduced affinity streptavidin may be employed to reversibly link antibodies to a surface and the bound cells can be release under non-lethal condition. The released cells may be used directly to treat patients, or the cells can be used as input to further rounds of purification. In addition to antibodies, any moiety which binds tightly to cell surface antigens such as cell adhesion molecules, receptors and, mediators may also be used.

Another embodiment of the invention is directed to the production of macromolecular arrays on solid surfaces using the reduced substrate affinity streptavidin-biotin complex. With reversible complex formation, surface biotinylated probes could be regenerated or changed, as desired, without the use of harsh conditions. This allows the full automation of this, and other, streptavidin application. The reduced substrate affinity streptavidin could also be fused to partner proteins to produce chimeras, in which the streptavidin moiety provides tight, yet reversible binding of the partners to biotin, biotin derivatives, and biotinylated macromolecules. This allows for additional purification and detection techniques, all of which can be fully automated. Thus, reduced substrate affinity streptavidin should be able to serve as a unique biotechnology tool and offer novel applications, in which irreversible biotin-binding by natural streptavidin under the conditions usable with biological materials is undesirable.

Another embodiment of the invention is directed to the production of macromolecular arrays on surfaces with increased affinity streptavidin. Macromolecular arrays produced with increased affinity streptavidins may be sterilized and washed under more extreme conditions than arrays produced with normal affinity streptavidin. The more stringent washes can produce an array with higher accuracy, smaller dimensions, and with reduced background. In addition, increased affinity streptavidin will allow the recycling of macromolecular arrays by washing.

Another embodiment of the invention is directed to methods using macromolecular arrays comprising increased affinity streptavidin under extreme conditions. The increased affinity of the streptavidin bond will allow placements of the macromolecular arrays comprising these bonds in conditions which are previously not suitable. Examples of these conditions may include, for example, in a delivery pipeline, in chemical and biological reactors, in high temperature reactors, and in environmental monitoring. The stable increased affinity streptavidin bond may also be useful in methods where it is inconvenient to replaced failed monitors. Examples of methods where replacement of macromolecular array may be inconvenient include, for example, in vivo or in vitro monitoring of life processes, remote monitoring, medical implants, and monitoring of microscopic processes, and monitoring the interior of a continuous chemical or biological process. Examples of continuous chemical or biological processes include continuous chemical and biological productions where replacement of the macromolecular array necessitates the cessation of the process. The use of an increased affinity streptavidin will reduce or eliminate expenses related to the shutdown of a continuous process.

Another embodiment of the invention is directed to methods for using a streptavidin molecule with increased binding ability. With increased stability streptavidin and biotin may be used in applications not suitable for wildtype streptavidins. Applications which may benefit from increased stability streptavidin include microscopic machine, equipment and assays which must be sterilized, and biofabrication. The production of macromolecular arrays on inert substrates such as silicon or paper involving processes comprising heat, pressure, organic solvents, extremes of pH under sterilizing and sterile conditions is possible using streptavidin with increasing biotin binding ability.

One specific example of how an increased biotin binding streptavidin may be used is in the manufacturer of dipsticks for bioassays. A dipstick may comprise a support such as plastic or paper on which are attached reagents such as immunoreagents. Dipsticks intended to be used in a sterile environment such as an operating room has to be manufactured sterilely. If a dipstick comprises a streptavidin biotin bond, sterilization is difficult because sterilizers may inactivate the streptavidin biotin bond. A dipstick comprising increased affinity streptavidin may be manufactured with reduced cost because of the streptavidin's ability to withstand routine sterilization.

Another embodiment of the invention is directed to methods for using increase affinity streptavidin in environments which can cause the premature disruption of the streptavidin-biotin bonds. Examples of applications which can disrupt a wild-type streptavidin biotin bond include, for example, monitoring bioreactors or chemical reactors under high temperature, high pressure, high solvent, high salt, or extreme pH conditions. It may be desirable, for example, to directly monitor a chemical synthesis reaction using an assay or kit comprising increased affinity streptavidin without first reducing the temperature, pressure or pH of the reaction.

Another advantage of increased affinity streptavidin is in reduced product storage cost. It is desirable for many assays and kits to have low price and increased stability. However, many assays and kits, because of the sensitivity of their components, have short shelf lives and strict storage and shipping requirements. These strict storage and shipping requirements increase the cost and limit the availability of these products. Assays and kits comprising increased affinity streptavidin, because of the additional stability, may have a longer shelf and may be less fastidious in shipping and storage requirements. The enhanced stability of these assays and kits will reduce the cost to the consumer.

Another embodiment of the invention is directed to kits which contain reduced-affinity streptavidin for the detection or isolation of targets, such as substances which may be indicative of a disorder. Disorders which can be detected include infection, neoplastic disorders and genetic defects. Kits may also comprise additional reagents which may be utilize in the detection process.

The following experiments are offered to illustrate embodiments of the invention, and should not be viewed as limiting the scope of the invention.

EXAMPLES

Example 1
Oligonucleotide Directed Mutagenesis of Streptavidin.

To disrupt the inter-subunit hydrophobic contact made by, for example, Trp-120 to biotin without disturbing local environments around this residue, the codon encoding Trp-120 was mutated to a codon encoding phenylalanine. Because of its smaller size, the phenylalanine residue of one subunit should have a considerably reduced hydrophobic interaction, if any, with the alkyl moiety of the pentanoyl group of biotin bound by an adjacent subunit. If no local conformational changes occurred as a result of this mutation, the minimal distance between the phenyl group of this phenylalanine residue and the alkyl chain of biotin should be approximately 5.1 Å. This distance is significantly greater than that between Trp-120 and biotin (4.1 Å) in wild-type streptavidin. However, because of the hydrophobicity of phenylalanine, the conversion to Phe-120 should have minimal effects on the local hydrophobic environments around the biotin-binding sites and the dimer—dimer interface.

pTSA-13, which carries the coding sequence for amino acids 16–133 of mature streptavidin was used as the starting material to make reduced affinity streptavidin (FIG. 1). Basically, a phosphoxylated oligonucleotide of the sequence 5'-d(ACCAGCGTGGACTT GAAGGCGTTGGCCTCG)-3' (SEQ ID NO 2) was used to mutate the codon TGG encoding for Trp on residue 120 to TTC. The new codon TTC, codes for Phe at position 120. Briefly, the reaction was initiated by hybridizing 10 pmoles of the phosphorylated oligonucleotide to the single stranded streptavidin DNA in a 10 µl reaction with 20 mM Tris-HCl, pH 7.5, 10 mM $MgCl_2$, 50 mM NaCl and 1 mM dithiothreitol (DTT). Elongation and mutation was initiated by the addition of 10 µl of 20 mM Tris-HCl, pH 7.5,10 mM $MgCl_2$, 10 mM DTT, 2 mM dATP, 2 mM dTTP, 2 mM dCTP, 2 mM dGTP, 10 mM ATP, 5 units bacteriophage T4 DNA ligase and 2.5 units of Klenow. This procedure was performed according to the in vitro mutagenesis kit supplied by Amersham. Subsequent procedures followed as recommended by Amersham. Resulting products created were used to transform competent E. coli cells. To select clones contained the desired mutations, the sequence was confirmed using a dideoxy chain termination procedure.

Example 2
Production of Phe-120 Streptavidin in E. coli.

The mutated streptavidin of Example 1 was used to produce large quantities Phe-120 streptavidin protein. Because the expression of streptavidin in bacteria has a lethal effect to a cell, an inducible system was used. The DNA fragment comprising the sequence encoding the streptavidin mutant was excised from its vector with the restriction endonucleases Nde I and BamH I, and cloned into the same sites in the T7 expression vector pET-3a. Resultant plasmids were transformed in BL21(DE3) (pLysE) bacteria.

To produce the Phe-120 streptavidin, BL21(DE3)(pLysE) cells carrying the expression plasmid were grown at 37° C. in LB supplemented with 0.4% glucose, 150 µg/ml ampicillin and 25 µg/ml chloramphenicol until cultures reach a density of 0.6 at $A_{600}$. Expression of the Phe-120 streptavidin was induced by the addition of a gratuitous inducer, IPTG, to a final concentration of 0.4 mM. Phe-120 streptavidin was expressed for five hours at 37° C. before the cells were harvested.

Example 3
Purification of Expressed Phe-120 Streptavidin.

Phe-120 streptavidin protein produced by induced E. coli was purified. Cells expressing the mutant streptavidin were harvested by centrifugation at 1600×g for 10 minutes. Protein was purified from the insoluble fraction of cell extracts. Briefly, cells were pelleted, washed with an isotonic solution of 100 mM NaCl, 1 mM EDTA and 10 mM Tris, pH 8.0, and resuspended in a detergent solution of 2 mM EDTA, 30 mM Tris-HCl, pH 8.0, 0.1% Triton X-100. Lysis occurred under these conditions because the presence of T7 lysozyme in the cells.

Nucleic acid in the extract was digested for 15 minutes at room temperature by the addition of $MgSO_4$, DNase I and RNase A, to final concentrations of 12 mM, 10 μg/ml and 10 μg/ml, respectively. The insoluble fraction of the extract containing Phe-120 streptavidin was isolated by centrifugation of the nuclease treated extract at 39,000×g for 15 minutes. Pellets were washed with 2 mM EDTA, 30 mM Tris-HCl, pH 8.0, and 0.1% Triton X-100, and solubilized in 6 M guanidine hydrochloride, pH 1.5.

Impurities were removed by dialysis against 6 M guanidine hydrochloride pH 1.5. Mutant streptavidin was renatured slowly by dialysis against 0.2 M ammonium acetate, pH 6. After renaturation, insoluble impurities were removed by centrifugation at 39,000×g. Supernatant containing the mutant streptavidin protein was removed and collected. Final purifications were performed by 2-iminobiotin affinity chromatography.

Example 4
General Characteristics of the Phe-120 Streptavidin.

Figure 2A:
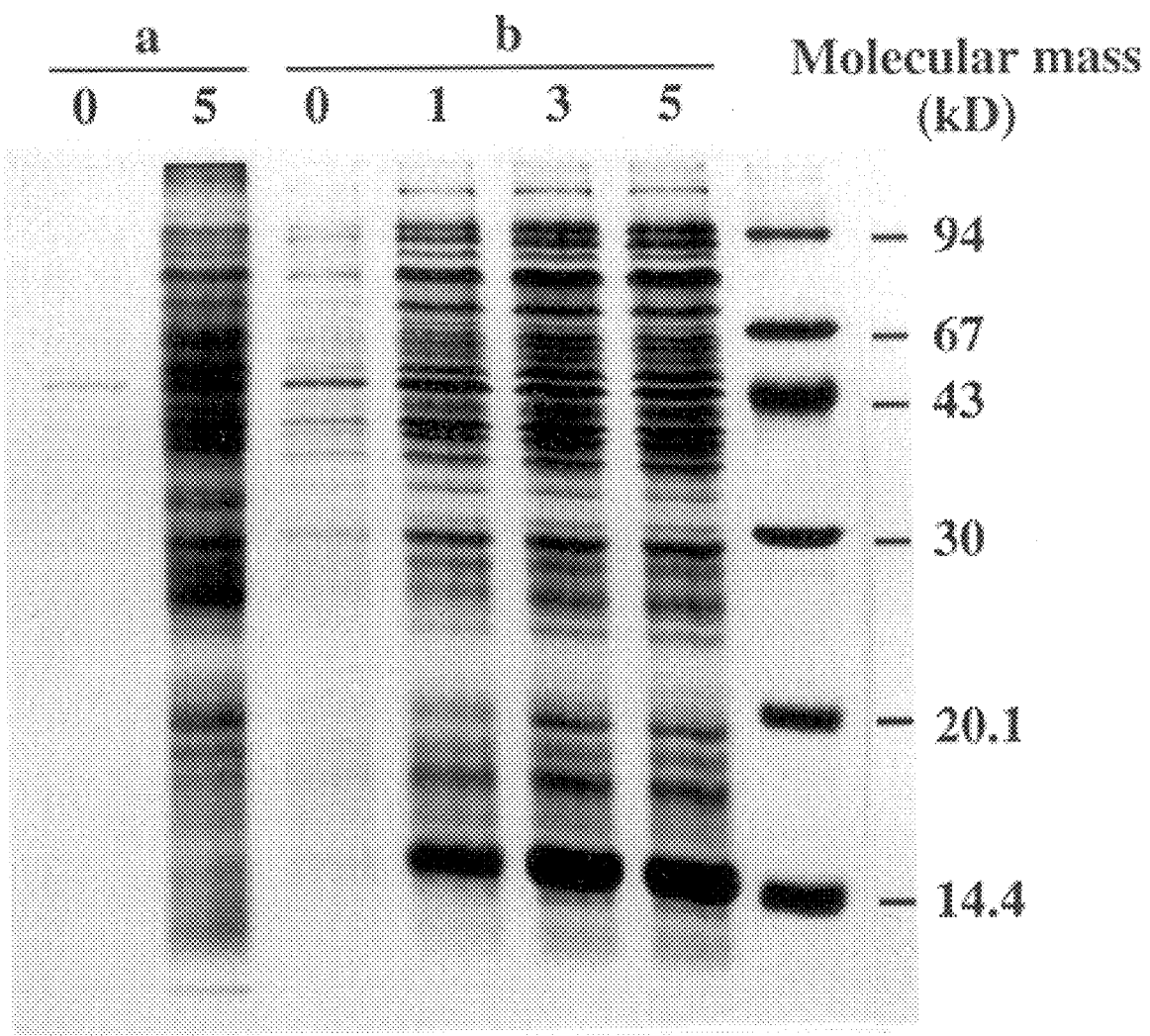
FIGS. 2A and 2B SDS gel of electrophoresis pattern observed from (2A) expression vector pTSA-38; and (2B) purified pTSA-38 expression product.

Polyacrylamide gel electrophoresis analysis (PAGE-SDS) of Phe-120 streptavidin was performed on protein expressed in *E. coli* carrying pTSA-38. Total cell protein of BL21 (DE3)(pLysE), with or without pTSA-38, was analyzed using a 15% polyacrylamide gel. As shown in FIG. 2A, lanes "a"=BL21(DE3)(pLysE) and lanes "b"=BL21 (DE3) (pLysE)(pTSA-38), streptavidin protein could be easily visualized upon staining. The number above each lane is the time in hours after induction. Each lane contained total cell protein from the following volume of culture. At 0 hour for "a" and, at 0 hour and 1 hour for "b",50 μl; at 3 hours and 5 hours for "b",33 μl; and at 5 hours for "a",25 μl. The right lane contains molecular mass standard proteins.

Figure 2B:
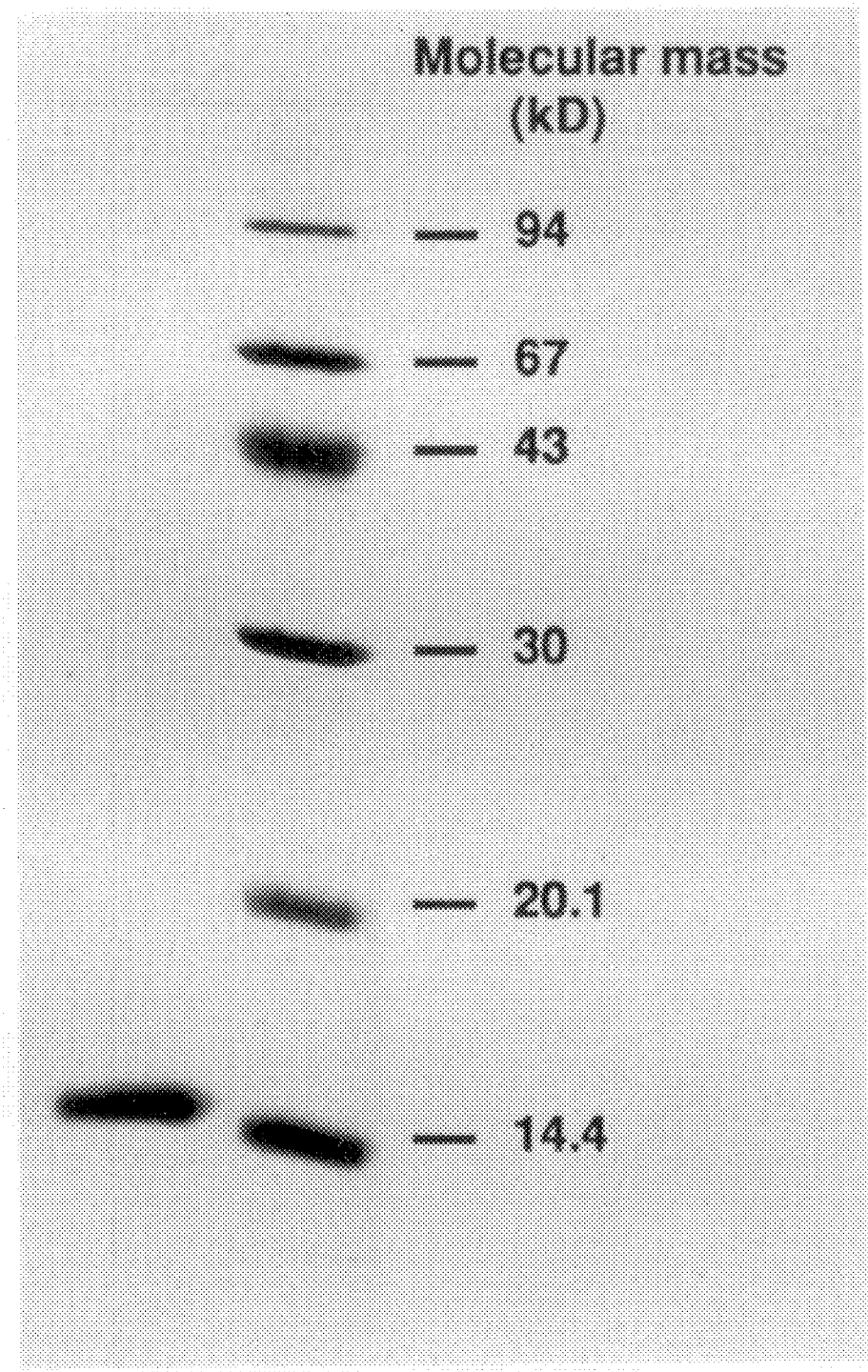

Purified Phe-120 streptavidin was also analyzed by SDS-PAGE. Briefly, approximately 3 μg of purified Phe-120 streptavidin was applied to a 15% polyacrylamide gel (FIG. 2B). The right lane contains molecular mass standard proteins. The molecular weight of Stv-38 was estimated to be approximately 13,000 daltons, which is consistent with the molecular mass obtained from the deduced amino acid sequence (12,600 daltons).

Figure 3A:
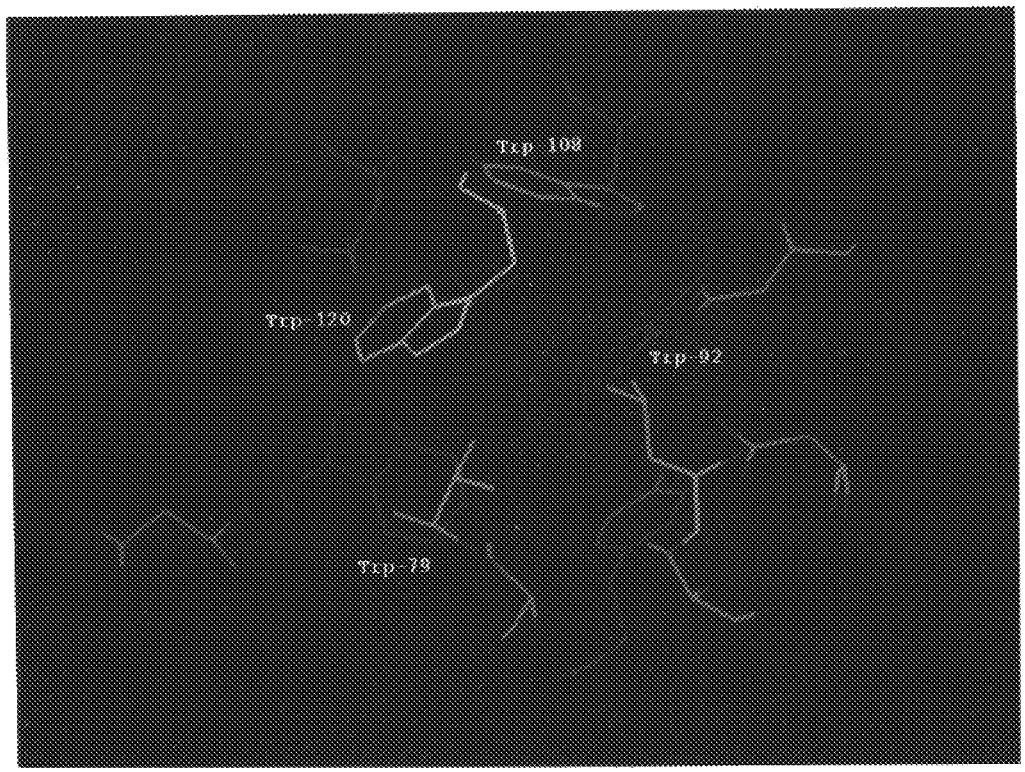
FIGS. 3A and 3B Local structures around the biotin-binding site of (3A) natural streptavidin and (3B) reduced-affinity streptavidin protein.
Figure 3B:
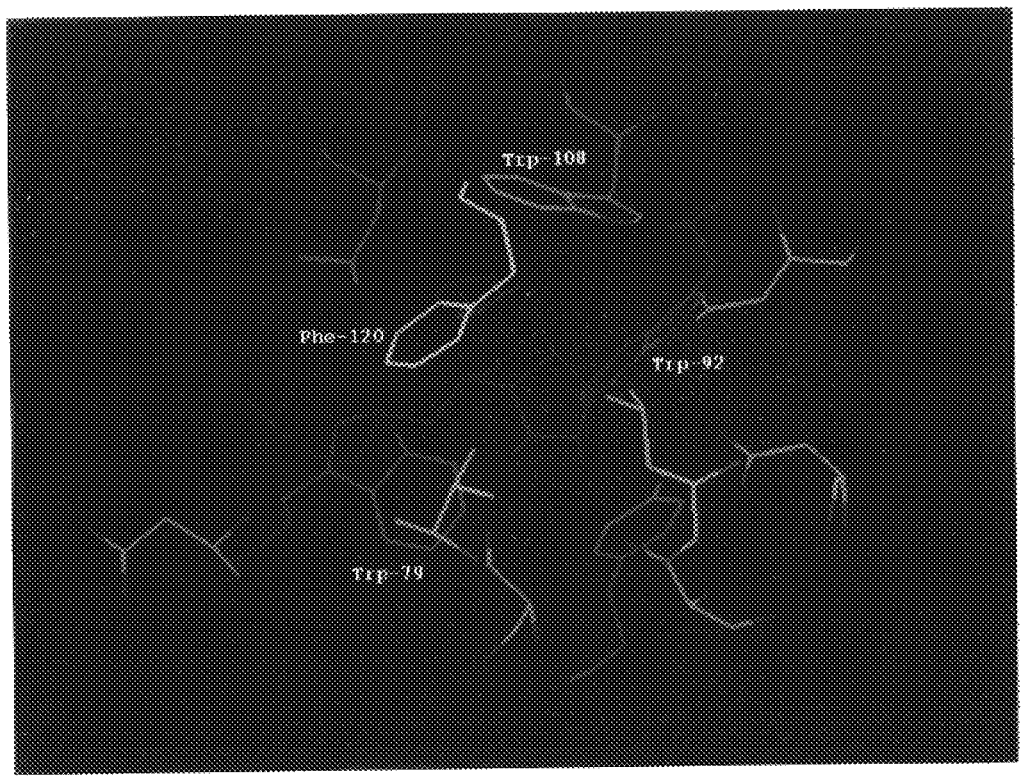

Local structures around the biotin-binding site of natural or wild-type streptavidin are shown in FIG. 3A. FIG. 3B shows the biotin-binding site of the reduced-affinity streptavidin of Stv-38 in which Trp-120 is converted to Phe. Bound biotin is colored red. These structures are drawn based on the known three-dimensional structure of natural streptavidin. The positions of the four Trp residues (Trp-79, -92, 108 and -120) are indicated. Note that Trp-79, -92 and -108 are of one subunit with biotin, while Trp-120 (yellow) or Phe-120 (yellow) is provided by an adjacent subunit through the dimer—dimer interface. Carbon, nitrogen, and oxygen atoms are colored green, blue and red, respectively.

Example 5
Biotin Binding of Phe-120 Streptavidin.

On gel filtration chromatography using a Superdex 75 HR 10/30 column the molecular mass of purified Phe-120 streptavidin was estimated to be 49,000 daltons, consistent with proper tetramer formation. When the biotin binding Phe-120 streptavidin was analyzed, biotin was found at an amount of greater than 0.97 molecules of biotin per streptavidin subunit. This degree of binding is consistent with full biotin-binding ability. These results indicate that Phe-120 streptavidin forms a tetramer as does wild type streptavidin and that the conversion of Trp-120 to Phe-120 has no significant effect on the basic properties of the mutant streptavidin. These data also indicate that the mutation had minimal effects on local environments around the biotin-binding sites and the dimer—dimer interface, thus allowing the correct folding of the molecule.

Example 6
Determining the Biotin-Binding Affinity of the Phe-120 Streptavidin.

The biotin-binding affinities of wild type and Phe-120 streptavidin were determined by an equilibrium dialysis method using a micro dialyzer (Hoeffer Scientific). One hundred microliters each of D-[carbonyl-$^{14}$C] biotin (2 nM–4 μM; 53 mCi/mmol; Amersham) and 100 μl of streptavidin (5.3 μg/ml, 0.42 μM subunits) were prepared separately in TBS (150 mM NaCl, 20 mM Tris-HCl, pH 7.4, 0.02% $NaN_3$) solutions. Equilibrium dialysis analysis was begun by the placement of the two solutions into two opposing chambers of a micro dialyzer. Chambers were incubated at 30° C. with rotation for 48 hours and the concentration of labeled biotin in each chamber was measured by scintillation counting. Results were plotted on a Scatchard plot. The apparent biotin-binding affinity of the Phe-120 streptavidin was determined to be from about $1-3\times10^8$ $M^{-1}$ demonstrating the reduced substrate affinity of this streptavidin mutant.

Comparison with the biotin-binding affinity of natural core streptavidin ($4\times10^{14}$ $M^{-1}$ at pH 7.0 at 25° C.) indicated that a substantial reduction in the biotin-binding affinity was caused by the mutation of Trp-120 to Phe. This indicated that the hydrophobic contact made by Trp-120 to biotin contributed significantly to the extremely tight biotin-binding by streptavidin. Disruption of the hydrophobic contact made by Trp-120 to biotin may not be solely responsible for the drastic reduction in biotin-binding affinity. The mutation of Trp-120 to Phe-120 may have generated additional structural changes in or around the biotin-binding site which also lowered the biotin-binding affinity.

Example 7
Determination of Biotin-Binding Stability.

To determine if the mutation affected the biotin-binding stability of streptavidin, stability was determined by monitoring the release of radioactive biotin in the presence of free biotin at neutral pH. Purified Phe-120 streptavidin was saturated with D-[carbonyl-$^{14}$C] biotin in 150 mM NaCl, 20 mM Tris-HCl, pH 7.4,0.2 mM $NaN_3$. Stv-38 was mixed with D-[carbonyl-$^{14}$C]biotin at a molar ratio of biotin to biotin-binding site of 1. This Stv-38 solution (1.71 μg, 136 nmol subunits in 133 μl of TBS) was mixed with an equal volume (133 μl) of TBS containing various concentrations of free biotin. The mixture was allowed to stand at 21° C. for 20 minutes, transferred to a Ultrafee MC filter (molecular mass cut off, 10 kD), and centrifuged at 1,600×g for 10 minutes.

Stability of the biotin-bond was measured by counting the amounts of released radioactive biotin in the filtrate. The amount of radioactivity in the filtrates was determined by liquid scintillation counting, and plotted as a function of the final concentration of free biotin added (FIG. 4; closed square), and the amount of natural core streptavidin analyzed in the same manner as the control (FIG. 4; open circle).

Figure 4:
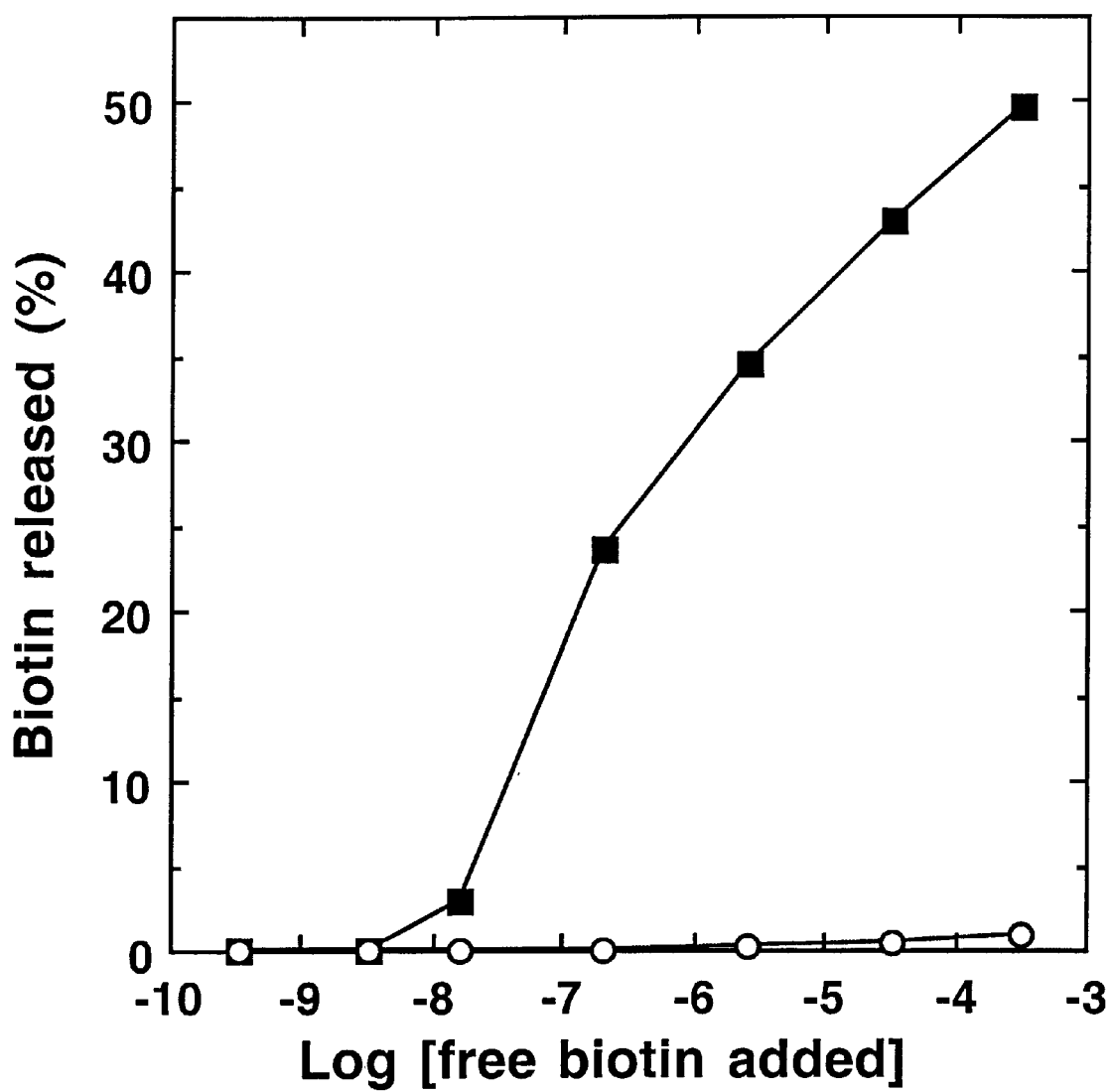
FIG. 4 Graph showing release of biotin from reduced-affinity streptavidin protein in relation to increased amounts of added free biotin.

As shown in FIG. 4, the amount of released $^{14}$C-labeled biotin increased as the concentration of free biotin was raised above 33 nM. Addition of 330 μM free biotin released approximately 50% of the bound $^{14}$C-labeled biotin from Phe-120 streptavidin. In contrast, almost no release of bound biotin was observed with natural core streptavidin by the addition of free biotin up to 330 μM.

These results demonstrated that Phe-120 streptavidin retains bound biotin stably even under relatively harsh conditions. However, the addition of free biotin (e.g. about 0.1 to about 10 mM and preferably about 0.3 to about 2 mM) resulted in the dissociation of previously bound biotin from the mutant due, presumably, to exchange of bound biotin with free biotin.

In the three-dimensional structure of streptavidin, Trp-120 spatially covers the pentanoyl group of bound biotin. This apparently contributes to the very low dissociation rate constant for streptavidin-biotin complexes ($2.8 \times 10^{-6}$ sec$^{-1}$ at pH 7 at 25° C.). It is quite likely that the mutation of Trp-120 to Phe-120 led to the greater rate constant for the dissociation of bound biotin with minimal effects on the association rate constant, thereby enhancing exchange reactions with free biotin.

Example 8
Effect of Biotin Binding on Subunit Association.

Figure 5:
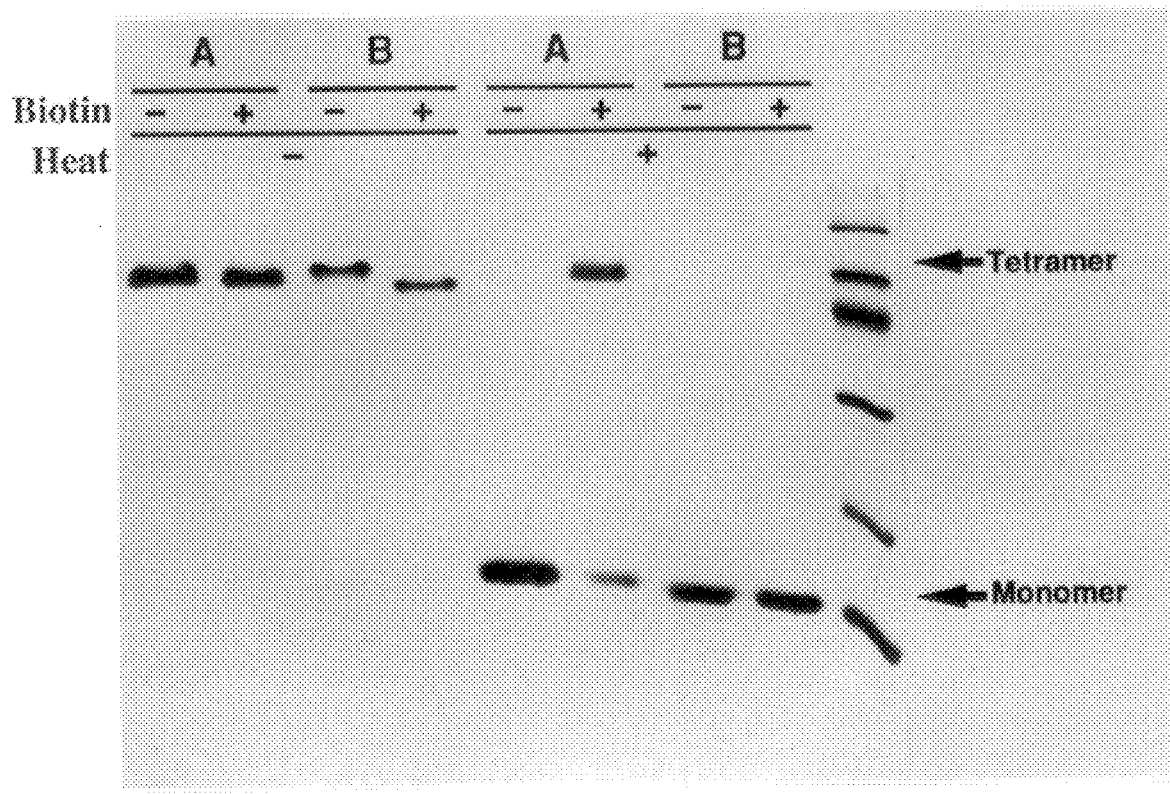
FIG. 5 Effects of biotin binding on subunit association.

Because the hydrophobic contact made by Trp-120 to biotin occurs through the dimer—dimer interface, this intersubunit communication may contribute to the biotin-induced tighter subunit association of streptavidin, which is observed in core streptavidin. To test this possibility, the subunit association of Phe-120 streptavidin with and without biotin was investigated by SDS-PAGE (FIG. 5).

Natural core streptavidin (5.0 μg; 0.37 nmol subunits) (FIG. 5, lanes marked A) or Stv-38 (4.0 μg; 0.32 nmol subunits) (FIG. 5, lanes marked B), in 4 μl of TBS, was mixed with an equal volume of TBS without or with 1.7 nmol biotin (molar ratio of biotin to subunit, 4.6 for natural core streptavidin and 5.3 for Stv-38), and the mixtures incubated at 21° C. for 5 minutes. To each of these mixtures (8 μl), 2 μl of 3.0% SDS, 100 mM Tris-HCl, pH 6.8, and 40% glycerol were added to a final SDS concentration of 0.6%. The resulting samples were either incubated at 21° C. for 5 minutes or heated in boiling water for 3 minutes, and subjected to SDS-PAGE.

Upon heat treatment in the presence of SDS, wild type core streptavidin and Phe-120 streptavidin, both without biotin, dissociate completely into monomers. However, the dissociation of natural core streptavidin was partly repressed by biotin-binding, and two distinct protein bands corresponding to the tetramer and monomer were observed. In contrast, no tetramer band was observed with Phe-120 streptavidin even in the presence of biotin under the same conditions, indicating that its subunit association was not tightened significantly upon biotin-binding. This demonstrated that the inter-subunit contact made by Trp-120 to biotin was the primary force that induced the tighter subunit association of natural streptavidin upon biotin-binding.

Even without heat treatment, a part of Phe-120 streptavidin dissociated into monomers in the presence of SDS, while no dissociation was observed with wild type core streptavidin. Biotin-binding had only a slight effect on the dissociation of Phe-120 streptavidin without heat treatment. This indicated that Trp-120 also contributes to the subunit association of tetramers in the absence of biotin.

Because hydrophobic interactions around the dimer—dimer interface are the major force for stable association of two symmetric dimers, the reduction in hydrophobicity around the dimer—dimer interface, caused by the mutation of Trp-120 to Phe, would also reduce the overall stability of the dimer—dimer association.

Example 9
Crosslinking Streptavidin to a Solid Support.

Reduced substrate affinity streptavidin was dialyzed extensively against binding buffer (0.5 M sodium phosphate, pH 7.5) to remove inhibitors before attaching to solid supports. Cyanogen bromide activated beads (Pharmacia Biotech; Piscataway, N.J.) were washed with 100 volumes of binding buffer to remove preservatives and used immediately for coupling. Mutant streptavidin was crosslinked to the beads by adding the activated beads to the mutant streptavidin and mixing gently overnight at room temperature. Uncrosslinked mutant streptavidin was removed by washing the beads with binding buffer followed by a solution of 1 M NaCl and 0.05 M sodium phosphate, pH 7.5. Unreacted groups were blocked by incubating the beads in 100 mM ethanolamine, pH 7.5, for 4 hours with gentle mixing. After ethanolamine was removed by washes with phosphate buffered saline (PBS; 0.144 g/L $KH_2PO_4$, 9 g/L NaCl, 0.795 g/L $Na_2HPO_4 7H_2O$), the reduced substrate affinity streptavidin coupled beads were ready for use.

Example 10
Separation of Biotinylated from Non-Biotinylated Proteins.

A chromatography column is used for separation of a biotinylated protein from a mixture of proteins. Reduced substrate affinity streptavidin coupled beads are poured into the column and washed with 5 column volumes of phosphate buffered saline (PBS). The protein mixture is added to the column and the biotinylated proteins are adsorbed to the column for 30 minutes. The non-biotinylated proteins are washed away with PBS. Biotinylated protein is removed from the column with a wash solution of PBS containing biotin at a concentration of 500 μM.

Example 11
Cell sorting: Isolation of Human T and B cells.

Bone marrow transplants are sometimes helpful in the treatment of cancers, particularly leukemia. However, there are very few stem cells in the blood and a cell sorting method will be useful in their isolation. Reduced affinity streptavidin may be used to isolate a specific cell population from blood. Isolation of B cells and T cells from blood is used as an example. Lymphocytes are prepared from whole blood by gradient separation using a Ficoll-Paque® gradient (Pharmacia Biotech; Piscataway, N.J.) and resuspended in a final cell concentration of $10^8$ per ml. One ml of purified lymphocytes and 2 mls of glass beads coated with reduced substrate affinity streptavidin is used for T and B cell isolation.

Two mls of reduced substrate affinity streptavidin coated glass beads are placed into a 3 ml column. Beads are washed with 10 mls of PBS and air bubbles in the column bed removed by centrifuging columns at 1000×g for 10 minutes. Ten mg of purified biotinylated goat anti-human IgG (heavy and light chain) (Pierce Chemical Co.; Rockford, Ill.) in PBS are applied to the column. Antibody is absorbed to the beads at room temperature for one hour in a rotator. Unbound antibodies are removed by washing the column with 30 mls of PBS.

Cell sorting is performed by applying the lymphocytes to the column at 500 μl per minute and collect the flow through fraction which contains the T cells. Additional T cells are removed by washing the column with 15 mls of PBS at 500 μl per minute. Optimal yield and separation of B cells and T cells are dependent on a constant flow rate. The optimal flow rate for a 2 ml column should be less than about 5 mls per minute and about 500 μl per minute. Eluate from loading and washing fraction contains the T cells. B cells are eluted from the column with 15 mls of 2 mM Biotin in PBS.

Example 12
Multiple Detection Techniques: Multiple Westerns.

An oncogene expression profile of a tumor can be determined by successive probing of a western blot using a variety of antibodies conjugated to $^{125}$I-labeled streptavidin. Briefly, 500 µCi of $^{125}$I-labeled N-succinimidyl 3-(4-hydroxyphenyl propionate) (ICN Radiochemicals; Irvine, Calif.) in dimethylformamide is air dried to the bottom of a tube. Radiolabeling is initiated by the addition of 10 µg of reduced substrate affinity streptavidin in 10 µl of 0.1 M sodium borate to the tube. Mutant streptavidin is labeled on ice for 15 minutes and the reaction terminated with 100 µl of 0.5 M ethanolamine, 10% glycerol, 0.1% xylene cylanol and 0.1 M sodium borate, pH 8.5. Labeled streptavidin is separated from the labeling reagent on a gel filtration column.

Biotinylated anti-myc antibody and biotinylated anti-ras antibody are labeled individually by contacting the antibody with $^{125}$I-labeled streptavidin. A western blot having multiple lanes of total proteins from tumors is probed with the $^{125}$I-labeled anti-myc antibody. Briefly, 10 mls PBS, with 3% dried milk and 1 µg/ml anti-myc antibody is contacted with the blot for one hour with agitation. Non-specific binding is washed away with PBS. Myc expression is detected by an autoradiograph of the blot. The $^{125}$I labeled streptavidin is removed by washing the blot with PBS and 2 mM biotin. Biotin is removed by washing the blot with PBS. Ras expression can be detected by repeating the procedure with an anti-ras antibody. A profile of oncogene expression in multiple tumors is revealed in successive autoradiographs.

In addition to western blots, this multiple probing technique may also be used for dot and slot blots, nucleic acid blots (Northern, Southern), Histology section probed with antibodies, karyotype hybridization (Chromosome spread), expression library screening with antibodies, cDNA library screening with nucleic acid probes and far-western blots with labeled protein.

Example 13

Deletion of Residues 113–120 and Mutation of Codon 127.

Expression vectors were constructed by standard methods using pTSA-13 which encodes the minimum sized core streptavidin consisting of amino acid residues 16–133 as a starting material. Oligonucleotide-directed mutagenesis was performed on a bacteriophage M13mp18 derivative, mpSA-29, carrying the entire coding sequence for the minimum-sized core streptavidin from pTSA-13, to convert the codon for His-127 (CAC) to GAC for Asp using an 18-base oligonucleotide, 5'-d(AGGTG TCGTC GCCGA CCA)-3' (SEQ ID NO 3). A 405-bp Nde I fragment carrying the entire coding sequence was cloned into the Nde I site of the plasmid pET-3a under the control of the psi10 promoter. The resulting expression vector, pTSA-33 (FIG. 6), encodes a core streptavidin mutant, Stv-33 (12.6 KDa per subunit) in which His-127 is replaced with Asp-127.

Two separate polymerase chain reactions (PCR) were performed using the expression vector pTSA-33 as the template to generate two partial DNA fragments of the coding sequence for streptavidin. One PCR amplification used the following set of oligonucleotides as primers: 5'-d (AATAC GACTC ACTAT AG)-3' (T7 promoter primer; SEQ ID NO 4) and 5'-d(GTTG T TCGAA GTCAG CAGCC ACTGG GT)-3' (SEQ ID NO 5). This PCR amplification generated a 380-bp fragment containing a sequence from the translation initiation site to the codon for Ser-112 followed by the recognition sequence for the restriction endonuclease BstB I (underlined). The other PCR amplification used the following set of primers: 5'-d(TTGC T TCGAA GTCCA CGCTG GTCGG C)-3' (SEQ ID NO 6) and 5'-d(CGGGC TTTGT TAGCA GCCGG A)-3' (SEQ ID NO 7). This PCR amplification generated a 150-bp fragment containing a BstB I recognition site (underlined) followed by a sequence from the codon for Lys-121 to a translation termination codon (TAG). The 380-bp PCR fragment was digested with Nde I and BstB I, and the 150-bp PCR fragment was with BamH I and BstB I. The resulting two fragments were ligated via the BstB I termini and the ligated fragment (420-bp) was cloned between the Nde I and BamH I sites of pET-3a under the control of the psi10 promoter. The resulting expression vector, pTSA-43 (FIG. 6), encodes a core streptavidin mutant, Stv-43 (11.8 kDa per subunit) in which a sequence from Gly-113 to Trp-120 has been deleted in addition to the mutation of His-127 to Asp-127. pTSA-43 also carries silent mutations in the codons for Thr-111 (ACC) and Ser-112 (TCC) which have been converted to ACT and TCG, respectively.

Example 14

Addition of 5 Cysteines to Core Streptavidin.

Cysteine residues are added to the carboxyl terminus of streptavidin to allow conjugation to other molecules through sulfhydryl reactions. A plasmid DNA, encoding residues 16 to 133 of streptavidin with Lys at position 127 is used as the starting material. Plasmid is digested with EcoR I and BamH I. Two 21 mer oligonucleotides, 5'-d(AAT TGC TGC TGC TGC TGC TAA)-3' (SEQ ID NO 8), 5'-d(GAT CTT AGC AGC AGC AGC AGC)-3' (SEQ ID NO 9) are annealed, and the resulting double-stranded DNA inserted and ligated into the EcoR I and BamH I sites of the predigested plasmid. The sequence of the resulting plasmid is confirmed by DNA sequencing using a dideoxy termination method. This gene is cloned into a bacterial expression vector and the mutated streptavidin expressed and purified. This streptavidin mutant has all the properties of the previous streptavidin mutant. It forms heterotetramers in solution and, with a phenylalanine at position 120, has a reduced biotin-binding affinity of less than about $10^8$ M$^{-1}$. In addition, this streptavidin mutant may be conjugated to other proteins and macromolecules, and also solid supports through the sulfhydryl group on the cysteines.

Example 15

Construction of Expression Vectors.

Expression vectors were constructed by using standard techniques (J. Sambrook et al., *Molecular Cloning: A Laboratory Manual*, Cold Spring Harbor Laboratory Press, 2nd Edition, 1989). mpSA-29, derived from M13mp18, which codes for a core streptavidin (E. A. Bayer et al., Biochem. J. 259:369–76,1989; T. Sano et al., Proc. Natl. Acad. Sci. USA 87:142–46, 1989) containing amino acids 16 to 133 (T. Sano et al., Proc. Natl. Acad. Sci. USA 92:3180–84, 1995) was used as a starting material. Mutations were introduced into the coding sequence of mpSA-29 using an oligonucleotide-directed in vitro mutagenesis system (Amersham) (J. R. Sayers et al., Nucleic Acids Res. 16:791–802, 1988). Three sets of mutations were introduced separately into a codon for His-127 (CAC): CAC→TGC for Cys; CAC→AAA for Lys; and CAC→GAC for Asp. Coding sequences containing the desired mutations were cloned into the Nde I site of pET-3a under the control of psi10 promoter (F. W. Studier et al., Methods Enzymol. 185:60–89,1990). Resulting expression vectors, pTSA-C127, pTSA-K127 and pTSA-33 encode the streptavidin mutants Stv-C127, Stv-K127 and Stv-D127, in which His-127 is replaced by Cys, Lys or Asp, respectively.

Example 16

Expression and Purification of Streptavidin Mutants.

Expression of each streptavidin mutant was carried out as described (T. Sano et al., Proc. Natl. Acad. Sci. USA 87:142–46, 1989) using BL21 (DE3) (pLysE) (F. W. Studier et al., Methods Enzymol. 185:60–89, 1990) carrying an expression vector. Each mutant was purified which included 2-iminobiotin affinity chromatography (K. Hofmann et al., Proc. Natl. Acad. Sci. USA 77:4666–68, 1980). For Stv-C127, 2-mercaptoethanol was included in all solutions to prevent disulfide bond formation during purification (T. Sano et al., Bio/Technology 11:201–6, 1993).

Example 17
Preparation of Reversible Two-Chain Tetrameric Streptavidin, Stv-C127.

Oxidation of Stv-C127 was attempted to make a reversible two-chain tetramer. Disulfide bonds between the sulfhydryl groups of Cys-127 across the dimer—dimer interface were formed by lyophilizing Stv-C127 to remove 2-mercaptoethanol that had been used to prevent disulfide bond formation during purification. Disulfide bonds were also formed by treating the protein with 0.15% hydrogen peroxide at room temperature (~22° C.) for 90 minutes. After disulfide bond formation, proteins were dialyzed against water and stored at 4° C.

Example 18
Paration of Two-Chain Tetrameric Streptavidin using Stv-C127.

The irreversible chemical crosslinker 1,3-dibromoacetone (ICN) was used to make an irreversible covalent bond between two cysteine residues through the dimer—dimer interface of Stv-C127. Formation of irreversible covalent bonds between cysteine residues requires protected sulfhydryl groups. This was accomplished by resuspending lyophilzed Stv-C127 (3 µg) in 6 µl of 5 mM DTT in 100 mM potassium phosphate (pH 7.8) (R. W. Hruz et al., Prot. Sci. 1:1144–53, 1992). After incubation at room temperature for 1 hour, the DTT concentration was reduced to 1 mM by the addition of 100 mM potassium phosphate, pH 7.8. Then, 10 µl of 1,3-dibromoacetone dissolved in ethanol were added to a final concentration of 2 mM. The reaction mixture was incubated at room temperature for 15 minutes in the dark and the reaction was terminated by the addition of DTT to a final concentration of 5 mM. Resulting proteins were dialyzed against water and stored at 4° C.

Example 19
Preparation of Hybrid Streptavidin using Stv-D127 and Stv-K127.

Preparation of a hybrid streptavidin tetramer was attempted by mixing crude Stv-D127 and Stv-K127 in 7 M guanidine hydrochloride, pH 1.5, at an approximately 4:1 ratio, followed by renaturation by removal of guanidine hydrochloride. Subsequent purification was the same as described above. Purified protein was dialyzed against water and stored at 4° C. A zero-length crosslinker, 1-ethyl-3-[3 (dimethylamino) propyl]carbodiimide (EDC), was used to cross-link the β-carboxyl group of Asp-127 of one subunit with the ε-amino group of Lys-127 of an adjacent subunit. Sulfo-N-hydroxysuccinimide (sulfo-NHS) (Pierce Chem.; St. Louis, Mo.) was used to improve the conjugation efficiency (J. V. Staros et al., Anal. Biochem. 184:244–48, 1986). Approximately 60 pmoles of purified protein were lyophilized and then dissolved in 100 mM 2-N-morpholinoethanesulfonic acid (MES) (pH 5.0), 5 mM sulfo-NHS, 30 mM EDC. Relatively low protein concentrations were used during cross-linking reactions to minimize the formation of higher molecular aggregates. Crosslinking reactions were carried out at room temperature for 3 hours. Fifty mM hydroxylamine-HCl was added to quench the reaction and regenerate unreacted carboxyl groups. Crosslinked protein was dialyzed against water and stored at 4° C.

Thermal stability of streptavidin mutants was determined. Each streptavidin construct (approximately 240 pmoles) with or without D-[carbonyl-14C]biotin (52 mci/mmol; Amersham) was dissolved in 6.5 µl of water and heated from 25° C. to 70° C., 80° C., 90° C., and 95° C. at a rate of 2° C./minute. Protein solutions were kept at these temperatures for 10 minutes and cooled to 25° C. at a rate of 2° C./minute. Resulting protein samples were incubated at room temperature for 1 hour in 1.25% SDS, 40 mM Tris-HCl, pH 6.8, and subjected to SDS-PAGE analysis. cl Example 20
Purification of Dimeric Streptavidin.

Preparation of crude Stv-33 was carried out by the method used for other recombinant streptavidin derivatives. Briefly, cell lysates of BL21(DE3)pLysE) carrying pTSA-33, which had been incubated for 4 hours after induction, was prepared and treated with DNase I and RNase A. An inclusion body fraction was collected by centrifugation of the cell lysate at 39,000×g for 20 minutes and dissolved in 7 M guanidine hydrochloride (pH 1.5). The dissolved protein solution was dialyzed against 0.2 M ammonium acetate (pH 6.0)/0.02% Tween 20/0.02% $NaN_3$. The dialyzed fraction was centrifuged at 39,000×g for 20 minutes and the supernatant was used as crude Stv-33.

To purify Stv-43, several modifications were made on the procedure used for Stv-33. An inclusion body fraction was prepared by the method above from BL21(DE3)(LysE) carrying pTSA-43 which had been incubated for 4 hours after induction. The inclusion body fraction was dissolved in 7 M guanidine hydrochloride (pH 1.5). To the resulting solution, biotin was added to a final concentration of 2.4 µg/ml and the mixture was dialyzed against 0.2 M ammonium acetate (pH 6.0)/0.02% Tween 20/0.02% $NaN_3$ containing 2.4 µg/ml biotin and against Tris-buffered saline containing Tween 20 (TTBS; 150 mM NaCl/20 mM Tris-Cl, pH 7.4/0.02% $NaN_3$/0.02% Tween 20) plus 2.4 µg/ml biotin. The dialyzed fraction was centrifuged at 39,000×g for 20 minutes and the supernatant was filtered through a 0.22 µm cellulose acetate membrane filtration unit (Falcon 7111). To remove biotin bound to Stv-43, the filtrate was subjected to three sequential dialysis steps; first against TTBS to remove free, unbound biotin; second against TTBS containing 10 mM urea to remove bound biotin; and finally against TTBS to remove urea. The dialyzed fraction was applied to a biotin-agarose (Pierce) column which had been equilibrated with TTBS. Unbound materials were removed by washing the column with TTBS and bound proteins were eluted with TTBS containing 2.4 µg/ml biotin to remove urea and the dialyzed fraction was filtered through a 0.22 µm polyvinylidene fluoride membrane filtration unit (Millex-GV; Millipore). The filtrate, containing Stv-43 with biotin, was stored at 4° C.

To remove bound biotin from purified Stv-43, the protein was subjected to the three sequential dialysis steps used during purification of Stv-43. The resulting Stv-43 without biotin was stored at 4° C. and used within three days after preparation.

Example 21
Stability of Streptavidin Mutants in Guanidine Hydrochloride.

Each streptavidin construct (approximately 160 pmoles) was incubated for 20 minutes in 15 µl of D-[8,9-$^3$H]biotin (47 Ci/mmol; Amersham) to fill approximately 22 pmoles of the biotin-binding site, followed by the addition of 2 µl of unlabeled biotin to saturate remaining biotin binding sites.

983 μl of 7 M guanidine hydrochloride, pH 0.89, was added and the mixture was incubated at room temperature for 90 minutes. Control experiments were performed by incubating proteins in 150 mM NaCl, 50 mM ammonium acetate, pH 6.0, without guanidine hydrochloride. Released biotin was separated from streptavidin-biotin complexes using Ultrafree-MC centrifugal filter units (Millipore) with a molecular mass cutoff of 10 kDa, and quantitated by liquid scintillation counting.

Example 22
Binding of Biotinylated DNAs.

Each lyophilized streptavidin construct was mixed with a 1:100 molar ratio of an end-biotinylated 18-base DNA in 4.5 M NaCl and the mixture incubated for 2 hours. Streptavidin-biotinylated DNA complexes were desalted and run on a 15% non-denaturing gel (J. Sambrook et al.,*Molecular Cloning:A Laboratory Manual*, Cold Spring Harbor Laboratory Press, 2nd Edition, 1989).

SDS-PAGE analysis was carried out with a discontinuous buffer system (U. K. Laemmli Nature 227:680–85,1970) using 15% polyacrylamide gels. Biotin-binding ability was determined by gel filtration chromatography (R. -D. Wei Methods Enzymol. 18A:424–27, 1970) using PD-10 columns (Pharmacia) and D[carbonyl-14C]biotin (52 mCi/mmol; Amersham).

Example 23
Construction of Streptavidin Mutants.

Two recombinant core streptavidins, Stv-25 and Stv-13, were tested for solubility and binding properties. Stv-25, with a mass of 13.2 kilodaltons per subunit, has an amino acid sequence very similar to natural core streptavidins. Stv-13, with a mass of 12.6 kilodaltons, has a further truncation of the terminal residues and consists essentially of only the β-barrel structure characteristic of streptavidin.

Expression vectors for recombinant core streptavidins were constructed using standard recombinant nucleic acid techniques (J. Sambrook et al., *Molecular Cloning: A Laboratory Manual*, 2nd ed., Cold Spring Harbor Laboratory Press, Cold Spring Harbor, N.Y., 1989.). Oligonucleotide-directed in vitro mutagenesis (J. R. Sayers et al.,Bio/Techniques 13:592–96,1992) was used to introduce mutations into the coding sequence for streptavidin. Two expression vectors, pTSA-13 and pTSA-25 (FIG. 6), were constructed by using a cloned natural streptavidin gene (C. E. Argara na et al., Nucleic Acids Res. 14:1871–82,1986) as the starting material. pTSA-13 carries a DNA sequence encoding amino acid residues 16–133 of mature streptavidin, while pTSA-25 encodes amino acid residues 14–138. To enable high level expression in bacteria, the coding sequences of streptavidin were cloned into T7 expression vectors pET-3a (F. W. Studier et al., J. Mol. Biol. 189:113–30, 1986; F. W. Studier et al., Methods Enzymol. 185:60–89, 1990) under the control of the Φ10 promoter, followed by the TΦ transcription terminator of bacteriophage T7.

Example 24
Expression and Purification of Recombinant Core Streptavidins.

Expression of each recombinant core streptavidin was performed by using the T7 expression system (F. W. Studier et al., J. Mol. Biol. 189:113–30, 1986; F. W. Studier et al.,Methods Enzymol. 185:60–89,1990), using established procedures (T. Sano et al., Proc. Natl. Acad. Sci. USA 87:142–46, 1990; T. Sano et al., Biochem. Biophys. Res. Commun. 176:571–77, 1991; T. Sano et al., Bio/Technology 11:201–6, 1993). Briefly, a host bacteria BL21(DE3) (pLysE) (F. W. Studier et al., Methods Enzymol. 185:60–89, 1990) carrying an expression vector was grown at 37° C. with shaking in LB medium (10 grams bacto-tryptone, 5 grams bacto-yeast extract and 10 grams sodium chloride per liter, pH 7.0) supplemented with 0.4% glucose, 150 μg/ml ampicillin and 25 μg/ml chloramphenicol. Growth of the bacteria was monitored using a photospectrometer calibrated with sterile LB for adsorption at 600 nanometers. Sterile LB was used to calibrate the photospectrometer. When the absorbance at 600 nm of the culture reached 0.6, isopropyl-β-D-thiogalactopyranoside was added to a final concentration of 0.5 mM to induce the expression of the 17 RNA polymerase gene placed under the lacUV5 promoter. After induction, cells were incubated at 37° C. with shaking for four hours before harvest and purification of expressed protein.

Stv-13 was expressed efficiently in *E. coli*. In contrast, while STV-25 was still expressed in usable amounts, its expression efficiency of Stv-25 was lower than that of Stv-13. This may be caused by codons for the terminal sequences present in Stv-25 (but absent in Stv-13) which occur at low frequencies in highly expressed *E. coli* genes.

Purification of Stv-13 and Stv-25 was performed using 2-iminobiotin affinity chromatography according to procedures previously described (T. Sano et al., Proc. Natl. Acad. Sci. USA 87:142–46, 1990; T. Sano et al., Biochem. Biophys. Res. Commun. 176:571–77,1991; T. Sano et al.,Bio/Technology 11:201–6,1993; K. Hofmann et al., Proc. Natl. Acad. Sci. USA 77:4666–68, 1980). Purified recombinant core streptavidins were stored frozen at −70° C. until used. Homogeneous Stv-13 and Stv-25 are tetramers and bind four biotins per molecule as does natural streptavidin.

Figure 7:
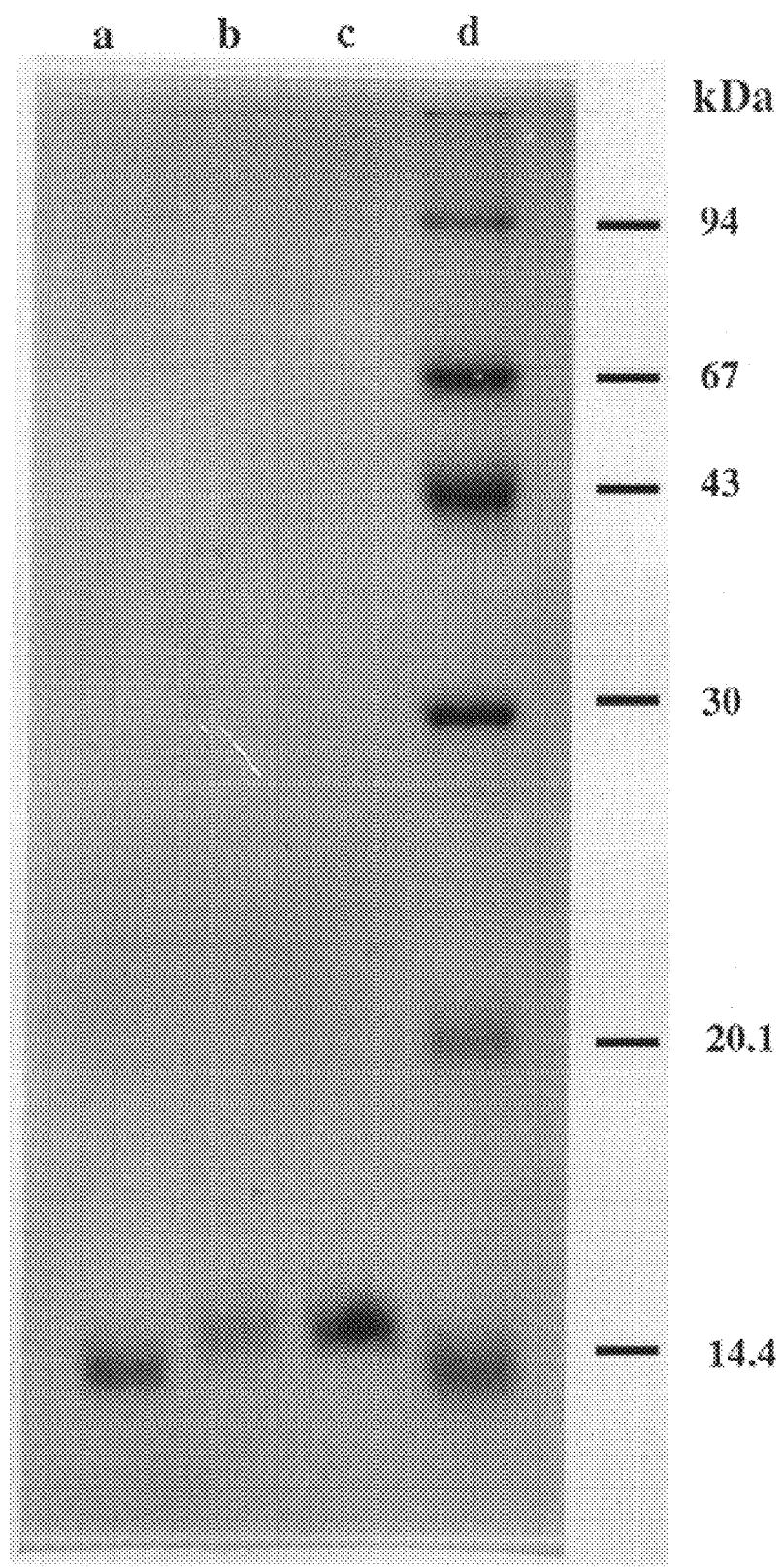
FIG. 7 SDS-PAGE/Coomassie brilliant blue analysis of purified core streptavidins.

The purity of expressed Stv-13 (FIG. 7, lane a) and Stv-25 (FIG. 7, lane b), and natural core streptavidin (FIG. 7, lane c) were monitored using SDS-PAGE and standard molecular weight markers (FIG. 7, lane d) following purification to homogeneity. Analysis of the proteins at different stages of purification shows a clear difference in subunit molecular mass (650 Daltons; seven amino acid residues) between Stv-13 and Stv-25. Natural core streptavidin, purchased commercially (Boehringer Mannheim), also showed a single band on SDS-PAGE with a migration similar to that of Stv-25. Terminal sequence analysis of natural core streptavidin obtained from the same source (E. A. Bayer et al., Biochem. J. 259:369–76,1989), showed that this natural core streptavidin consists of amino acid residues 13–139.

Example 25
Determination of Solubility Characteristics of Expressed Proteins.

To determine the effect of terminal sequences remaining in natural core streptavidin on the solubility characteristics, the solubility of each core streptavidin species with and without biotin was investigated by varying the concentration of ammonium sulfate or ethanol in the solution.

Analysis of solubility in the absence of biotin was performed by adjusting the concentration of each core streptavidin to 5.7 nanomoles of subunits per mililiter in TBS1 [Tris-buffered saline: 150 mM NaCl, 20 mM Tris-HCl, pH 7.4,0.02% NaN$_3$. This corresponds to 72 μg/ml for Stv-13 and 76 μg/ml for Stv-25 and natural core streptavidin. To 100 μl of this protein solution, 1.1 ml of an appropriate ammonium sulfate solution in TBS was added to adjust the final concentration of ammonium sulfate (final streptavidin concentration, 0.48nanomoles of subunits per milliter). The mixture was allowed to stand at 30° C. for 30 minutes and centrifuged at 2,200×g for 20 minutes. The amount of soluble streptavidin in the supernatant fraction was determined by biotin-binding assays described below. The fraction of original streptavidin remaining in the supernatant is defined as the relative solubility.

Analysis of solubility in the presence of biotin was performed in a similar method to analysis in the absence of biotin. Biotin-binding sites of each core streptavidin were saturated by adding an equimolar amount of D-[carbonyl-$^{14}$C]biotin, prior to the addition of an ammonium sulfate solution. The amount of soluble streptavidin in the final supernatant was estimated from the radioactivity derived from bound biotin, determined by liquid scintillation counting.

Analysis of solubility using ethanol was similar to analysis made using ammonium sulfate with two modifications. After the addition of ethanol, the final volume was adjusted to 1.2 ml by the addition of an appropriate ethanol solution to make the final protein concentration constant for all samples. After incubation at 30° C. for 30 minutes, centrifugation was performed at 13,000×g for 20 minutes.

The collected solubility data of streptavidin with biotin (FIG. 8B), without biotin (FIG. 8A) vs. ammonium sulfate and of streptavidin with biotin (FIG. 8D), without biotin (FIG. 8C) vs. ethanol were plotted in FIG. 8. The solubility characteristics of Stv-13 (●), in ammonium sulfate or ethanol, were almost the same as those of Stv-25 (○) and natural core streptavidin (Δ), indicating that the additional truncation of the terminal sequences in Stv-13 has no significant effect on the solubility characteristics. However, Stv-13 showed an enhanced structural stability compared to Stv-25 and natural core streptavidin. For example, Stv-13 retained more than 80% of its biotin-binding ability after incubation in 6 M guanidine hydrochloride at pH 1.5, under which conditions, both Stv-25 and natural core streptavidin retained only about 20% of their biotin-binding ability. In addition, Stv-13 showed higher accessibility to end-biotinylated DNA than natural core streptavidin. The data shows that the terminal regions, present on the surface of natural core streptavidin, spatially hinder biotinylated macromolecules from approaching the biotin-binding sites, perhaps because of their disordered structure.

Relative solubility of the three core streptavidins, Stv-13, Stv-25 and natural core streptavidin, as the concentration of ammonium sulfate was altered showed biphasic changes (FIGS. 8A and 8B); the solubility decreased sharply with increasing concentrations of ammonium sulfate up to 50% saturation and then increased with further increases in ammonium sulfate concentration. In the absence of biotin, Stv-13 showed slightly lower solubility than Stv-25 and natural core streptavidin at ammonium sulfate concentrations up to 50% saturation, but Stv-13 had the highest solubility at 90% saturation of ammonium sulfate. Biotin binding slightly increased the solubility of the core streptavidins in the presence of ammonium sulfate. Similar to the solubility changes in the absence of biotin, Stv-13 showed slightly lower solubility than Stv-25 and natural core streptavidin at ammonium sulfate concentrations up to 50% saturation, but had the highest solubility at 70% and 90% saturation in the presence of biotin.

Figure 8A:
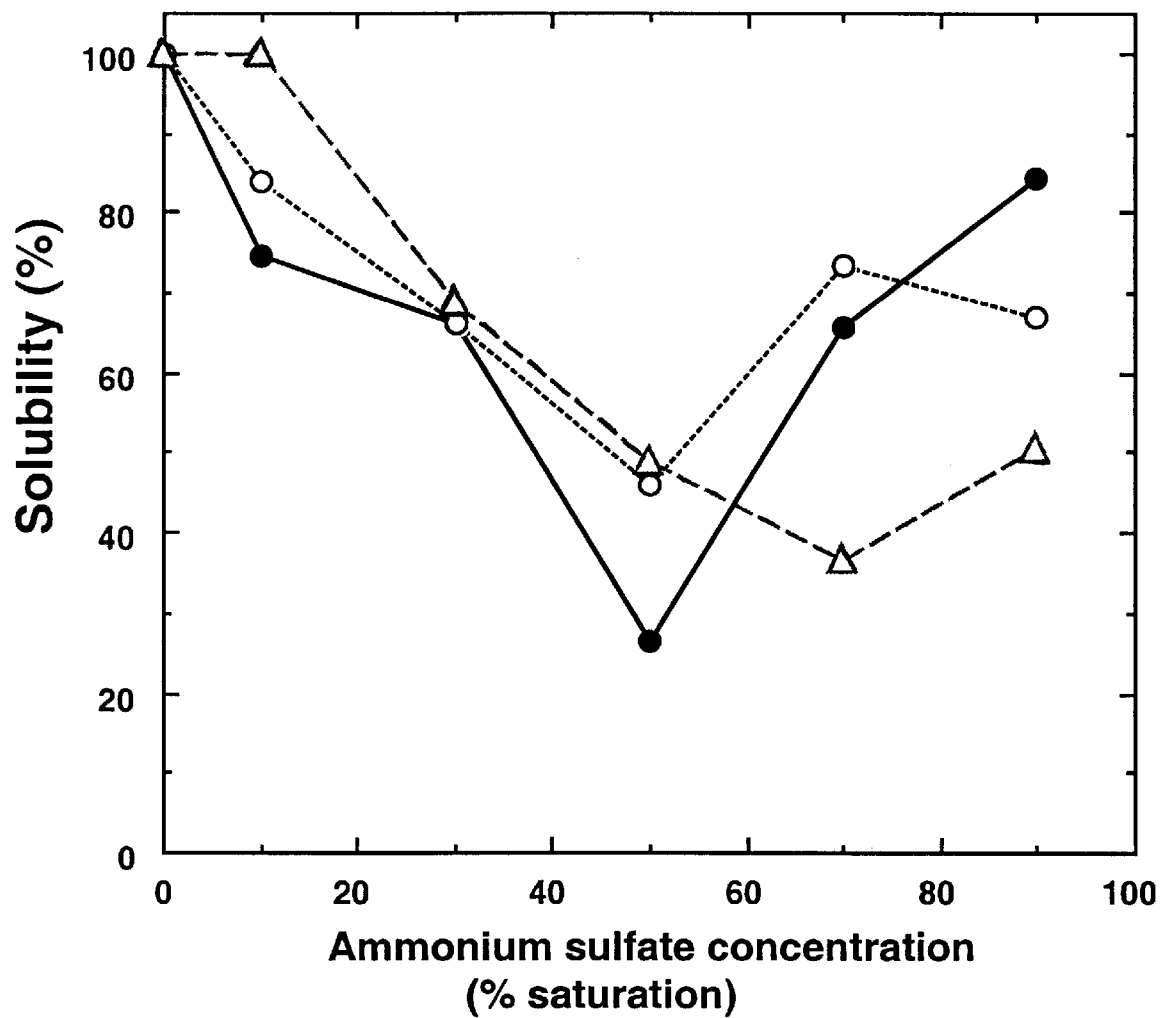
FIGS. 8A–8B Core streptavidins solubility characteristics with and without biotin in varying amounts of (8A) ammonium sulfate without biotin, (8B) ammonium sulfate with biotin, (8C) ethanol without biotin, and (8D) ethanol with biotin.
Figure 8B:
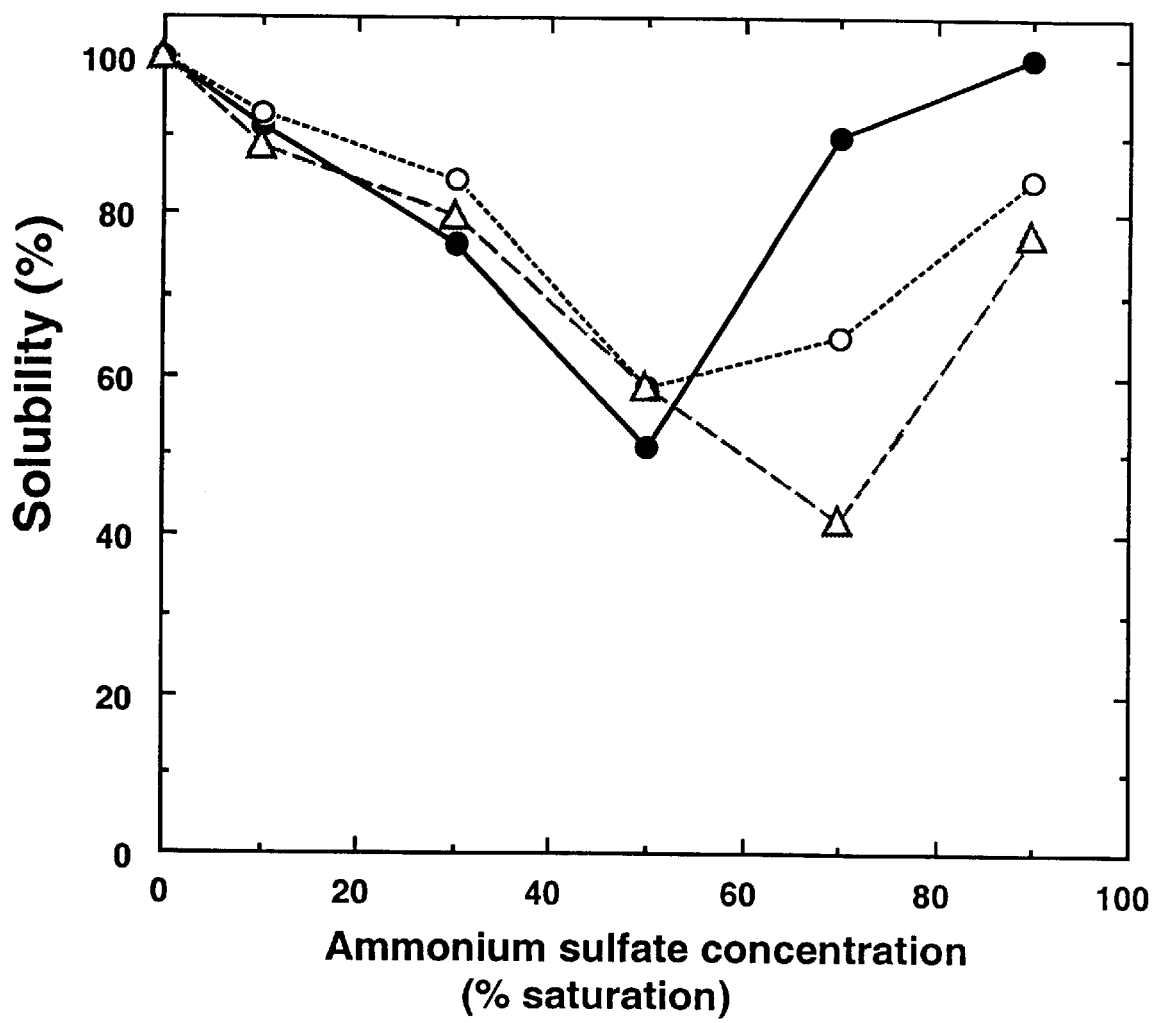
Figure 8C:
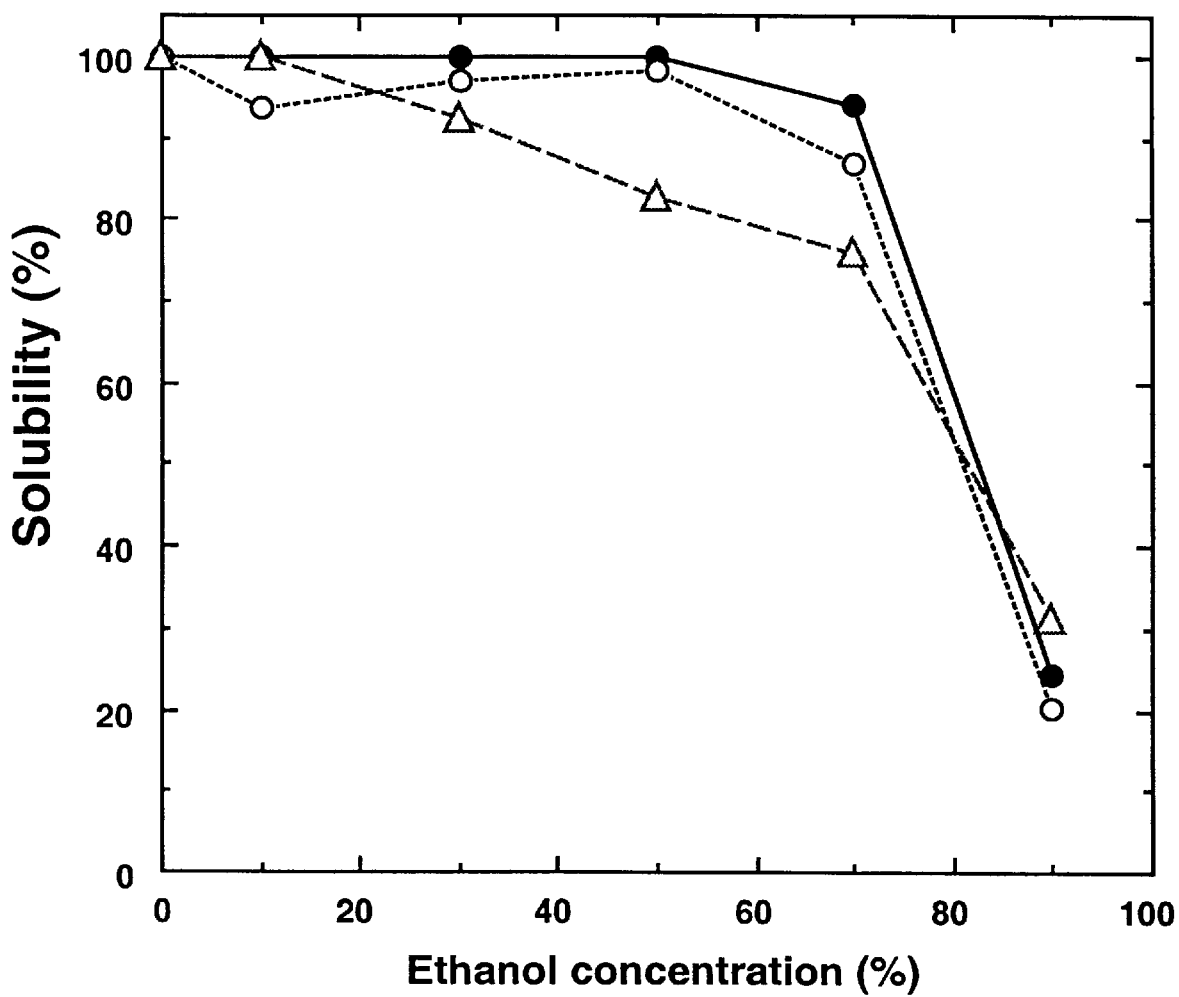
Figure 8D:
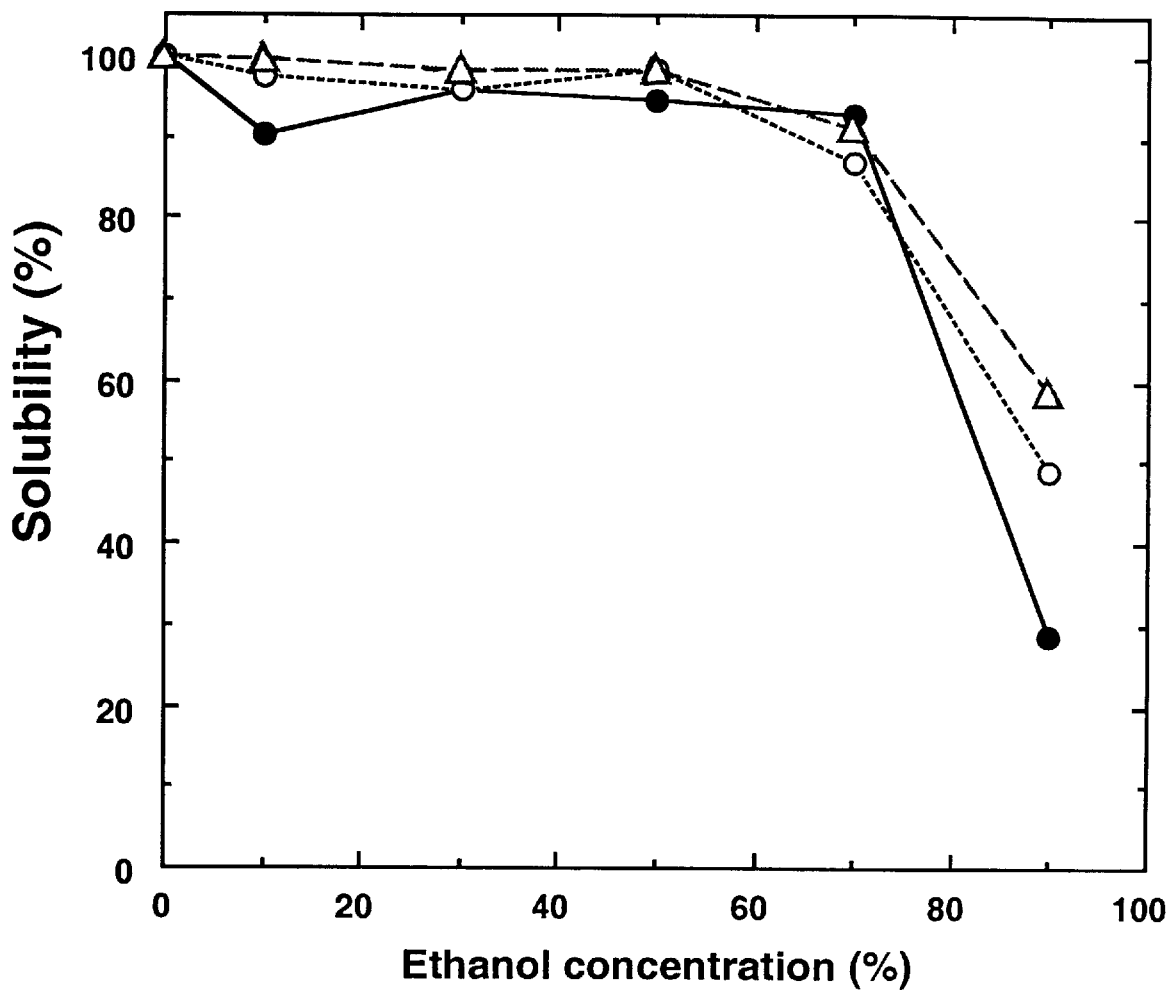

Three core streptavidins showed high solubility (more than 75%) at ethanol concentrations up to 70% in the absence of biotin (FIG. 8C). At an ethanol concentration of 90%, only about 30% of molecules remained soluble for all of the three core streptavidins. Biotin binding had a slight effect on the solubility of core streptavidins (FIG. 8D). There is no marked difference in the solubility characteristics in ethanol among the three core streptavidin species.

Although Stv-13 lacks two charged amino acid residues, Glu-14 and Lys-134 and two polar residues, Ser-136 and Ser-139, which are present in natural core streptavidin, there is no significant difference in solubility characteristics among the three core streptavidin species. This indicates that the terminal regions in natural core streptavidins have minimal effects on the solubility characteristics of core streptavidins, unlike those of full-length streptavidin.

Example 26

Stability of Expressed Proteins in Guanidine Hydrochloride.

To investigate how the terminal regions, present on the surface of natural core streptavidin molecules, affect the overall stability of streptavidin, urea gradient-PAGE (T. E. Creighton et al., J. Mol. Biol. 129:235–64, 1979) was performed using polyacrylamide gels with a urea concentration gradient from 0 M to 10 M, along with an acrylamide concentration gradient from 12% to 8%. As a control (T. E. Creighton et al., J. Mol. Biol. 129:235–64, 1979), urea gradient-PAGE analysis showed a marked decrease in migration of bovine serum albumin at high urea concentrations, indicating the unfolding of the molecule caused by urea. However, the three core streptavidins, Stv-13, Stv-25 and natural core streptavidin, showed no appreciable changes in migration at urea concentrations up to 10 M, indicating the extremely high structural stability of streptavidin. This also suggested that more stringent denaturation conditions are needed to allow a comparison of the stability of core streptavidins.

Guanidine hydrochloride, a denaturant more potent than urea, was used. At high concentrations and very acidic pH, guanidine hydrochloride effectively denatures streptavidin and releases bound biotin. Biotin-binding ability was used as an estimate of the structural stability.

Structural stability of core streptavidins against denaturation was estimated from the biotin-binding ability after incubation in guanidine hydrochloride solutions at pH 7.4 and pH 1.5. Stv-13, Stv-25 and natural core streptavidin was incubated at 22° C. for 10 minutes in 500 μl of an appropriate guanidine hydrochloride solution (final guanidine hydrochloride concentration, 0–6.0 M) at a protein concentration of 270 picomoles of subunits per milliliter (1.7 μg/ml for Stv-13 and 1.8 μg/ml for Stv-25 and natural core streptavidin). Then, 1.4 μl (680 pmol) of D-[carbonyl-$^{14}$C] biotin was added to each solution. The mixture was incubated at 22° C. for 10 minutes and streptavidin-biotin complexes were separated from free, unbound biotin using PD-10 columns which had been equilibrated with the same guanidine hydrochloride solution (R. -D. Wei, Methods Enzymol. 18A:424–27, 1980).

Figure 9A:
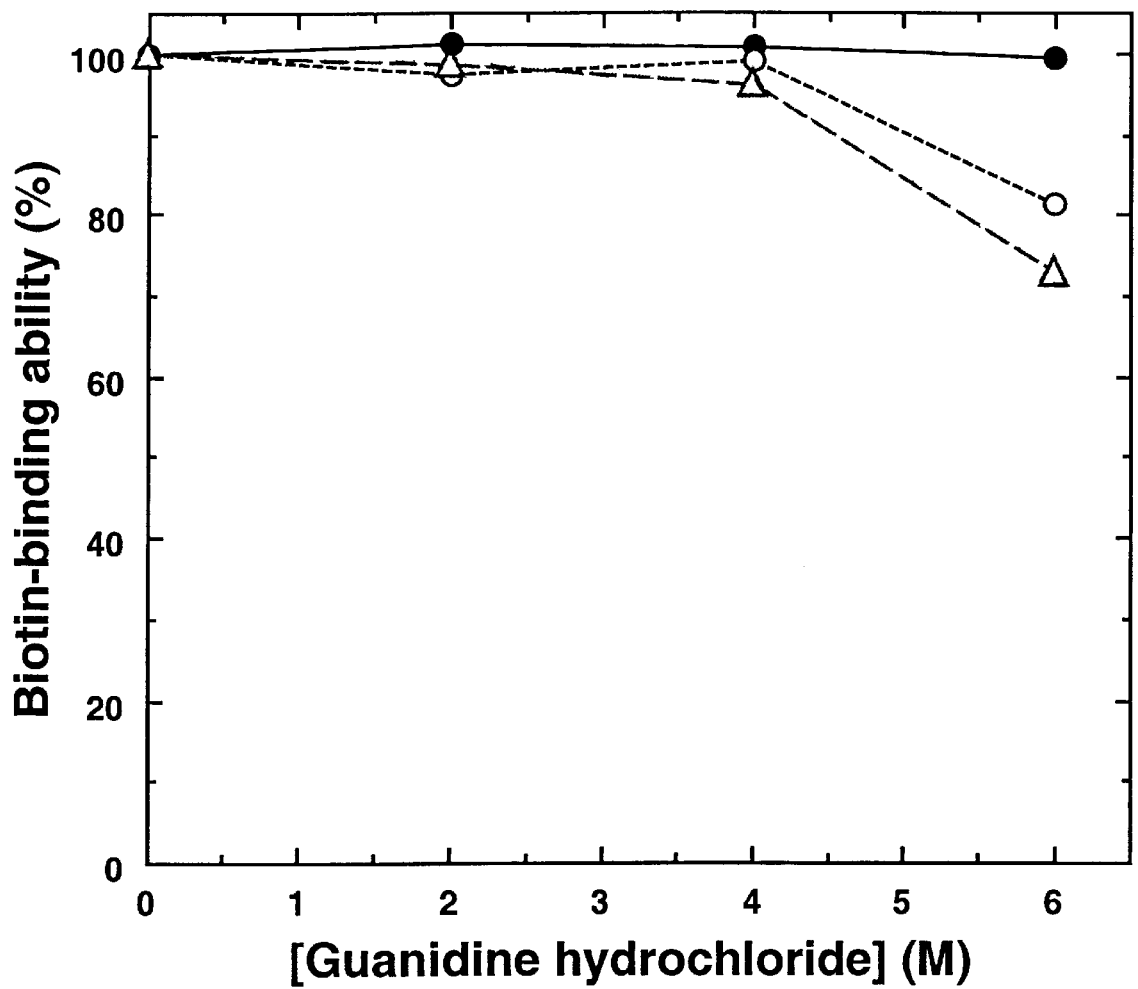
FIGS. 9A and 9B Two similar experiments (9A and 9B) comparing the stability of three core streptavidin proteins against denaturation by guanidine hydrochloride.

Stability data is plotted in FIG. 9 where Stv-13, Stv-25, and natural streptavidin is represented by (●), (○) and (Δ) respectively. Stv-13, Stv-25 and natural core streptavidin (270 picomoles of subunits per milliliter) were incubated at 22° C. for 10 minutes in guanidine hydrochloride solutions at pH 7.4 (A) or 1.5 (B). The biotin-binding ability of each core streptavidin was determined by gel filtration (R. -D. Wei, Methods Enzymol. 18A:424–27, 1980). All of the three core streptavidins bound more than 0.96 molecules of biotin per subunit at pH 7.4 without guanidine hydrochloride and the biotin-binding ability remaining in guanidine hydrochloride is indicated in percent.

At pH 7.4, almost no changes in biotin-binding ability were observed for all of the core streptavidins at guanidine hydrochloride concentrations up to 4 M (FIG. 9A), indicating the extremely high structural stability of streptavidin. At 6 M guanidine hydrochloride at pH 7.4, the biotin-binding ability of both Stv-25 and natural core streptavidin decreased by approximately 20%, while Stv-13 showed almost no reduction in biotin-binding ability. This result indicates that Stv-13 has a higher stability against denaturation by guanidine hydrochloride than Stv-25 and natural core streptavidin.

Figure 9B:
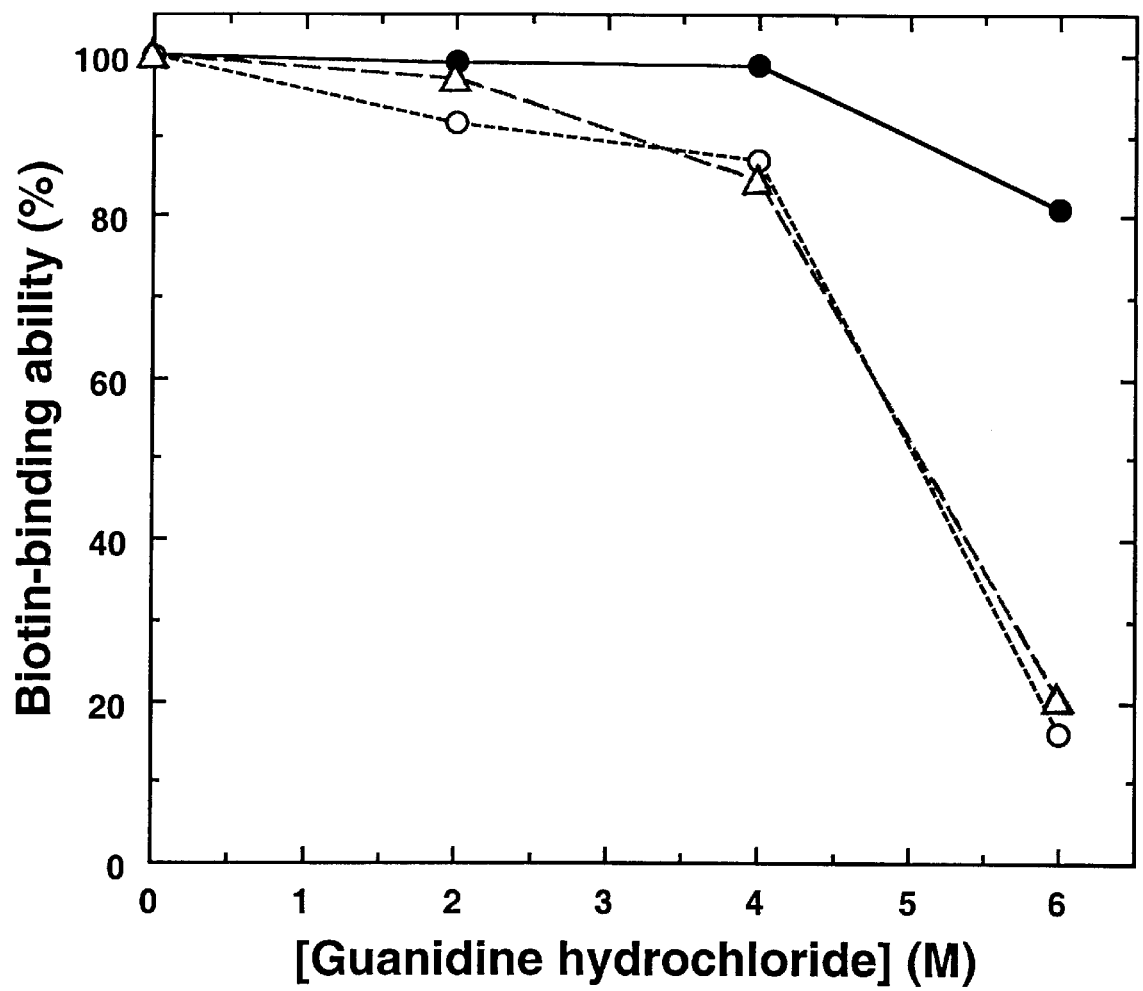

The enhanced structural stability of Stv-13 over Stv-25 and natural core streptavidin was observed even more clearly at pH 1.5 (FIG. 9B). Stv-13 retained almost full biotin-binding ability at guanidine hydrochloride concentrations up to 4 M. In contrast, Stv-25 and natural core streptavidin lost approximately 15% of the biotin-binding ability at 4 M guanidine hydrochloride. At 6 M guanidine hydrochloride at pH 1.5, Stv-13 retained more than 80% of the biotin-binding ability, while only about 20% of the biotin binding ability was retained with both Stv-25 and natural core streptavidin.

Stv-13 has an enhanced stability against denaturation by guanidine hydrochloride when compared with Stv-25 and natural core streptavidin indicating that the terminal regions on the surface of natural core streptavidin reduce the overall structural stability of streptavidin.

Example 27
Binding Ability of Expressed Streptavidin for Biotinylated DNA.

Full-length or only partially truncated streptavidin has a lower accessibility to biotinylated macromolecules than natural core streptavidins (E. A. Bayer et al., Biochem. J. 259:369–76, 1989), because of steric hindrance caused by the terminal regions which are located on the surface of the molecule. To estimate how the terminal sequences of core streptavidin affect the binding to biotinylated macromolecules, the biotinylated DNA-binding ability of two core streptavidin species, Stv-13 and natural core streptavidin, was investigated.

Briefly, an end-biotinylated double-stranded DNA target was mixed with core streptavidins at various ratios and the mixtures were separated by agarose gel electrophoresis, followed by staining the DNA targets with ethidium bromide. The DNA used was a 3179-bp linear double-stranded DNA target, in which one of the 3-termini contains a biotin moiety. This target biotinylated DNA was prepared by using an Acc I-Hind III fragment of the plasmid pGEM-3Zf(+) (Promega). Biotin was incorporated into the Hind III terminus by filling-in reactions in the presence of a biotinylated deoxynucleotide analog, biotin-14-dATP (Gibco BRL), as described earlier (T. Sano, Science 258:120–22,1992). Core streptavidin and the biotinylated target DNA were mixed at various ratios in 10 mM Tris-HCl, pH 8.0, 0.1 mM EDTA and the mixtures were allowed to stand at 37° C. for 90 minutes, followed by electrophoretic separation on 1% agarose gels and DNA was staining with ethidium bromide.

Figure 10:
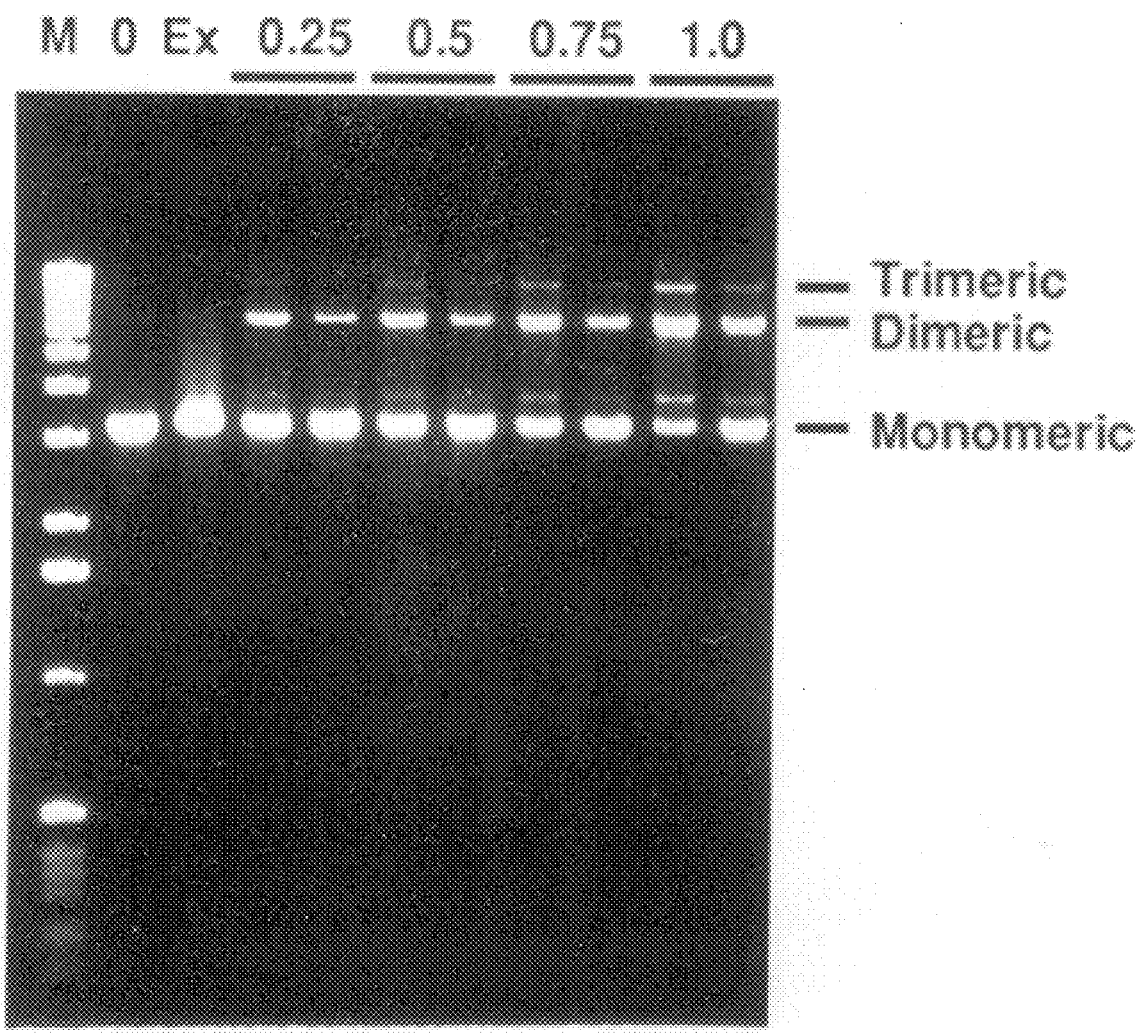
FIG. 10 Ability of core streptavidins to bind biotinylated DNA.

The results of electrophoretic analysis are shown in FIG. 10. Lane M represents a one kilobasepair molecular weight marker. Lane "0" and lane "Ex" represents no streptavidin and a thousand fold excess of streptavidin, respectively. Stv-13 and natural streptavidin form the left and right lanes respectively for each molar ratio of 0.25, 0.5, 0.75, and 1 tested. Electrophoretic analysis (FIG. 10) shows that larger amounts of dimeric (approximately 6.4 kilobasepair) and trimeric (9.5 kilobasepair) biotinylated DNA targets, which are connected via single streptavidin molecules, were formed with Stv-13 than with natural core streptavidin at any molar ratio of streptavidin subunits to biotin used. Correspondingly, smaller amounts of DNA targets without streptavidin or with single streptavidin molecules (only slightly retarded from DNA targets without streptavidin which were not well resolved under the electrophoresis conditions used) were observed with Stv-13. Although this analysis is not quantitative, the result indicates that Stv-13 has an enhanced binding ability for biotinylated DNA over natural core streptavidin. Enhanced binding ability of Stv-13 for biotinylated DNA reveals that the terminal regions, present on the surface of natural core streptavidin molecules, sterically hinder the biotin-binding sites and prevent biotinylated macromolecules from approaching the biotin-binding sites due, presumably, to their disordered structure.

Example 28
Biotin Binding Ability of Expressed and Natural Streptavidin.

Biotin binding ability of expressed and natural Streptavidin was determined by gel filtration (R. -D. Wei, Methods Enzymol. 18A:424–27,1980). Natural streptavidin were purchased commercially (Boehringer Mannheim). Stv-13 and Stv-25 and natural core streptavidin bound more than 0.96 molecules of biotin per subunit, indicating that these core streptavidins have full biotin-binding ability. Gel filtration chromatography at 22° C. using a 1.6 by 85-centimeter Sephacryl S-300HR column showed that each of these core streptavidins is tetrameric and free from aggregate formation.

Example 29
Construction of Crosslinked Streptavidin.

The streptavidin tetramer is formed by interdigitating two symmetric dimers which are held together primarily by relatively weak van der Waals interactions. In contrast, two subunits are connected tightly by hydrogen bonds and van der Waals forces to form a symmetrical dimer. Thus, a streptavidin tetramer has two different subunit interfaces; one is the stable subunit interface in a symmetric dimer and the other is the weaker interface between two stable symmetric dimers (W. A. Hendrickson et al., Proc. Natl. Acad. Sci. USA 86:2190–94, 1989; P. C. Weber et al., Science 243:85–88, 1989). Since strong biotin binding requires the contacts made by adjacent subunits to biotin through the dimer—dimer interface, the disruption of the tetramer along the weaker dimer—dimer interface might lead to the release of biotin from streptavidin.

The known three-dimensional structure of the protein (W. A. Hendrickson et al., Proc. Natl. Acad. Sci.USA 86:2190–94,1989; P. C. Weber et al., Science 243:85–88, 1989) shows that His-127 of one subunit faces the same amino acid of the adjacent subunit across the dimer—dimer interface. This shows that amino acid substitutions at position 127 could be used to introduce a covalent bond between subunits through the dimer—dimer interface, resulting in the formation of two-chain tetrameric streptavidins. Because of the covalent bonds between subunits, prevention of dissociation of the tetramer along the dimer—dimer interface would enhance stability of the tetramer.

Three independent amino acid substitutions were carried out by replacing His-127 with cysteine, lysine or aspartic acid. Stv-C127, which contains a unique cysteine residue at position 127, was designed to generate two species of two-chain tetrameric streptavidins. One construct has a disulfide bond between adjacent subunits through the dimer—dimer interface; the other contains an irreversible covalent bond between the two sulfhydryl groups. Stv-K127 was designed to crosslink two Lys-127 across the dimer—dimer interface by using amino-specific homobifunctional crosslinkers. Stv-D127 was designed to make a hybrid streptavidin with Stv-K127. This hybrid protein would have enhanced subunit association across the dimer—dimer interface by electrostatic interactions between the $\epsilon$-amino group of Lys-127 of one subunit and the β-carboxyl group of Asp-127 of the adjacent subunit. This molecule should also allow the formation of an amide bond between these two residues by chemical crossliking.

Expression vectors were constructed using standard techniques (J. Sambrook et al. ,*Molecular Cloning: A Laboratory Manual*, 2nd ed., Cold Spring Harbor Laboratory Press, Cold Spring Harbor, N.Y., 1989). mpSA-29, derived from M13mp18, which codes for a core streptavidin (W. A. Hendrickson et al., Proc. Natl. Acad. Sci. USA 86:2190–94, 1989; C. E. Argara ña et al.,Nucleic Acids Res. 14:1871–82, 1986; Pähler et al., J. Biol. Chem. 262:13933–937, 1987; E. A. Bayer et al., Biochem. J. 259:369–76, 1989; T. Sano et al., Proc. Natl. Acad. Sci. USA 87:142–46,1989) containing amino acids 16 to 133 as a starting material (T. Sano et al., Proc. Natl. Acad. Sci. USA 92:3180–84, 1995). Mutations were introduced into the coding sequence of mpSA-29 with an oligonucleotide-directed in vitro mutagenesis system (Amersham) (J. R. Sayers et al., Nucleic Acids Res. 16:791–802, 1988). Three sets of mutations were introduced separately into a codon for His-127 (CAC): (i) CAC→TGC for Cys; (ii) CAC→AAA for Lys; and (iii) CAC→GAC for Asp. The coding sequence containing the desired mutations was cloned into the Nde I site of pET-3a under the control of Φ10 promoter (F. W. Studier et al., Methods Enzymol. 185:60–89, 1990). The resulting expression vectors, pTSA-C127, pTSA-K127 and pTSA-33 encode the streptavidin mutants Stv-C127, Stv-K127 and Stv-D127, in which His-127 is replaced by Cys, Lys, or Asp, respectively.

Example 30
Expression and Purification of Streptavidin Mutants.

Figure 11:
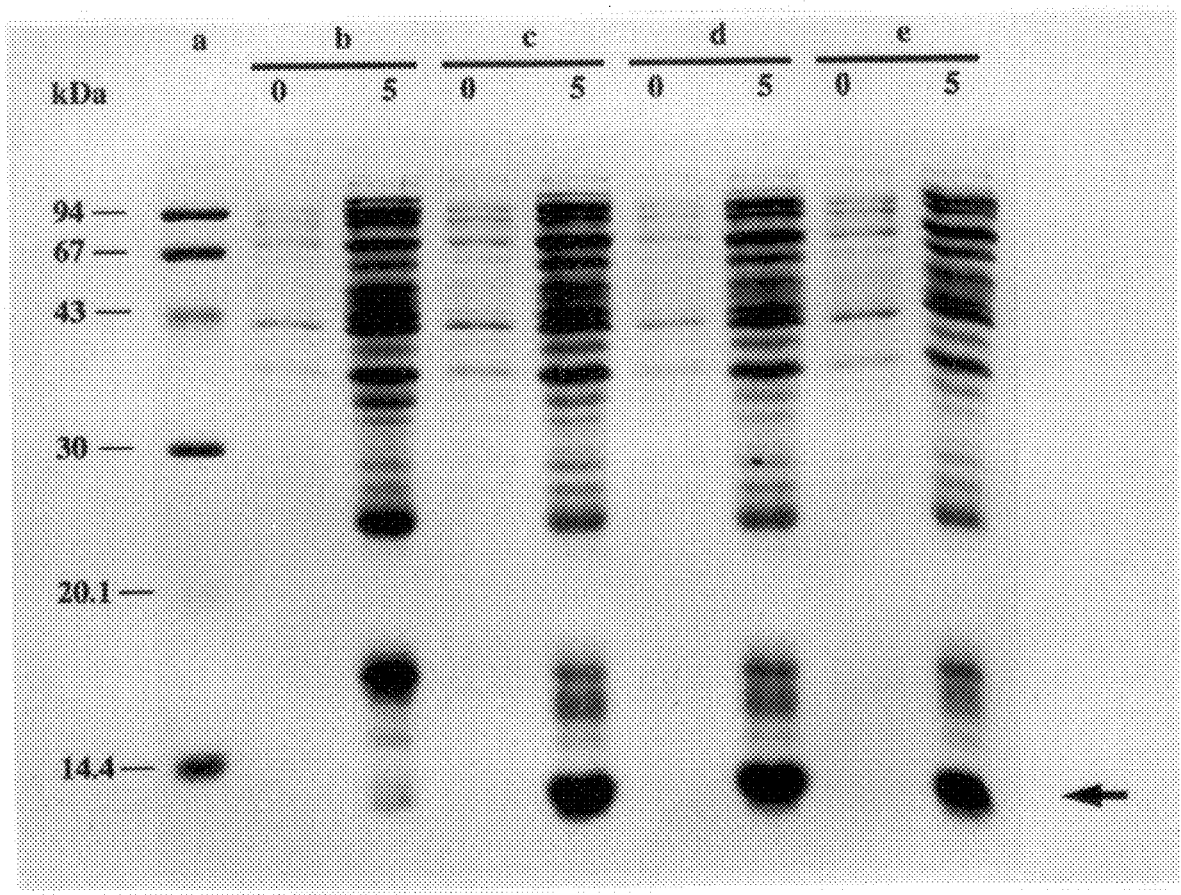
FIG. 11 Expression of streptavidin mutants Stv-C127, Stv-D127 and Stv-K127.

Streptavidin mutants were produced in *E. coli* by using the T7 expression system (F. W. Studier et al., Methods Enzymol. 185:60–89,1990), as previously described (T. Sano et al., Proc. Natl. Acad. Sci. USA 87:142–46, 1989). The expressed products of BL21(DE3)(pLysE)(pTSA-C127) (FIG. 11 lane C), BL21(DE3)(pLysE) (pTSA-D127) (FIG. 11 lane D), BL21 (DE3) (pLysE) (PTSA-K 1 27) (FIG. 11 lane E), a negative control, BL21 (DE3)(pLysE) (FIG. 11 lane b) and molecular weight markers (FIG. 11 lane A) were analyzed by SDS-PAGE and shown in FIG. 11. Two time points, at zero hours and five hours after induction, were taken for each sample and the arrow indicates the location of expressed streptavidin.

Expression of each streptavidin mutant was carried out as described by Sano and Cantor (Proc. Natl. Acad. Sci. USA 87:142–46, 1989) using BL21 (DE3) (pLysE) carrying an expression vector (F. W. Studier et al.,Methods Enzymol. 185:60–89, 1990). Purification of each mutant followed the method of Sano and Cantor (Proc. Natl. Acad. Sci. USA 87:142–46,1989), which includes 2-iminobiotin affinity chromatography (K. Hofmann et al., Proc. Natl. Acad. Sci. USA 77:4666–68, 1980). For Stv-C127, 2-mercaptoethanol was included in all solutions to prevent disulfide bond formation during purification (T. Sano et al., Bio/Technology 11:201–6,1993).

Stv-C127 and Stv-K127 were purified to homogeneity by a simple purification procedure (T. Sano et al., Proc. Natl. Acad. Sci. USA 87:142–46, 1989) including 2-iminobiotin affinity chromatography. Each of these two proteins formed a stable subunit tetramer. In contrast, Stv-D127 formed insoluble aggregates when renatured, indicating that this protein alone cannot form a stable tetramer.

Example 31
Preparation of Reversible and Irreversible Two-Chain Tetrameric Streptavidins using Stv-C127.

Figure 12:
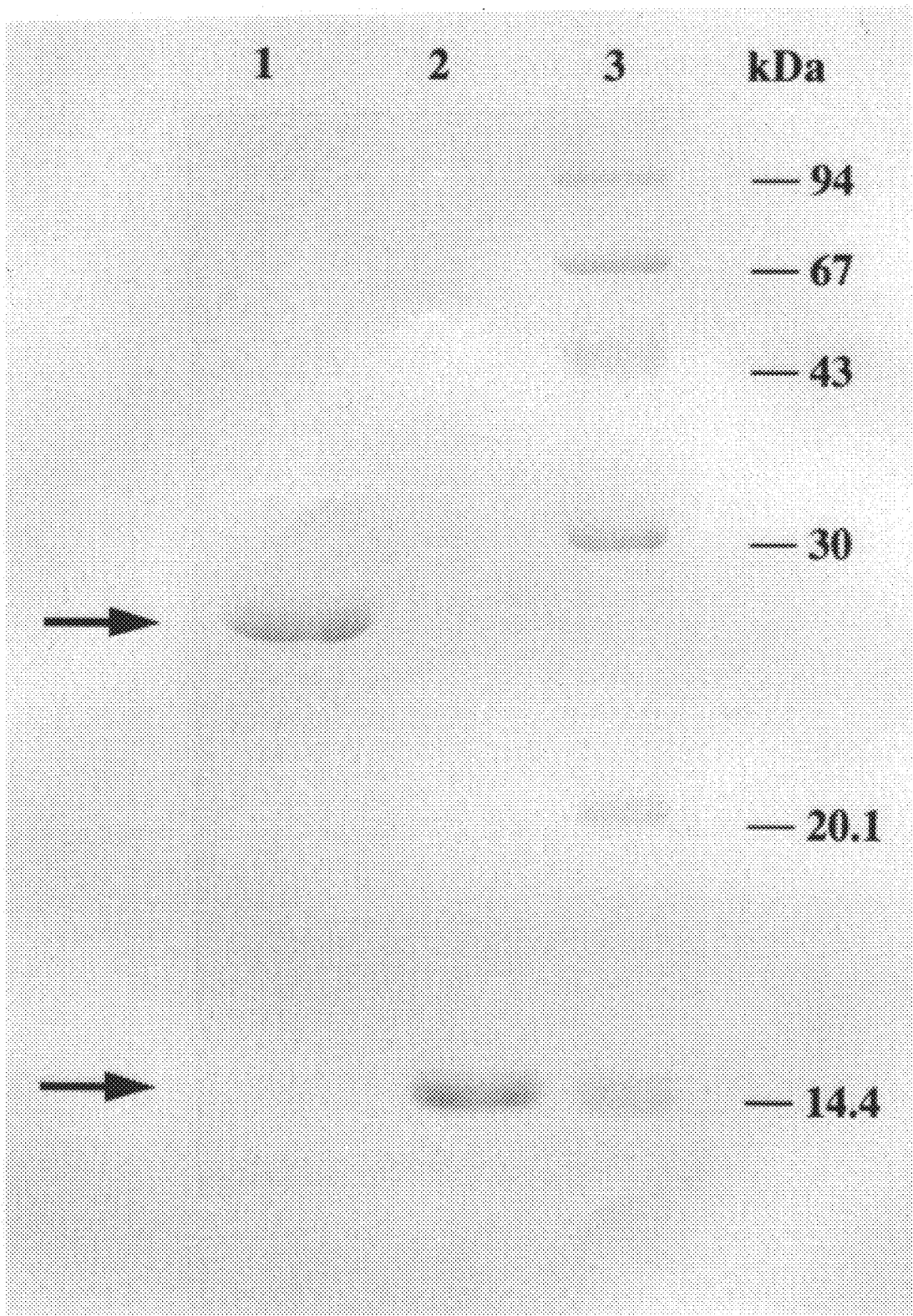
FIG. 12 SDS-PAGE analysis of disulfide bond formation in Stv-C127.

The cysteine residues at position 127 of Stv-C127 were oxidized by the removal of reducing agents. SDS-PAGE analysis (FIG. 12) in the presence of molecular weight markers (FIG. 12, lane 3) demonstrates that sulfhydryl groups of adjacent subunits across the dimer—dimer interface were crosslinked at approximately 100% efficiency (FIG. 12, lane 1), upon the removal of 2-mercaptoethanol by lyophilization. Disulfide bonds were readily dissociated by the addition of DTT (FIG. 12, lane 2). Similar results were obtained with this protein after oxidation with hydrogen peroxide. Formation of a disulfide bond between two cysteine residues showed no apparent effect on the biotin-binding ability of this protein. The successful reversible linkage of sulfhlydryl groups across the dimer—dimer interface reveals that the two cysteines residues are located in close proximity allowing the formation of a disulfide bond through the dimer—dimer interface.

Oxidation of Stv-C127 was attempted to make a reversible two-chain tetramer. Disulfide bonds between the SH groups of Cys-127 across the dimer—dimer interface were formed by lyophilizing Stv-C127 to remove 2-mercaptoethanol that had been used to prevent disulfide bond formation during purification. Disulfide bonds were also formed by treating the protein with 0.15% hydrogen peroxide at room temperature (~22° C.) for 90 minutes. After disulfide bond formation, proteins were dialyzed against water and stored at 4° C.

Figure 13:
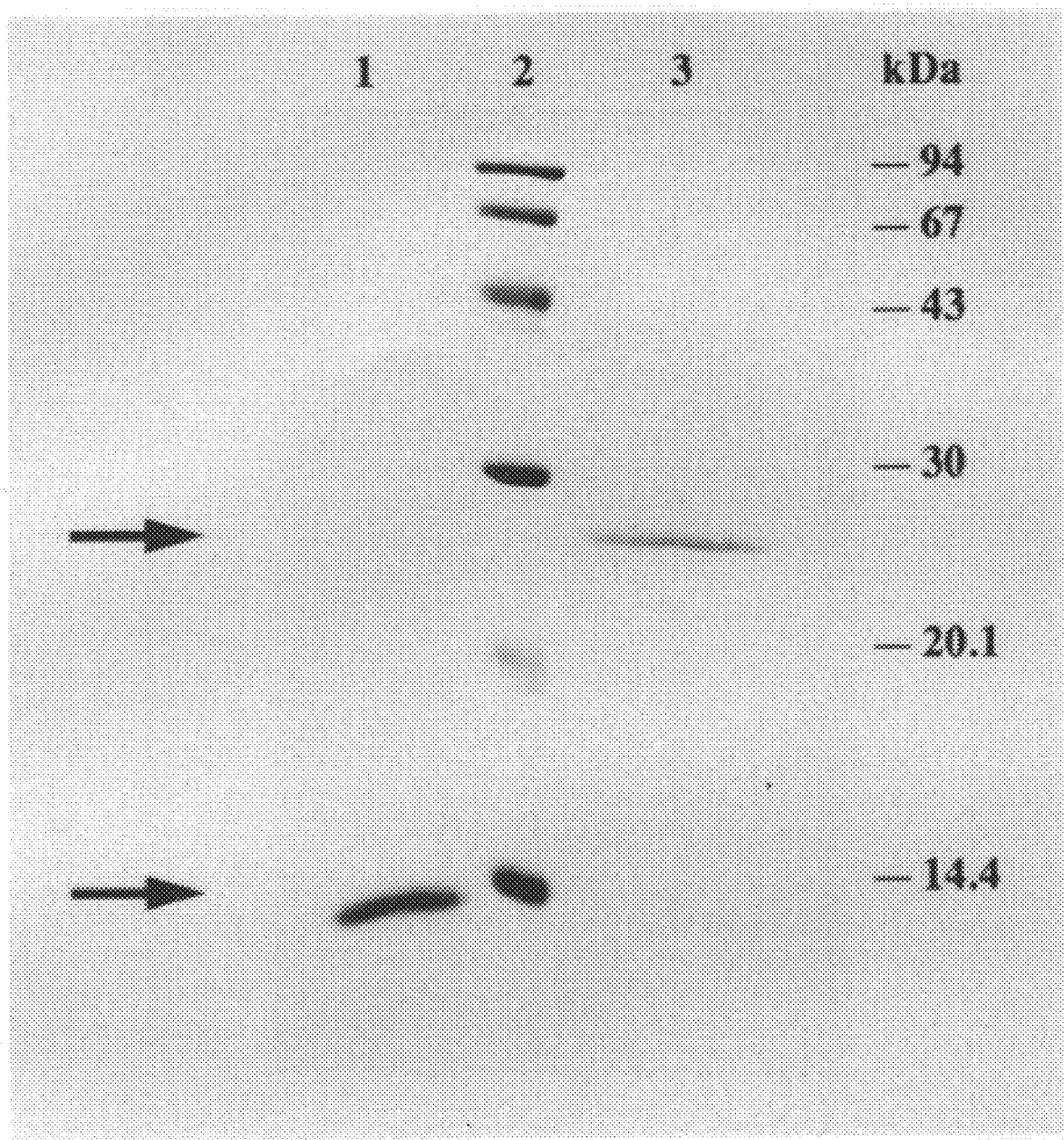
FIG. 13 SDS-PAGE analysis of crossliking of Stv-C127 with 1,3-dibromoacetone.

The formation of an irreversible covalent bond between two sulfhydryl groups through the dimer—dimer interface by using the irreversible crosslinker 1,3-dibromoacetone was performed at more than 90% efficiency. 1,3-dibromoacetone compound reacts first with a sulfhydryl group and then with another nucleophile within a 5-Å radius (S. S. Husain et al.,Biochem. J. 110:53–57,1968; S. S. Husain et al.,Chem. Commun. 310–311, 1968). Formation of irreversible covalent bonds between cysteine residues requires protected sulfhydryl groups. This was accomplished by resuspending lyophilized Stv-C127 (3 μg) in 6 μl of 5 mM DTT in 100 mM potassium phosphate (pH 7.8) (R. W. Hruz et al., Prot. Sci. 1:1144–53, 1992). After incubation at room temperature for one hour, the DTT concentration was reduced to 1 mM by the addition of 100 mM potassium phosphate (pH 7.8). Then, 10 μl of 1,3-dibromoacetone dissolved in ethanol were added to a final concentration of 2 mM. The reaction mixture was incubated at room temperature for 15 minutes in the dark and then the reaction was terminated by the addition of DTT to a final concentration of 5 mM. Resulting proteins were dialyzed against water and stored at 4° C. SDS-PAGE analysis of crosslinking of Stv-C127 with 1,3-dibromoacetone is shown in FIG. 13. Lane 1 represents Stv-C127 in the presence of DTT and Lane 3 shows Stv-C127 after crosslinking with 1,3-dibromoacetone. The SDS-PAGE analysis was performed in the presence of molecular weight standards (lane 2) and the subunit dimers (top) and monomers (bottom) are shown by arrows. All the samples were applied to gels after boiling for two minutes. The proteins in the gel were stained with Coomassie brilliant blue. This analysis shows the formation of crosslinked subunit dimers at a more than 90% efficiency. Formation of an irreversible covalent bond between two sulfhydryl groups had no effect on the biotin-binding ability.

Example 32
Preparation of Streptavidin with Intersubunit Crosslinks using STV-K127.

Stv-K127 was designed to make a crosslinked streptavidin, in which an irreversible covalent bond is formed between the $\epsilon$-amino groups of Lys-127 residues of adjacent subunits through the dimer—dimer interface. Several amino-specific homobifunctional crosslinkers were tested. SDS-PAGE of crosslinked products with bis (sulfosuccinimidyl)suberate (Pierce Chem. Co.; St. Louis, Mo.), an irreversible crosslinker with a spacer arm length of 11.4 Å, showed several bands corresponding to subunit dimers, trimers and tetramers and higher molecular weight aggregates, indicating that both inter- and intramolecular crosslinking occurred. Amino-specific crosslinkers with a shorter spacer such as dimethyladipimidate-2HCl (spacer= 8.6 Å), disuccinimidyl glutarate (spacer=7.7 Å) and n-hydroxysuccinimidyl 2,3-dibromopropionate (spacer=5.0 Å) (Pierce Chem. Co.; St. Louis, Mo.) were tested to see if nonspecific crosslinking reactions could be reduced. Although the formation of higher molecular weight aggregates was reduced, subunit trimers and tetramers were still formed, in addition to subunit dimers. These results indicate that Stv-K127 was unable to make specific crosslinks between Lys-127 residues through the dimer—dimer interface, using amino-specific homobifunctional crosslinkers tested.

Example 33
Preparation of Tetrameric Hybrid Streptavidin of Stv-D127 and Stv-K127.

Stv-D127 was used to make a hybrid tetramer consisting of Stv-K127 and Stv-D127. Stv-D127 alone forms insoluble aggregates and cannot make a stable tetramer. However, if a mixture of Stv-D127 and Stv-K127 was renatured, a hybrid tetramer, consisting of Stv-D127 and Stv-K127 subunits, would be preferentially formed over a tetrameric Stv-K127, because such hybrid streptavidin would have a more stable subunit association than Stv-K127 due to an enhanced electrostatic attraction between the $\beta$-carboxyl group of Asp-127 of one subunit and the $\epsilon$-amino group of Lys-127 of the adjacent subunit that should be positioned at the dimer—dimer interface. Excess Stv-D127 over Stv-K127 was used to prevent the formation of Stv-K127 homotetramers.

Figure 14:
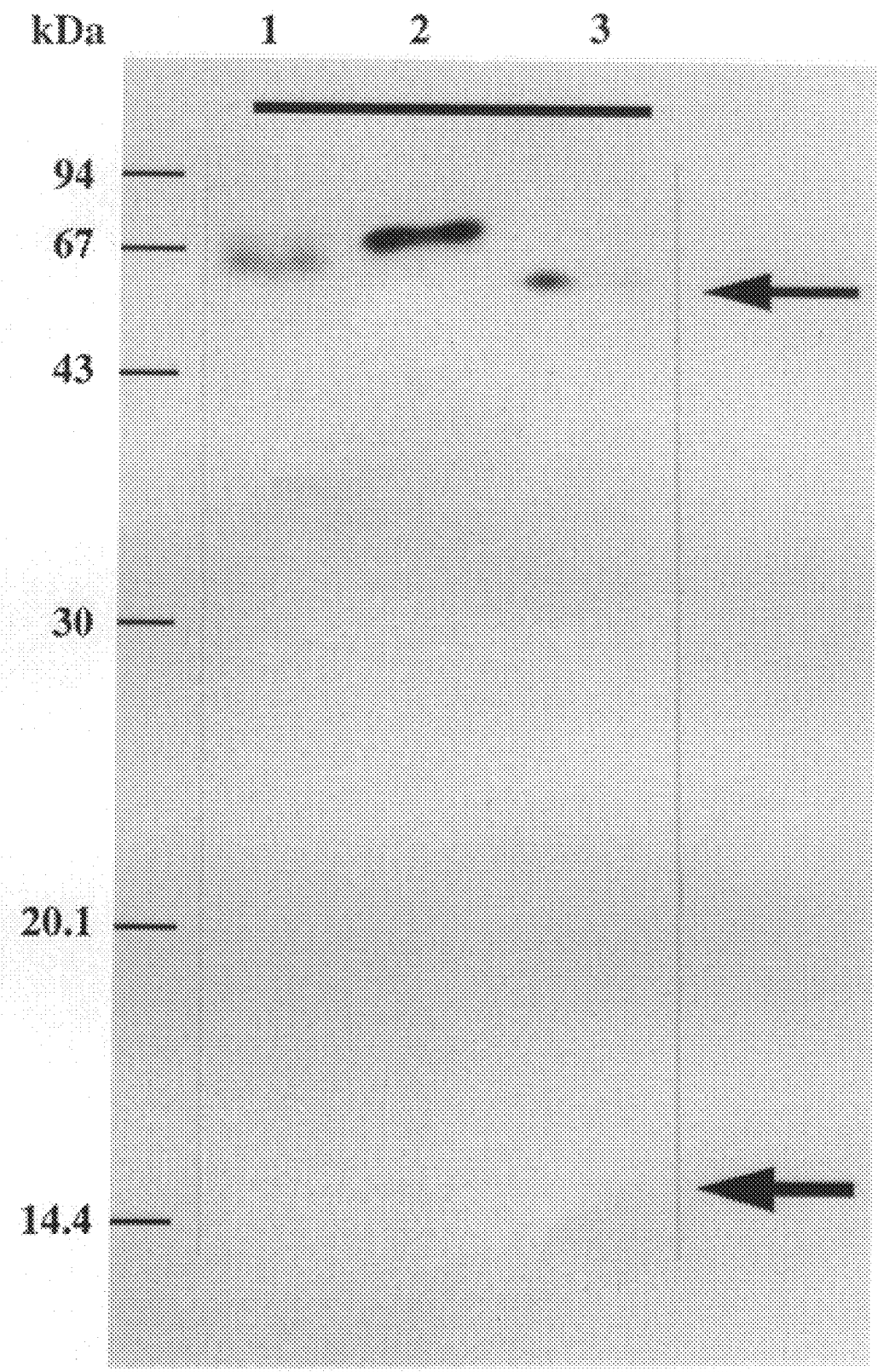
FIG. 14 SDS-PAGE analysis of natural core streptavidin, Stv-K127 and Stv-DK127.

To investigate if a hybrid tetramer had successfully been made, the purified protein was compared with Stv-K127 and natural core streptavidin (Boehringer Mannheim) by SDS-PAGE and shown in FIG. 14. In the SDS-PAGE analysis, natural core streptavidin (lane 1), Stv-K127 (lane 2) and Stv-DK127 (lane 3) without biotin or heat treatment were loaded into adjacent lanes. Comparison of the migration of these proteins indicated that the purified protein consists of a single species and migrated faster than Stv-K127 and natural core streptavidin. The faster migration of the purified protein than Stv-K127 shows that this protein consists of both Stv-D127 and Stv-K127 and thus this protein is termed Stv-DK127.

Preparation of a hybrid streptavidin tetramer was attempted by mixing crude Stv-D127 and Stv-K127 in 7 M guanidine hydrochloride (pH 1.5) at an approximately 4:1 ratio, followed by renaturation by removal of guanidine hydrochloride. The subsequent purification procedure was the same as described above. Purified protein was dialyzed against water and stored at 4° C. A zero-length crosslinker, 1-ethyl-3-[3(dimethylamino)propyl]carbodiimide (EDC), was used to cross-link the $\beta$-carboxyl group of Asp-127 of one subunit with the $\epsilon$-amino group of Lys-127 of an adjacent subunit. Sulfo-N-hydroxysuccinimide (sulfo-NHS) (Pierce Chem. Co.; St. Louis, Mo.) was used to improve the conjugation efficiency (J. V. Staros et al., Anal. Biochem. 184:244–48, 1986). Approximately 60 pmoles of purified protein were lyophilized and then dissolved in 100 mM 2-N-morpholinoethanesulfonic acid (MES) (pH 5.0), 5 mM sulfo-NHS, 30 mM EDC. Relatively low protein concentrations were used during cross-linking reactions to minimize the formation of higher molecular aggregates. Crosslinking reactions were carried out at room temperature for three hours and then, 50 mM hydroxylamine-HCl was added to quench the reaction and regenerate unreacted carboxyl groups. The crosslinked protein was dialyzed against water and stored at 4° C.

Example 34
Hybrid Streptavidin with Irreversible Intersubunit Crosslinks.

Figure 15:
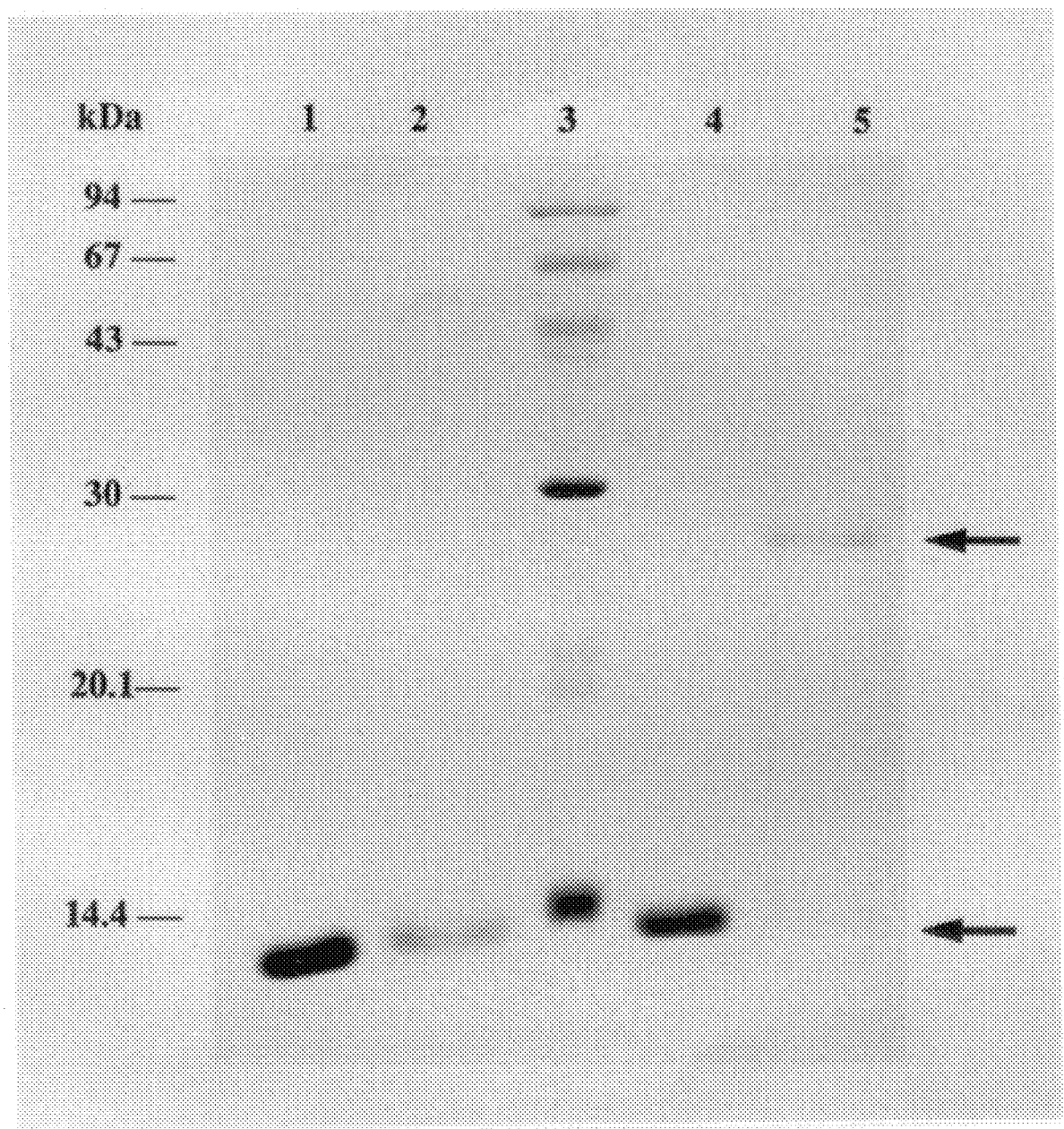
FIG. 15 SDS-PAGE analysis of Stv-K127 and Stv-DK127 before and after cross lin9ng.
Figure 16A:
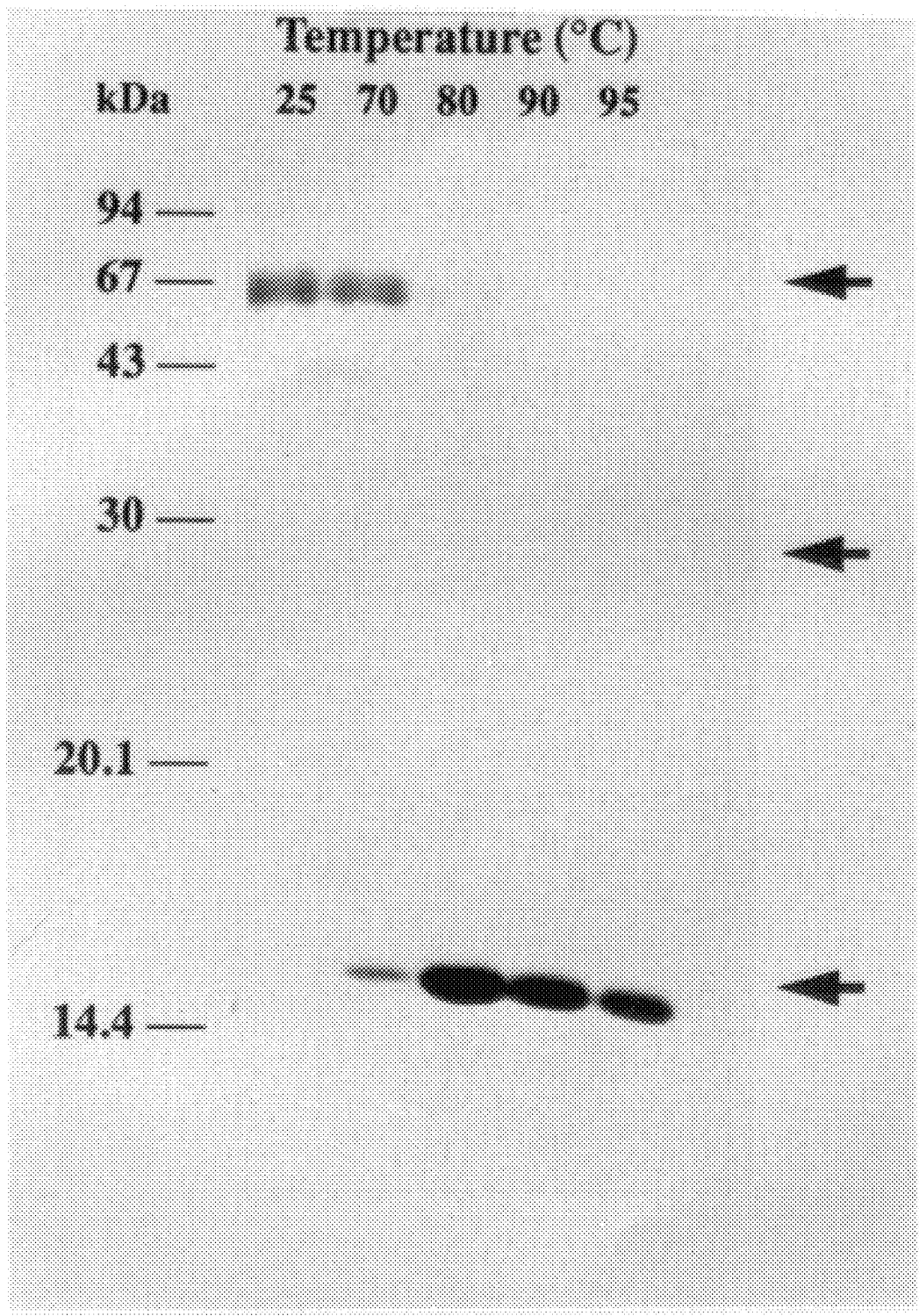
FIGS. 16A–16E SDS-PAGE analysis of the thermal stability of streptavidin proteins (16A) natural Stv, (16B) Stv-C127, (16C) Stv-C127 cross-linked, (16D) Stv-DK127, and (16E) Stv-DK127 cross-linked.
Figure 16B:
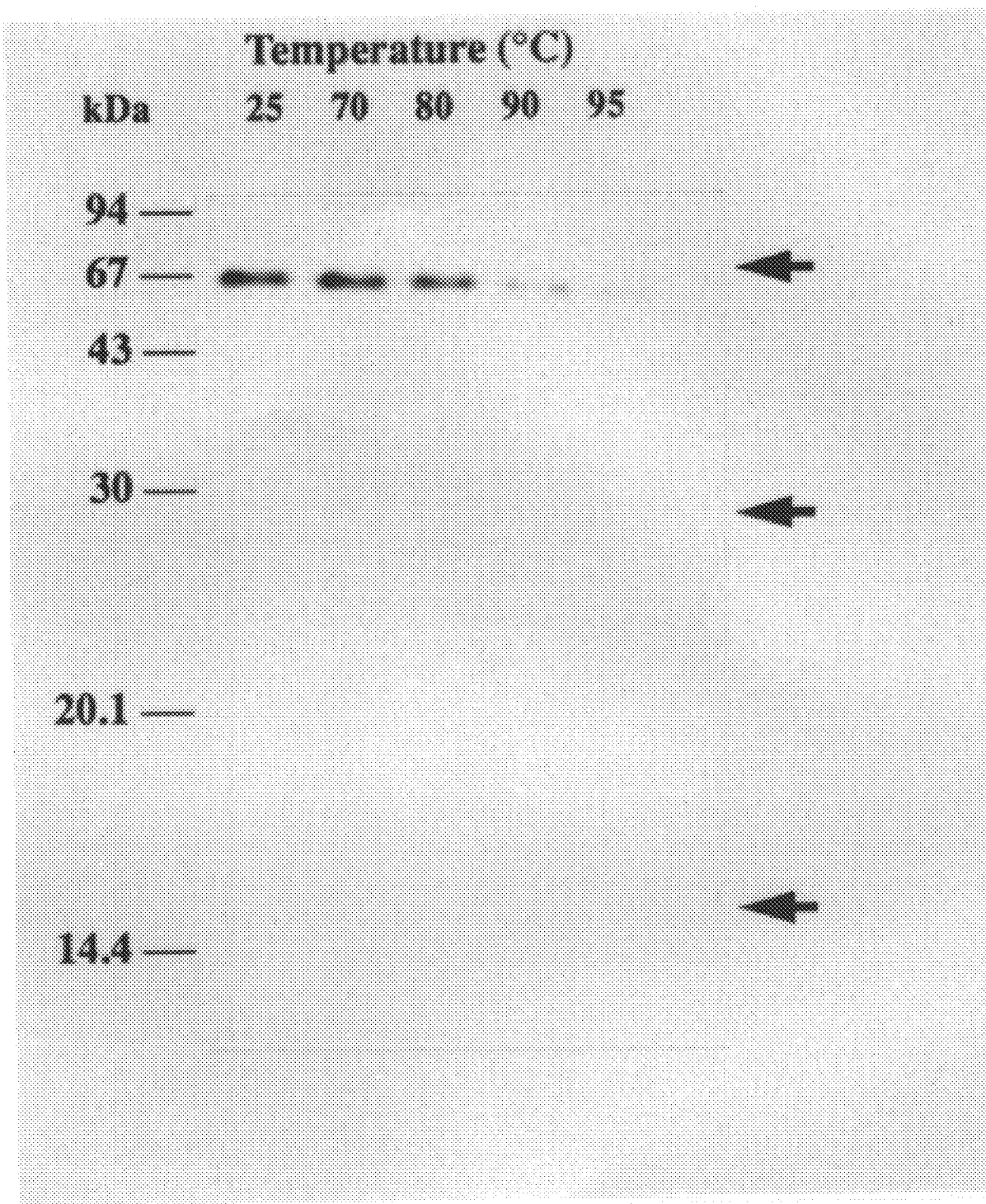
Figure 16C:
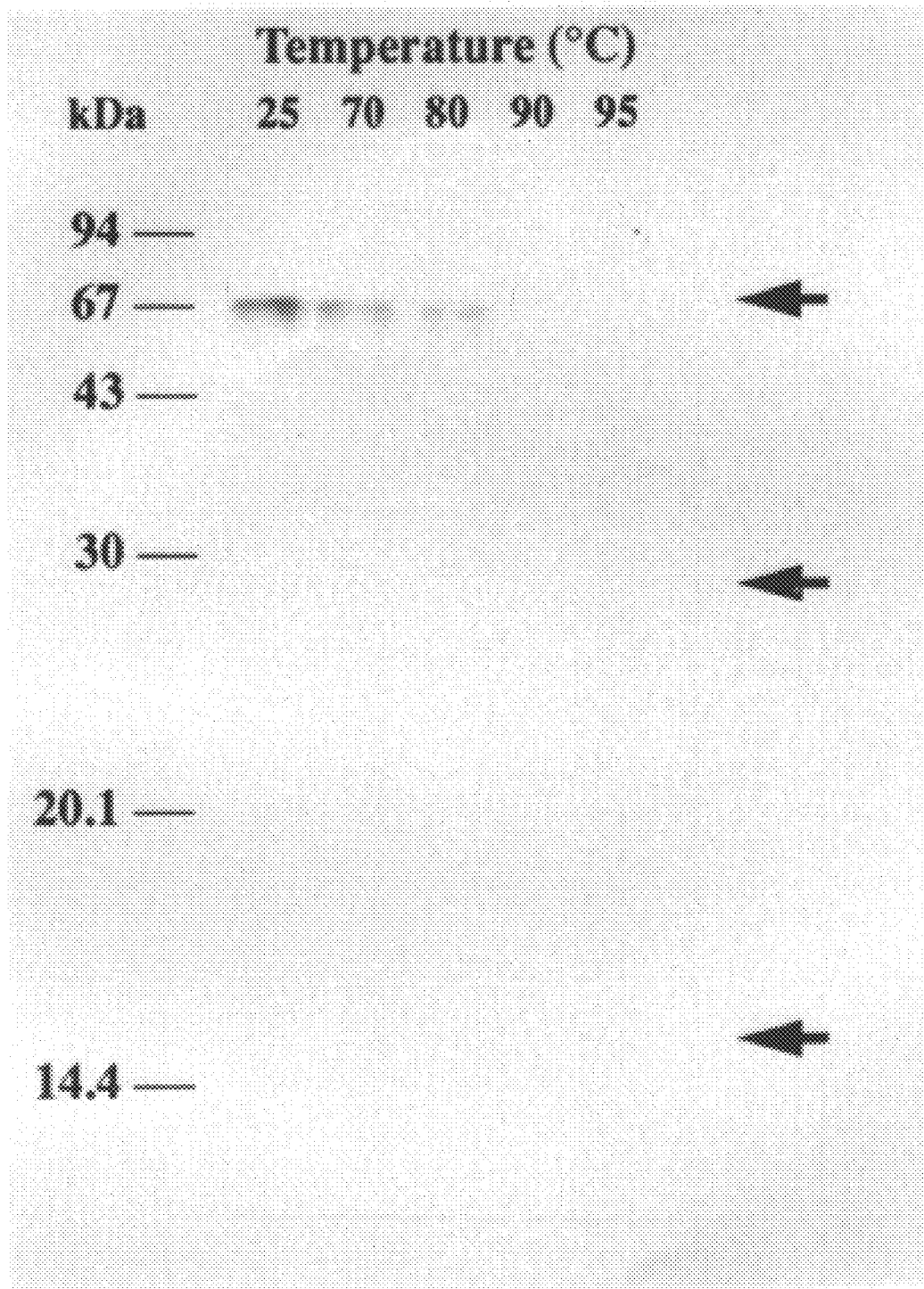
Figure 16D:
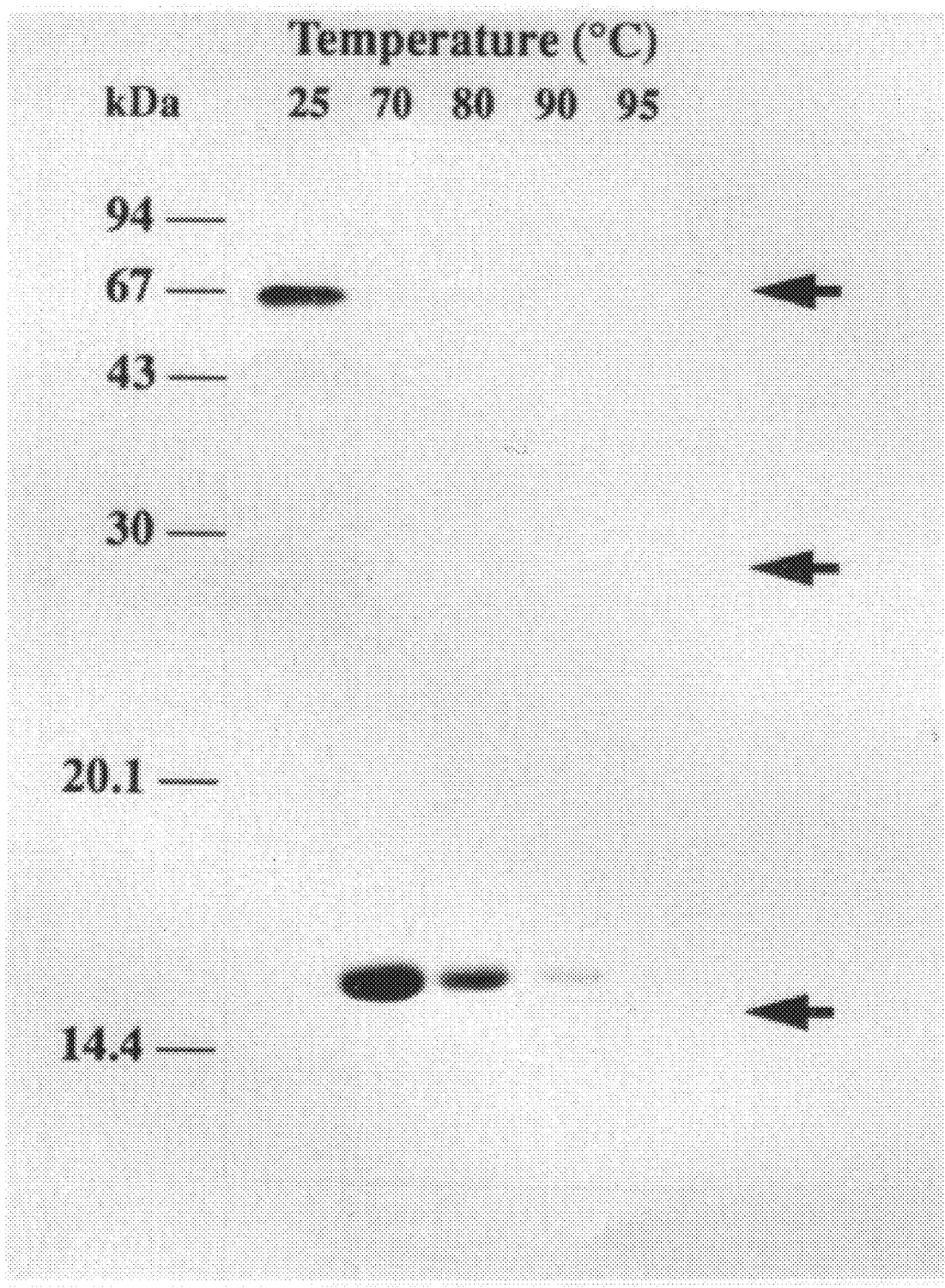
Figure 16E:
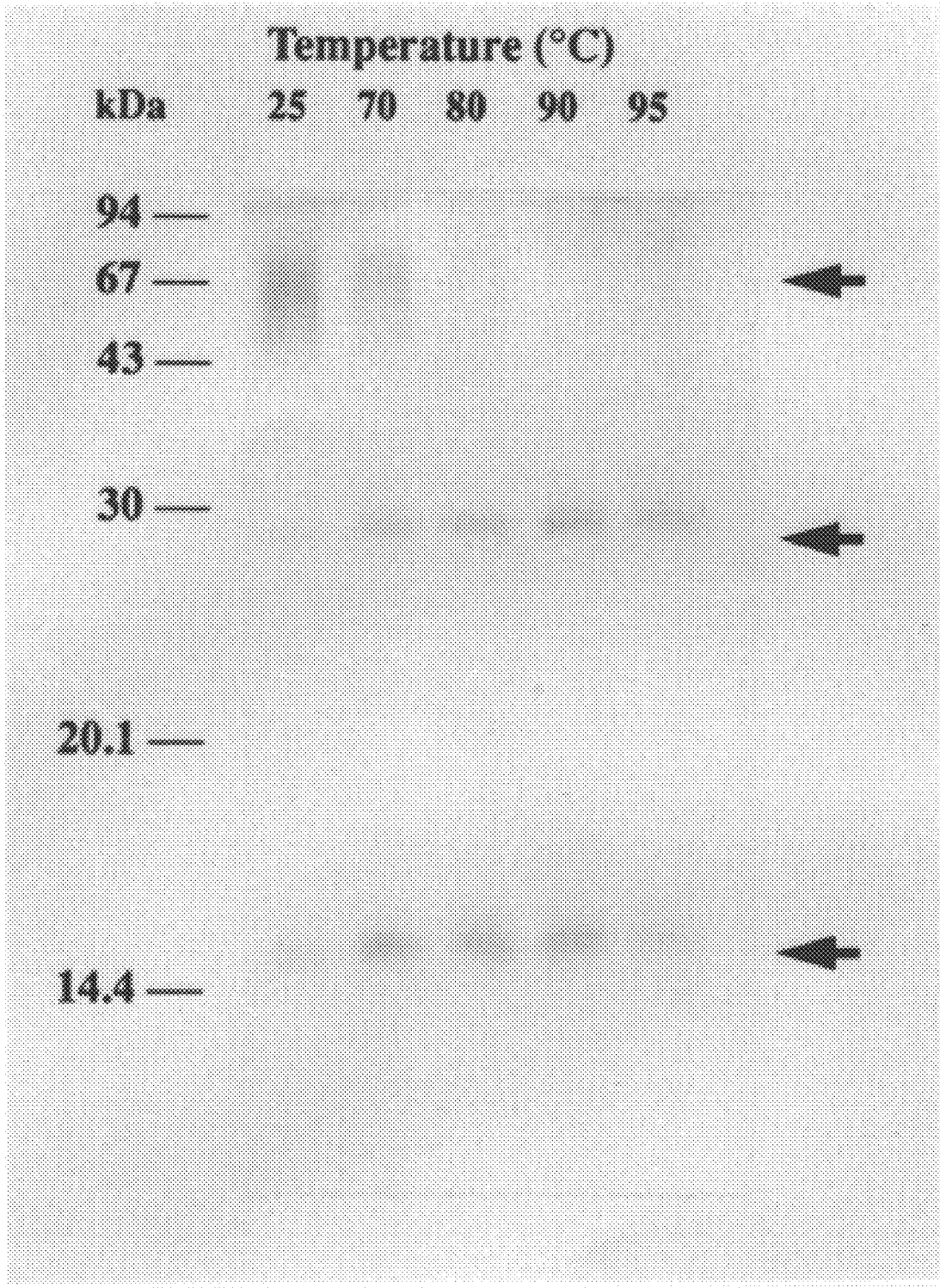

To demonstrate that the streptavidin construct, prepared from a mixture of Stv-D127 and Stv-K127 is a hybrid tetramer, the carboxyl and amino side chains of amino acid 127 of adjacent subunits was crosslinked using the zero-length crosslinker EDC (1-ethyl-3-[3-(dimethylamino) propyl]carbodiimide; Pierce). SDS-PAGE analysis was performed on Stv-K127 and Stv-DK127 before and after crosslinking. Uncrosslinked Stv-K127 (lane 1), Stv-K127 after crosslinking with EDC (lane 2), molecular mass standard proteins (lane 3), uncrosslinked Stv-DK127 (lane 4) and Stv-DK127 after crosslinking with EDC was analyzed in adjacent lanes on a single SDS-PAGE gel (FIG. 15). Subunit dimers (top) and monomers (bottom), shown by arrows in FIG. 15, can easily be distinguished in SDS-PAGE because of their differences in migration velocities. The electrophoretic analysis shows that more than 80% of the subunits formed crosslinked dimers (lane 5). Similar reactions were carried out on Stv-K127 homotetramers, but no such products were observed (lane 2). The high efficiency of crosslinked dimer formation reveals that this streptavidin construct is a hybrid tetramer, in which different subunits are positioned at the dimer—dimer interface at a ratio of Stv-D127 to Stv-K127 of almost one (termed Stv-DK127). This ratio is quite reasonable because tetramers, in which these two different subunits face each other at the dimer—dimer interface, should be electrostatically more stable than other possible combinations. Crosslinking of Stv-DK127 reduced its biotin-binding ability by approximately 10%, suggesting that other crosslinking reactions also occurred within the protein.

Recently, hybrid tetrameric streptavidins have been made by renaturing a mixture of two different denatured subunit species. In one scheme, a denatured subunit dimer, connected via a disulfide bond between the two Cys-127 residues, which is very similar to Stv-C127 in this study, is used as one of the components to limit the subunit composition and configuration of the resulting tetramers. These methods generate mixed populations of tetrameric streptavidins, and thus the purification of the hybrid tetramer species of interest from the others is needed. In contrast, Stv-DK127 can be self-assembled during renaturation in solution, leaving non-associated Stv-D127 precipitated. Thus, a single hybrid tetramer species can be obtained without the need for further purification.

Although all of the crosslinked streptavidins are able to bind biotin, the introduction of covalent bonds across the dimer—dimer interface might affect the binding to biotinylated macromolecules, because across the dimer—dimer interface might affect the binding to biotinylated macromolecules, because reduced structural flexibility around the biotin-binding site, potentially caused by the intersubunit crosslinks, might affect the binding to biotin attached to bulky macromolecules. To test this, each crosslinked streptavidin was analyzed for its ability to bind an end-biotinylated 18 base DNA. Non-denaturing PAGE analysis of streptavidin-biotinylated DNA mixtures indicates that there is no apparent difference in the amount of bound biotinylated DNA among the crosslinked streptavidins and natural core streptavidin. This shows that the introduction of covalent bonds through the dimer—dimer interface has little effect on the ability to bind biotinylated macromolecules.

Example 35
Thermal Stability of Streptavidin Mutants.

All of the crosslinked streptavidins and natural core streptavidin were heated in the absence of biotin to see if the introduction of covalent bonds or the electrostatic interaction at the dimertimer interface could enhance the thermal stability of streptavidin. Each streptavidin construct was heated to temperatures up to 95° C., kept at these temperatures for 10 minutes, and cooled to 25° C. The resulting protein samples were subjected to SDS-Page analysis and biotin-binding assays.

Figure 17:
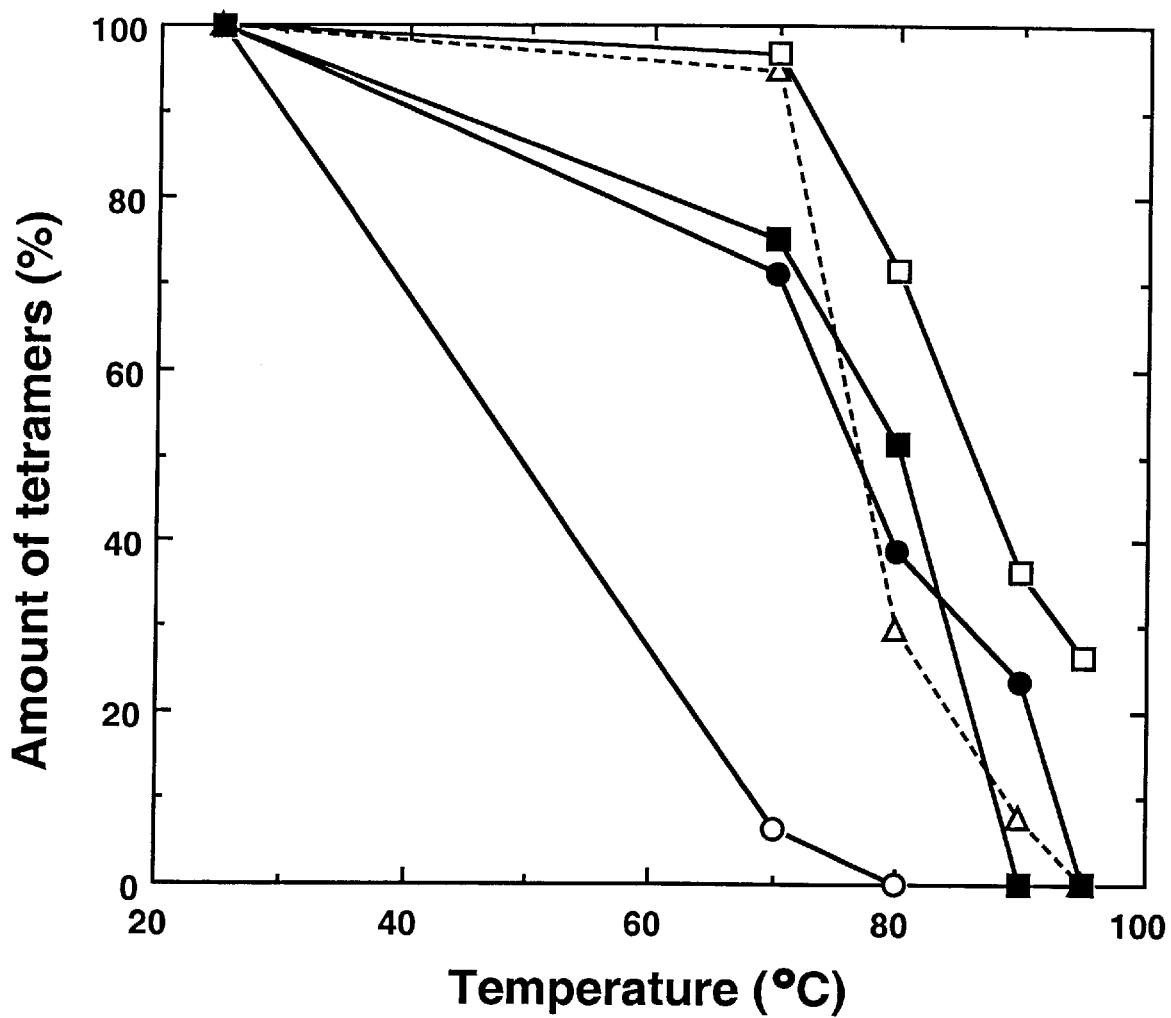
FIG. 17 Comparative summary of the thermal stability of streptavidin proteins with inter-subunit crosslinks by SDS-PAGE analysis.

In SDS-PAGE analysis, streptavidin samples after heat treatment were applied to gels without boiling to maintain the tetrameric structure (FIG. 16, A–E). Proteins were stained with Coomassie brilliant blue or by silver staining, and the amounts of tetrameric molecules were quantitated by densitometry (FIG. 17). Most of natural core streptavidin (74%) dissociated into monomers at 80° C. (FIG. 16A). In contrast, Stv-C127 with disulfide bonds maintained the tetrameric structure at 80° C. (FIG. 16B). Even at 95° C., 26% of these molecules remain tetrameric. Stv-C127 with irreversible crosslinks remained tetrameric at 80° C. (FIG. 16C). After heating to 90°, a fraction of this construct dissociated into subunit dimers and the remaining molecules formed aggregates. Uncrosslinked Stv-DK127 dissociated almost completely into monomers at 70° C. (FIG. 16D), suggesting that the electrostatic attraction between the side chains of Lys-127 and Asp-127 at the dimer—dimer interface is not strong enough to maintain the tetrameric structure under the heating conditions used. Crosslinked Stv-DK127 (FIG. 16E) was more stable at 70° C. than its uncrosslinked derivative, retaining more than 70% of its tetrameric structure at 70° C. The reduced amount of protein migrating into the gel about 25° C. is caused by the formation of high molecular aggregates.

To determine the biotin-binding ability of streptavidin constructs after heat treatment, each streptavidin sample was mixed with excess D-[carbonyl-$^{14}$C]biotin, and unbound biotin, separated by filtration, quantitated. The remaining biotin-binding ability of each streptavidin construct after heat treatment was determined and is plotted as a function of heating temperature. The values for natural core streptavidin (Δ), Stv-C127 with disulfide bonds (□), Stv-C127 crosslinked with 1,3 dibromoacetone (■), uncrosslinked Stv-DK127 (○) and crosslinked Stv-DK127 (●) are superimposed on FIG. 18 for comparison.

The introduction of covalent bonds across the dimer—dimer interface enhances the thermal stability of streptavidin, making it more resistant to both subunit dissociation and loss of biotin-binding ability. The amount of tetrameric molecules after heat treatment (FIG. 17) shows a very high correlation with the remaining biotin binding ability suggesting that the maintenance of the tetrameric structure is essential for streptavidin to retain its biotin-binding ability.

Example 36
Stability of Streptavidin Mutants in Guanidine Hydrochloride.

To test the stability of each streptavidin construct against denaturation by guanidine hydrochloride, each streptavidin construct was saturated with biotin and incubated in 7 M guanidine hydrochloride (pH 0.89). The amount of biotin remaining bound was quantitated after the separation of free, released biotin.

Natural core streptavidin was least stable among the molecules tested, retaining only 35% of bound biotin. Stv-C127 with disulfide bonds across the dimer—dimer interface retained approximately 40% of bound biotin, whereas Stv-C127 with irreversible covalent bonds retained approximately 48% of bound biotin. Uncrosslinked Stv-DK127 and its crosslinked derivative were the most stable of the five protein species tested, retining almost 70% of bound biotin (FIG. 17). These results show that the introduction of covalent bonds between adjacent subunits through the dimer—dimer interface and the enhanced electrostatic attraction between the side chains of Lys-127 and Asp-127 at the dimer—dimer interface contribute to the stability of the streptavidin tetramer in guanidine hydrochloride.

Each streptavidin construct (approximately 160 μpmoles) was incubated for 20 minutes in 15 μl of D-[8,9-$^3$H]biotin (47 Ci/mmol; Amersham) to fill approximately 22 pmoles of the biotin-binding site, followed by the addition of 2 μl of unlabeled biotin to saturate the remaining biotin binding sites. 983 μl of 7 M guanidine hydrochloride (pH 0.89) was added and the mixture was incubated at room temperature for 90 minutes. Control experiments were performed by incubating proteins in 150 mM NaCl, 50 mM ammonium acetate (pH 6.0) without guanidine hydrochloride. Released biotin was separated from streptavidin-biotin complexes by using Ultrafree-MC centrifugal filter units (Millipore) with a molecular mass cutoff of 10 kDa and quantitated by liquid scintillation counting.

Example 37
Binding of Biotinylated DNAs.

Figure 18:
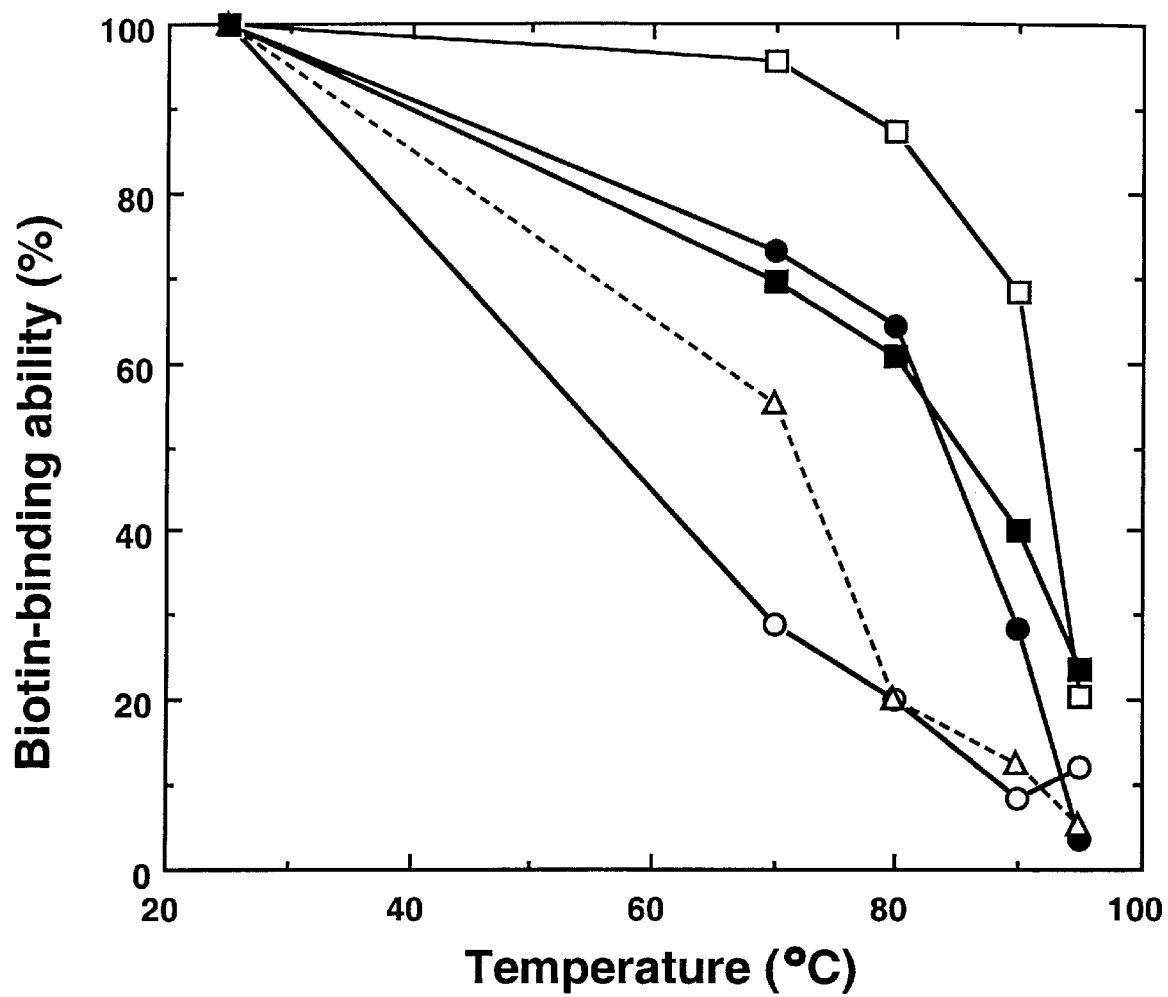
FIG. 18 Comparative summary of the thermal stability of streptavidin proteins with inter-subunit crosslinks by biotin binding assays.

Although all of the two chain-tetramers are able to bind biotin, the introduction of covalent bonds across the dimer—dimer interface would affect the binding to biotinylated macromolecules. To test this, each two-chain tetrameric streptavidin was mixed with an end-biotinylated 18-base oligonucleotide and analyzed by non-denaturing PAGE (FIG. 18). Each mixture contained monomeric, dimeric, trimeric and tetrameric biotinylated targets DNA, bound via single streptavidin molecules. There was no significant difference in the amounts of these bound biotinylated DNA molecules among two-chain tetrameric streptavidins and natural core streptavidin. Although this analysis was not quantitative, these results indicate that the introduction of covalent bonds through the dimer—dimer interface has no appreciable effect on the ability of the two-chain tetramers to bind biotinylated macromolecules.

Each lyophilized streptavidin construct was mixed with a 1:100 molar ratio of an end-biotinylated 18-base DNA in 4.5 M NaCl and the mixture was incubated for two hours. Streptavidin-biotinylated DNA complexes were desalted and electrophoresed through a 15% non-denaturing gel (J. Sambrook et al.,*Molecular Cloning: A Laboratory Manual*, 2nd Ed., Cold Spring Harbor Laboratory Press, Cold Spring Harbor, N.Y., 1989).

Introduction of covalent bonds between subunits across the dimer—dimer interface enhances the overall stability of the streptavidin tetramer with little effect on the biotin-binding ability. The enhanced ability of two-chain tetramers to retain biotin shows that the disruption of the tetramer along the dimer—dimer interface is one of the causes that can be associated with the release of biotin from streptavidin. These two chain tetrameric streptavidins are useful in bioanalytical applications. For example, immobilization of these proteins on solid surfaces would provide stable binding of biotinylated macromolecules, because the enhanced stability of the tetramer would prevent the release of such biotinylated biomolecules, caused by the subunit dissociation or loosening of subunit association within a streptavidin tetramer.

Other embodiments and uses of the invention will be apparent to those skilled in the art from consideration of the specification and practice of the invention disclosed herein. All documents including U.S. patents and patent applications disclosed herein are specifically incorporated by reference. The specification and examples should be considered exemplary only with the true scope and spirit of the invention indicated by the following claims.

---

(1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 159 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:1:

```
Xaa Pro Ser Lys Asp Ser Lys Ala Gln Val Ser Ala Ala Glu Ala Gly
 1               5                  10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
        130                 135                 140

Lys Ala Gly Val Asn Asn Gly Asn Pro Leu Asp Ala Val Gln Gln
145                 150                 155
```

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

ACCAGCGTGG ACTTGAAGGC GTTGGCCTCG                                    30

(2) INFORMATION FOR SEQ ID NO:3:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

AGGTGTCGTC GCCGACCA                                                 18

(2) INFORMATION FOR SEQ ID NO:4:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

AATACGACTC ACTATAG                                                  17

(2) INFORMATION FOR SEQ ID NO:5:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

GTTGTTCGAA GTCAGCAGCC ACTGGGT                                            27

(2) INFORMATION FOR SEQ ID NO:6:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

TTGCTTCGAA GTCCACGCTG GTCGGC                                             26

(2) INFORMATION FOR SEQ ID NO:7:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

CGGGCTTTGT TAGCAGCCGG A                                                  21

(2) INFORMATION FOR SEQ ID NO:8:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

AATTGCTGCT GCTGCTGCTA A                                                  21

(2) INFORMATION FOR SEQ ID NO:9:

(i) SEQUENCE CHARACTERISTICS:

```
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

GATCTTAGCA GCAGCAGCAG C                                            21
```

We claim:

1. A streptavidin protein comprising a subunit peptide consisting of SEQ ID NO 1 from positions 16 to 133, wherein said peptide has an amino acid substitution at position 127.

2. The streptavidin protein of claim 1 which binds to at least about 0.80 molecules of biotin per subunit in 6 M guanidine-hydrochloride at pH 7.4.

3. The streptavidin protein of claim 1 which binds to at least about 0.90 molecules of biotin per subunit in 6 M guanidine-hydrochloride at pH 7.4.

4. The streptavidin protein of claim 1 which binds to at least about 0.80 molecules of biotin per subunit in 4 M guanidine-hydrochloride at pH 1.5.

5. The streptavidin protein of claim 1 which binds to at least about 0.70 molecules of biotin per subunit in 6 M guanidine-hydrochloride at pH 1.5.

6. The streptavidin protein of claim 1 which is substantially soluble in less than 80% ethanol.

7. The streptavidin protein of claim 1 which is substantially soluble in up to 90% ammonium sulfate.

8. The streptavidin protein of claim 1 wherein the histidine at position 127 of natural streptavidin is replaced with lysine.

9. The streptavidin protein of claim 1 which is a dimer or a tetramer.

10. A streptavidin peptide consisting of SEQ ID NO 1 from positions 16 to 133, wherein said peptide has an amino acid substitution at position 127.

11. The streptavidin peptide of claim 10 wherein said reptide has a deletion of the sequence from positions 113 to 120.

12. The streptavidin peptide of claim 10 further comprising one or more cysteines attached to a terminus of said peptide.

13. The streptavidin peptide of claim 12 which possesses 5 cysteines attached to a carboxyl terminus.

14. The streptavidin protein of claim 10, which is coupled to a solid support.

15. The streptavidin protein of claim 14 wherein the solid support is selected from the group consisting of surfaces of plastic, glass, ceramics, silicon, cellulose, gels and metals.

16. The streptavidin protein of claim 14 wherein the solid support is selected from the group consisting of beads, tubes, chips, resins, plates, wells, films, sticks, magnetic beads, porous membranes and combinations thereof.

17. The streptavidin protein of claim 10, which is coupled to a biological agent.

18. The streptavidin protein of claim 17 wherein the biological agent is an antibody, an antigen, a hormone, a pharmaceutical, a cytokine or a cell.

19. The streptavidin protein of claim 18 wherein the cell is a mammalian, bacterial, parasitic, insect, fungal or yeast cell.

20. A streptavidin peptide consisting of SEQ ID NO 1 from positions 16 to 133 wherein said peptide has a deletion of the sequence from positions 113 to 120.

21. A biotin-binding streptavidin peptide comprising a portion of SEQ ID NO 1, said portion containing an aspartic acid at position 127.

22. A biotin-binding streptavidin peptide comprising a portion of SEQ ID NO 1, said portion containing a lysine at position 127.

23. A biotin-binding streptavidin peptide comprising a portion of SEQ ID NO 1, said portion containing a cysteine at position 127.

24. A streptavidin protein comprising a first streptavidin peptide, said first peptide comprising a portion of SEQ ID NO 1, said portion containing a lysine at position 127 and a second streptavidin peptide, said second peptide comprising a portion of SEQ ID NO 1, said portion containing an aspartic acid at position 127.

25. The streptavidin protein of claim 24 which comprises 2 or 4 streptavidin peptides.

26. The streptavidin protein of claim 24 which retains greater than about 90% of bound biotin at 60° C.

27. The streptavidin protein of claim 24 which retains greater than about 80% of bound biotin at 60° C.

28. The streptavidin protein of claim 24 which retains greater than about 50% of bound biotin at 80° C.

29. The streptavidin protein of claim 24 wherein the streptavidin peptides are cross-linked.

30. A streptavidin protein comprising a plurality of biotin-binding streptavidin subunit peptides, said subunit peptides comprising a portion of SEQ ID NO 1, said portion containing a cysteine at position 127.

31. The streptavidin protein of claim 30 which comprises 2 or 4 streptavidin peptides.

* * * * *

UNITED STATES PATENT AND TRADEMARK OFFICE
CERTIFICATE OF CORRECTION

PATENT NO. : 6,022,951
DATED : February 8, 2000
INVENTOR(S) : Takeshi Sano et al.

It is certified that error appears in the above-identified patent and that said Letters Patent is hereby corrected as shown below:

<u>Title page,</u>
Assignee, insert -- Trustees of Boston University --.

Signed and Sealed this

Nineteenth Day of March, 2002

Attest:

Attesting Officer

JAMES E. ROGAN
Director of the United States Patent and Trademark Office